US012186370B1

(12) United States Patent
Varghese et al.

(10) Patent No.: US 12,186,370 B1
(45) Date of Patent: Jan. 7, 2025

(54) ACTRIIB LIGAND TRAP COMPOSITIONS AND USES THEREOF

(71) Applicant: CELGENE CORPORATION, Summit, NJ (US)

(72) Inventors: Johnson Varghese, Lexington, MA (US); David Mahon, Budd Lake, NJ (US); Nandakumar Madayiputhiya, Scarsdale, NY (US); Kendall Davis Carey, Yardley, PA (US); Promod Kumar Mehndiratta, Chester Springs, PA (US); Ping Carlson, Skillman, NJ (US); Rajeev Boregowda, Somerset, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 17/519,305

(22) Filed: Nov. 4, 2021

Related U.S. Application Data

(60) Provisional application No. 63/110,331, filed on Nov. 5, 2020.

(51) Int. Cl.
*A61K 38/17* (2006.01)
*C07K 14/71* (2006.01)
*C07K 14/715* (2006.01)

(52) U.S. Cl.
CPC ........ *A61K 38/179* (2013.01); *A61K 38/1793* (2013.01); *C07K 14/71* (2013.01); *C07K 14/715* (2013.01); *C07K 2319/30* (2013.01); *C07K 2319/32* (2013.01)

(58) Field of Classification Search
CPC .......................... A61K 38/179; C07K 2319/30
See application file for complete search history.

(56) References Cited

U.S. PATENT DOCUMENTS

| 7,612,041 B2 | 11/2009 | Knopf et al. |
|---|---|---|
| 7,709,605 B2 | 5/2010 | Knopf et al. |
| 7,842,663 B2 | 11/2010 | Seehra et al. |
| 7,951,771 B2 | 5/2011 | Knopf et al. |
| 7,960,343 B2 | 6/2011 | Knopf et al. |
| 7,988,973 B2 | 8/2011 | Sherman |
| 8,007,809 B2 | 8/2011 | Sherman |
| 8,058,229 B2 | 11/2011 | Seehra et al. |
| 8,067,360 B2 | 11/2011 | Knopf et al. |
| 8,128,933 B2 | 3/2012 | Knopf et al. |
| 8,138,142 B2 | 3/2012 | Seehra et al. |
| 8,173,601 B2 | 5/2012 | Knopf et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,881 B2 | 10/2012 | Seehra et al. |
| 8,361,957 B2 | 1/2013 | Seehra et al. |
| 8,367,611 B2 | 2/2013 | Knopf et al. |
| 8,629,109 B2 | 1/2014 | Knopf et al. |
| 8,703,694 B2 | 4/2014 | Knopf et al. |
| 8,703,927 B2 | 4/2014 | Seehra et al. |
| 8,710,016 B2 | 4/2014 | Seehra et al. |
| 8,895,016 B2 | 11/2014 | Sherman et al. |
| 9,138,459 B2 | 9/2015 | Knopf et al. |
| 9,163,075 B2 | 10/2015 | Knopf et al. |
| 9,181,533 B2 | 11/2015 | Seerah et al. |
| 9,353,356 B2 | 5/2016 | Knopf et al. |
| 9,399,669 B2 | 7/2016 | Knopf et al. |
| 9,439,945 B2 | 9/2016 | Seehra et al. |
| 9,505,813 B2 | 11/2016 | Seehra et al. |
| 9,526,759 B2 | 12/2016 | Knopf et al. |
| 9,572,865 B2 | 2/2017 | Knopf et al. |
| 9,617,319 B2 | 4/2017 | Seehra et al. |
| 9,745,559 B2 | 8/2017 | Seehra et al. |
| 9,790,284 B2 | 10/2017 | Knopf et al. |
| 9,850,298 B2 | 12/2017 | Attie |
| 9,919,030 B2 | 3/2018 | Sherman et al. |
| 9,932,379 B2 | 4/2018 | Seehra et al. |
| 10,071,135 B2 | 9/2018 | Knopf et al. |
| 10,093,707 B2 | 10/2018 | Sherman et al. |
| 10,131,700 B2 | 11/2018 | Seehra et al. |
| 10,189,882 B2 | 1/2019 | Attie et al. |
| 10,195,249 B2 | 2/2019 | Sung et al. |
| 10,259,861 B2 | 4/2019 | Knopf et al. |
| 10,358,633 B2 | 7/2019 | Seehra et al. |
| 10,377,996 B2 | 8/2019 | Seehra et al. |

(Continued)

FOREIGN PATENT DOCUMENTS

JP 2016508504 A * 3/2016
WO WO 2007/062188 3/2007

(Continued)

OTHER PUBLICATIONS

Sakaue et al., American Chemical Soc. Omega 2:260-267, (2017).*
Wakankar et al., J. Pharmaceutical Sci. 95: 2312-2336, (2006).*
Kim et al., Biochim. Biophys. Acta. 1840(2), ( 2014).*
Silva et al., Free Radical Biol. and Med. 65: 925-941, (2013).*
Irudayanathan, MABS, vol. 14 (14 pages), 2022.*
Attisano et al., 1992, "Novel activin receptors: distinct genes and alternative mRNA splicing generate a repertoire of serine/threonine kinase receptors," Cell, 68(1):97-108.
Fenaux et al., 2013, "How we treat lower-risk myelodysplastic syndrome," Blood, 121(21):4280-4286.

(Continued)

*Primary Examiner* — Gyan Chandra
(74) *Attorney, Agent, or Firm* — Jones Day

(57) ABSTRACT

The present application relates to recombinant fusion proteins consisting of the extracellular domain (ECD) of human activin receptor IIB (ActRIIB) linked to a constant domain of an immunoglobulin, wherein the protein acts as an ActRIIB ligand trap, and compositions of the same comprising particular sequence variants. The present application further relates to method of making such recombinant fusion proteins and uses of such recombinant fusion proteins in the treatment of various diseases.

6 Claims, 24 Drawing Sheets

Specification includes a Sequence Listing.

(56) References Cited

U.S. PATENT DOCUMENTS

| | | |
|---|---|---|
| 10,487,144 B2 | 11/2019 | Attie |
| 10,548,976 B2 | 2/2020 | Cappellini et al. |
| 10,550,170 B2 | 2/2020 | Sherman et al. |
| 10,689,427 B2 | 6/2020 | Seehra et al. |
| 10,695,405 B2 | 6/2020 | Kumar et al. |
| 10,722,558 B2 | 7/2020 | Kumar et al. |
| 10,889,626 B2 | 1/2021 | Seehra et al. |
| 10,968,282 B2 | 4/2021 | Knopf et al. |
| 11,066,654 B2 | 7/2021 | Seehra et al. |
| 11,471,510 B2 | 10/2022 | Attie et al. |
| 2007/0249022 A1 | 10/2007 | Knopf et al. |
| 2009/0047281 A1 | 2/2009 | Sherman |
| 2009/0074768 A1 | 3/2009 | Knopf et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0163417 A1 | 6/2009 | Sherman |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0113932 A1 | 5/2010 | Antich et al. |
| 2010/0183624 A1 | 7/2010 | Seehra et al. |
| 2010/0267133 A1 | 10/2010 | Knopf et al. |
| 2010/0310577 A1 | 12/2010 | Knopf et al. |
| 2010/0316644 A1 | 12/2010 | Seehra et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2012/0003218 A1 | 1/2012 | Sherman et al. |
| 2012/0015877 A1 | 1/2012 | Seehra et al. |
| 2012/0052067 A1 | 3/2012 | Sherman |
| 2012/0148588 A1 | 6/2012 | Knopf et al. |
| 2012/0156204 A1 | 6/2012 | Seehra et al. |
| 2013/0004489 A1 | 1/2013 | Knopf et al. |
| 2013/0065299 A1 | 3/2013 | Knopf et al. |
| 2013/0177559 A1 | 7/2013 | Seehra et al. |
| 2013/0184210 A1 | 7/2013 | Knopf et al. |
| 2013/0195862 A1 | 8/2013 | Knopf et al. |
| 2013/0243743 A1 | 9/2013 | Seehra et al. |
| 2013/0244324 A1 | 9/2013 | Seehra et al. |
| 2014/0079700 A1 | 3/2014 | Knopf et al. |
| 2014/0314759 A1 | 10/2014 | Seehra et al. |
| 2014/0322203 A1* | 10/2014 | Alavattam ............ A61K 47/26 424/130.1 |
| 2014/0328845 A1 | 11/2014 | Knopf et al. |
| 2015/0023970 A1 | 1/2015 | Seehra et al. |
| 2015/0056200 A1 | 2/2015 | Seehra et al. |
| 2015/0158923 A1 | 6/2015 | Sherman et al. |
| 2015/0183845 A1 | 7/2015 | Sherman et al. |
| 2015/0266950 A1 | 9/2015 | Sung et al. |
| 2015/0276766 A1 | 10/2015 | Sung et al. |
| 2015/0283209 A1 | 10/2015 | Sung et al. |
| 2015/0361163 A1 | 12/2015 | Kumar et al. |
| 2016/0039922 A1 | 2/2016 | Attie |
| 2016/0108379 A1 | 4/2016 | Knopf et al. |
| 2016/0120939 A1 | 5/2016 | Knopf et al. |
| 2016/0186148 A1 | 6/2016 | Seehra et al. |
| 2016/0264681 A1 | 9/2016 | Seehra et al. |
| 2016/0279197 A1 | 9/2016 | Sherman et al. |
| 2016/0279203 A1 | 9/2016 | Sherman et al. |
| 2016/0289286 A1 | 10/2016 | Attie et al. |
| 2016/0318983 A1 | 11/2016 | Koncarevic et al. |
| 2016/0319254 A1 | 11/2016 | Knopf et al. |
| 2016/0326228 A1 | 11/2016 | Seehra et al. |
| 2017/0058016 A1 | 3/2017 | Knopf et al. |
| 2017/0137791 A1 | 5/2017 | Seehra et al. |
| 2017/0145074 A1 | 5/2017 | Knopf et al. |
| 2017/0190784 A1 | 7/2017 | Knopf et al. |
| 2017/0204382 A1 | 7/2017 | Seehra et al. |
| 2017/0274077 A1 | 9/2017 | Kumar et al. |
| 2017/0291935 A1 | 10/2017 | Sherman et al. |
| 2017/0304397 A1 | 10/2017 | Hruska et al. |
| 2017/0320925 A1 | 11/2017 | Seehra et al. |
| 2017/0327800 A1 | 11/2017 | Seehra et al. |
| 2017/0360887 A1 | 12/2017 | Attie et al. |
| 2018/0009872 A1 | 1/2018 | Sherman et al. |
| 2018/0037622 A1 | 2/2018 | Seehra et al. |
| 2018/0050085 A1 | 2/2018 | Kumar et al. |
| 2018/0050089 A1 | 2/2018 | Kumar et al. |
| 2018/0080012 A1 | 3/2018 | Seehra et al. |
| 2018/0125928 A1 | 5/2018 | Attie et al. |
| 2018/0161426 A1 | 6/2018 | Cappellini et al. |
| 2018/0162954 A1 | 6/2018 | Knopf et al. |
| 2018/0194828 A1 | 7/2018 | Seehra et al. |
| 2018/0194834 A1 | 7/2018 | Attie |
| 2018/0221447 A1 | 8/2018 | Kumar et al. |
| 2019/0049469 A1 | 2/2019 | Sung et al. |
| 2019/0062392 A1 | 2/2019 | Koncarevic et al. |
| 2019/0192625 A1 | 6/2019 | Knopf et al. |
| 2019/0225664 A1 | 7/2019 | Sherman et al. |
| 2019/0233486 A1 | 8/2019 | Attie et al. |
| 2019/0262423 A1 | 8/2019 | Sung et al. |
| 2019/0263876 A1 | 8/2019 | Seehra et al. |
| 2019/0352619 A1 | 11/2019 | Kumar et al. |
| 2020/0031903 A1 | 1/2020 | Sherman |
| 2020/0071381 A1 | 3/2020 | Knopf et al. |
| 2020/0071383 A1 | 3/2020 | Sherman et al. |
| 2020/0101134 A1 | 4/2020 | Gale et al. |
| 2020/0101157 A1 | 4/2020 | Cappellini et al. |
| 2020/0109193 A1 | 4/2020 | Attie |
| 2020/0148788 A1 | 5/2020 | Knopf et al. |
| 2020/0157512 A1 | 5/2020 | Seehra et al. |
| 2020/0165583 A1 | 5/2020 | Seehra et al. |
| 2020/0181217 A1 | 6/2020 | Seehra et al. |
| 2020/0181218 A1 | 6/2020 | Seehra et al. |
| 2020/0199186 A1 | 6/2020 | Seehra et al. |
| 2020/0199546 A1 | 6/2020 | Seehra et al. |
| 2020/0199547 A1 | 6/2020 | Seehra et al. |
| 2020/0199548 A1 | 6/2020 | Seehra et al. |
| 2020/0208124 A1 | 7/2020 | Seehra et al. |
| 2020/0255495 A1 | 8/2020 | Sherman et al. |
| 2020/0360475 A1 | 11/2020 | Sherman et al. |
| 2020/0384080 A1 | 12/2020 | Kumar et al. |
| 2020/0390860 A1 | 12/2020 | Kumar et al. |
| 2020/0397865 A1 | 12/2020 | Kumar et al. |
| 2020/0405814 A1 | 12/2020 | Kumar et al. |
| 2021/0023174 A1 | 1/2021 | Kumar et al. |
| 2021/0038689 A1 | 2/2021 | Sherman et al. |
| 2021/0115105 A1 | 4/2021 | Seehra et al. |
| 2021/0188955 A1 | 6/2021 | Kumar et al. |
| 2021/0207107 A1 | 7/2021 | Seehra et al. |
| 2021/0230239 A1 | 7/2021 | Attie et al. |
| 2021/0253658 A1 | 8/2021 | Seehra et al. |
| 2021/0261682 A1 | 8/2021 | Knopf et al. |
| 2021/0269494 A1 | 9/2021 | Koncarevic et al. |
| 2021/0299216 A1 | 9/2021 | Kumar et al. |
| 2021/0299220 A1 | 9/2021 | Kumar et al. |
| 2021/0322514 A1 | 10/2021 | Kumar et al. |
| 2021/0346464 A1 | 11/2021 | Laadem et al. |
| 2021/0355181 A1 | 11/2021 | Sherman et al. |
| 2021/0355191 A1 | 11/2021 | Sherman |
| 2022/0017639 A1 | 1/2022 | Knopf et al. |
| 2022/0041670 A1 | 2/2022 | Seehra et al. |
| 2022/0098559 A1 | 3/2022 | Seehra et al. |
| 2022/0118049 A1 | 4/2022 | Sherman et al. |
| 2022/0169996 A1 | 6/2022 | Seehra et al. |
| 2022/0281951 A1 | 9/2022 | Knopf et al. |

FOREIGN PATENT DOCUMENTS

| | | |
|---|---|---|
| WO | WO 2008/076437 | 6/2008 |
| WO | WO 2010/019261 | 2/2010 |
| WO | WO 2010/083034 | 7/2010 |
| WO | WO 2010/144452 | 12/2010 |
| WO | WO 2010/151426 | 12/2010 |
| WO | WO 2011/020045 | 2/2011 |
| WO | WO 2011/031901 | 3/2011 |
| WO | WO 2013/059347 | 4/2013 |
| WO | WO 2014/066486 | 5/2014 |

(56) References Cited

FOREIGN PATENT DOCUMENTS

| WO | WO 2014/066487 | 5/2014 |
| WO | WO 2014/071158 | 8/2014 |
| WO | WO 2015/161220 | 10/2015 |
| WO | WO 2015/192111 | 12/2015 |
| WO | WO 2016/069234 | 5/2016 |
| WO | WO 2016/090077 | 6/2016 |
| WO | WO 2016/090188 | 6/2016 |
| WO | WO 2016/183280 | 11/2016 |
| WO | WO 2016/187378 | 11/2016 |
| WO | WO 2017/079591 | 5/2017 |
| WO | WO 2017/091706 | 6/2017 |
| WO | WO 2018/022762 | 2/2018 |
| WO | WO 2018/067874 | 4/2018 |
| WO | WO 2018/231905 | 12/2018 |
| WO | WO 2020/092523 | 5/2020 |
| WO | WO 2021/211418 | 10/2021 |
| WO | WO 2021/231851 | 11/2021 |

OTHER PUBLICATIONS

Fenaux et al., 2014, "Myelodysplastic syndromes: ESMO Clinical Practice Guidelines for diagnosis, treatment and follow-up," Annals of Oncology, 25(Suppl. 3):iii57-iii69.

GenBank Accession No. NP_001097.2; 2020, Activin receptor type-2B precursor [Homo sapiens]; (3 pages); retrieved from the internet on Feb. 7, 2020 from <https:www.ncbi.nlm.nih.gov/protein/NP_001097.2>.

GenBank NM_001106.3, Homo sapiens activin A receptor, type IIb (ACVR2B), mRNA, http://www.ncbi.nlm.nih.gov/entrez/viewer.fcgi?db=nucleotide&val=116734707 (Downloaded on Jan. 29, 2007).

GenBank Accession No. NP_001265508.1; 2020, Activin receptor type-2A isoform 1 precursor [Homo sapiens]; (3 pages), retrieved from the internet on Feb. 7, 2020 from <https://www.ncbi.nlm.nih.gov/protein/NP_001265508.1>.

GenBank Accession No. NM_001278579, 2020, "Homo sapiens activin A receptor type 2A (ACVR2A), transcript variant 1, mRNA", (5 pages), retrieved from the internet on Feb. 7, 2020 from <https://ncbi.nlm.nih.gov/nuccore/NM_001278579.

Greenberg et al., 1997, "International scoring system for evaluating prognosis in myelodysplastic syndromes," Blood, 89(6):2079-2088.

Greenberg et al., 2012, "Revised International Prognostic Scoring System for Myelodysplastic Syndromes," Blood, 120(12):2454-2465.

Heaney and Golde, 1999, "Myelodysplasia," The New England Journal of Medicine, 340(21):1649-1660.

Hellstrom-Lindberg et al., 2003, "A Validated Decision Model for Treating the Anaemia of Myelodysplastic Syndromes with Erythropoietin + Granulocyte Colony-Stimulating Factor: Significant Effects on Quality of Life," British Journal of Hematology, 120(6):1037-1046.

Hochuli et al., 1987, "New metal chelate adsorbent selective for proteins and peptides containing neighbouring histidine residues", Journal of Chromatography, 411:177-184.

Janknecht et al., 1991, "Rapid and efficient purification of native histidine- tagged protein expressed by recombinant vaccinia virus," Proceedings of the National Academy of Sciences (PNAS), 88(20):8972-8976.

Komrokji and List, 2011, "Role of lenalidomide in the treatment of myelodysplastic syndromes," Seminars in Oncology, 38(5):648-657.

Lee and McPherron, 2001, "Regulation of Myostatin Activity and Muscle Growth," PNAS, 98(16):9306-9311.

Malcovati et al., 2013, "Diagnosis and treatment of primary myelodysplastic syndromes in adults: recommendations from the European LeukemiaNet," Blood, 122(17):2943-2964.

Mathews and Vale, 1991, "Expression Cloning of an Activin Receptor, a Predicted Transmembrane Serine Kinase," Cell, 65(6):973-982.

Oh et al., 2002, "Activin type IIA and IIB receptors mediate Gdf11 signaling in axial vertebral patterning," Genes & Development, 16:2749-2754.

Sako et al., 2010, "Characterization of the Ligand Binding Functionality of the Extracellular Domain of Activin Receptor Type IIB," The Journal of Biological Chemistry, 285(27):21037-21048.

Santini, 2011, "Clinical Use of Erythropoietic Stimulating Agents in Myelodysplastic Syndromes," The Oncologist, 16(Supp. 3):35-42.

Suragani et al., 2014, "Transforming growth factor-β superfamily ligand trap ACE-536 corrects anemia by promoting late-stage erythropoiesis", Nature Medicine, 20(4):408-414.

Walker et al., 2017, "Structural basis for potency differences between GDF8 and GDF11," BMC Biology, 15(1):19.

Yamashita et al., 1995, "Osteogenic protein-1 binds to activin type II receptors and induces certain activin-like effects," Journal of Cell Biology, 130(1):217-226.

Yeo and Whitman, 2001, "Nodal signals to Smads through Cripto-dependent and Cripto-independent mechanisms," Molecular Cell, 7(5):949-957.

* cited by examiner

FIG. 21

```
      M   D   A   M   K   R     G   L   C   C   V   L     L   L   C   G   A   V
   1 ATGGATGCAATGAAGAGA GGGCTCTGCTGTGTGCTG CTGCTGTGTGGAGCAGTC
      P   V   S   P   G   A     A   E   T   R   C     I   Y   Y   N   A   N
  55 TTCGTTTCGCCCGGCGCC GCCGAAACCCGCGAATGT ATTTATTACAATGCTAAT
      W   E   L   E   R   T     N   Q   S   G   L   E     R   C   E   G   E   Q
 109 TGGGAACTCGAACGGACG AACCAATCCGGGCTCGAA CGGTGTGAGGGGGAACAG
      D   K   R   L   H   C     Y   A   S   W   R   N     S   S   G   T   I   E
 163 GATAAACGCCTCCATTGC TATGCGTCGTGGAGGAAC TCCTCCGGGACGATTGAA
      L   V   K   K   G   C     W   D   D   D   F   N     C   Y   D   R   Q   E
 217 CTGGTCAAGAAAGGGTGC TGGGACGACGATTTCAAT TGTTATGACCGCCAGGAA
      C   V   A   T   E   E     N   P   Q   V   Y   F     C   C   C   E   G   N
 271 TGTGTCGCGACCGAAGAG AATCCGCAGGTCTATTTC TGTTGTTGCGAGGGGAAT
      F   C   N   E   R   F     T   H   L   P   E   A     G   G   P   E   V   T
 325 TTCTGTAATGAACGGTTT ACCCACCTCCCCGAAGCC GGCGGGCCCGAGGTGACC
      Y   E   P   P   P   T     G   G   G   T   H   T     C   P   P   C   P   A
 379 TATGAACCCCCGCCCACC GGTGGTGGAACTCACACA TGCCCACCGTGCCCAGCA
      P   E   L   L   G   G     P   S   V   F   L   F     P   P   K   P   K   D
 433 CCTGAACTCCTGGGGGGA CCGTCAGTCTTCCTCTTC CCCCCAAAACCCAAGGAC
      T   L   M   I   S   R     T   P   E   V   T   C     V   V   V   D   V   S
 487 ACCCTCATGATCTCCCGG ACCCCTGAGGTCACATGC GTGGTGGTGGACGTGAGC
      H   E   D   P   E   V     K   F   N   W   Y   V     D   G   V   E   V   H
 541 CACGAAGACCCTGAGGTC AAGTTCAACTGGTACGTG GACGGCGTGGAGGTGCAT
      N   A   K   T   K   P     R   E   E   Q   Y   N     S   T   Y   R   V   V
 595 AATGCCAAGACAAAGCCG CGGGAGGAGCAGTACAAC AGCACGTACCGTGTGGTC
      S   V   L   T   V   L     H   Q   D   W   L   N     G   K   E   Y   K   C
 649 AGCGTCCTCACCGTCCTG CACCAGGACTGGCTGAAT GGCAAGGAGTACAAGTGC
      K   V   S   N   K   A     L   P   A   P   I   E     K   T   I   S   K   A
 703 AAGGTCTCCAACAAAGCC CTCCCAGCCCCCATCGAG AAAACCATCTCCAAAGCC
      K   G   Q   P   R   E     P   Q   V   Y   T   L     P   P   S   R   E   E
 757 AAAGGGCAGCCCCGAGAA CCACAGGTGTACACCCTG CCCCCATCCCGGGAGGAG
      M   T   K   N   Q   V     S   L   T   C   L   V     K   G   F   Y   P   S
 811 ATGACCAAGAACCAGGTC AGCCTGACCTGCCTGGTC AAAGGCTTCTATCCCAGC
      D   I   A   V   E   W     E   S   N   G   Q   P     E   N   N   Y   K   T
 865 GACATCGCCGTGGAGTGG GAGAGCAATGGGCAGCCG GAGAACAACTACAAGACC
      T   P   P   V   L   D     S   D   G   S   F   F     L   Y   S   K   L   T
 919 ACGCCTCCCGTGCTGGAC TCCGACGGCTCCTTCTTC CTCTATAGCAAGCTCACC
      V   D   K   S   R   W     Q   Q   G   N   V   F     S   C   S   V   M   H
 973 GTGGACAAGAGCAGGTGG CAGCAGGGGAACGTCTTC TCATGCTCCGTGATGCAT
      E   A   L   H   N   H     Y   T   Q   K   S   L     S   L   S   P   G   K
1027 GAGGCTCTGCACAACCAC TACACGCAGAAGAGCCTC TCCCTGTCTCCGGGTAAA
      *
1081 TGA
```

US 12,186,370 B1

ACTRIIB LIGAND TRAP COMPOSITIONS AND USES THEREOF

1. CROSS-REFERENCE TO RELATED APPLICATIONS

This application claims the benefit of U.S. Provisional Patent Application No. 63/110,331, filed Nov. 5, 2020, which is incorporated by reference herein in its entirety.

2. SEQUENCE LISTING

This application incorporates by reference in its entirety the Computer Readable Form (CRF) of a Sequence Listing in ASCII text format submitted herewith. The Sequence Listing text file submitted herewith entitled "14247-598-999_SEQ_LISTING.TXT" was created on Oct. 29, 2021, and is 13,825 bytes in size.

3. INTRODUCTION

The present application relates to recombinant fusion proteins consisting of the extracellular domain (ECD) of human activin receptor IIB (ActRIIB) linked to a constant domain of an immunoglobulin, wherein the protein acts as an ActRIIB ligand trap, and compositions of the same comprising particular sequence variants, e.g., that arise during manufacture. The present application further relates to uses of such recombinant fusion proteins in treatment of various diseases.

4. BACKGROUND

Myelodysplastic syndromes (MDS) are a spectrum of hematologic malignancies characterized pathologically by the presence of morphologic dysplasia and clinically by bone marrow failure resulting in persistent and progressive cytopenias. There is considerable variation in both the clinical manifestation and severity of individual disorders within this group, ranging from the relatively mild and painless condition of refractory anemia (RA) to the much more severe refractory anemia with an excess of blasts (RAEB) that often progresses to acute leukemia (Heaney et al., N Engl J Med, 340 (21): 1649-60 (1999)). The current treatment algorithm is based predominantly on risk stratification using the International Prognostic Scoring System (IPSS) (Greenberg et al., Blood, 89 (6): 2079-2088 (1997), and Erratum in Blood, 91:110 (1998)). In subjects with low- or intermediate-1 (int-1) risk groups by IPSS, the goal of treatment is alleviation of cytopenias (Komrokji et al., Semin Oncol., 38 (5): 648-57 (2011)). Subjects with MDS can be categorized into 1 of 5 risk groups (very low, low, intermediate, high, and very high) according to the International Prognostic Scoring System-Revised (IPSS-R) based on cytogenetics, hemoglobin (Hgb), platelet and absolute neutrophil count (ANC) levels, and bone marrow (BM) blast percentages obtained at diagnosis. See, e.g., Greenberg et al., Blood, 120 (12): 2454-2465 (2012)). The five risk groups show significantly different risk of progression to acute myeloid leukemia (AML) and overall survival (OS). The median survival rate is 8.8 years for subjects with low risk MDS and is as short as 0.8 years for very high-risk MDS (Greenberg et al., Blood, 120 (12): 2454-2465 (2012)).

More than 90% of subjects diagnosed with MDS will have anemia during the course of their disease; and 30%-50% of subjects will be transfusion-dependent. Red blood cell (RBC) transfusion dependence is an independent adverse prognostic factor in MDS (Komrokji et al., Semin Oncol, 38 (5): 648-57 (2011)).

Options for treating anemia in lower-risk MDS are limited. Erythroid-stimulating agents (ESAs) offer response rates of 20%-40%. The use of ESAs (ie, recombinant erythropoietin [EPO] or darbepoetin [DAR]) is the standard of care for low and intermediate IPSS risk patients with symptomatic anemia and an endogenous serum erythropoietin (sEPO) level <500 IU/L and is recommended by European and United States (US) treatment guidelines. The use of granulocyte-colony stimulating factor (G-CSF) may be employed as needed but is not required, although in some cases it may further improve the efficacy of the ESA (Fenaux et al., Annals of Oncology, 25 (Suppl 3): iii57-iii69 (2014); Malcovati et al., Blood, 122 (17): 2943-64 (2013)). The European guidance also recommends the use of ESAs for patients who have a low RBC transfusion burden (<2 units/month) and/or an endogenous sEPO levels ≤500 IU/L (Fenaux et al., Annals of Oncology 25 (Suppl 3): iii57-iii69 (2014); Malcovati et al., Blood, 122 (17): 2943-64 (2013)). However, major favorable prognostic factors for response to ESAs are a low or no RBC transfusion requirement (<2 units/month) and an endogenous sEPO level <500 IU/L (Fenaux et al., Blood, 121 (21): 4280-6 (2013)). Responses to ESAs are best in patients with low endogenous levels (e.g., <500 IU/L) of sEPO, normal blast counts and lower IPSS/World Health Organization (WHO) Prognostic Scoring System (WPSS) scores (Hellstrom-Lindberg et al., Br J Haematol, 120 (6): 1037-46 (2003); Santini, V., Oncologist, 16 (Suppl 3): 35-42 (2011)).

Two related type II receptors, ActRIIA and ActRIIB, have been identified as the type II receptors for activins (Mathews and Vale, Cell, 65:973-982 (1991); Attisano et al., Cell, 68:97-108 (1992)). Besides activins, ActRIIA and ActRIIB can biochemically interact with several other TGF-beta family proteins, including BMP7, Nodal, GDF8, and GDF11 (Yamashita et al., J. Cell Biol., 130:217-226 (1995); Lee and McPherron, Proc. Natl. Acad. Sci., 98:9306-9311 (2001); Yeo and Whitman, Mol. Cell, 7:949-957 (2001); Oh et al., Genes Dev., 16:2749-54 (2002)).

ActRIIB ligand traps and uses thereof are described in, e.g., International Patent Application No. PCT/US09/004659 and International Patent Application No. PCT/US2010/045509.

5. SUMMARY OF THE INVENTION

Provided herein are polypeptides, ActRIIB-Fc fusion proteins, compositions comprising an ActRIIB-Fc fusion protein, compositions comprising a plurality of ActRIIB-Fc fusion proteins, pharmaceutical formulations comprising Product 1, and compositions comprising a plurality of polypeptides. Also provided herein are methods of manufacturing a plurality of ActRIIB-Fc fusion proteins in vitro and methods of determining whether a plurality of ActRIIB-Fc fusion proteins produced in vitro may be accepted or rejected for further use. Also provided herein are dosage forms comprising Product 1 and methods of treating a blood-related disorder in a subject.

In one aspect, provide herein are polypeptides. In some embodiments, provided is a polypeptide consisting of the amino acid sequence of SEQ ID NO:1.

In some embodiments, provided is a polypeptide comprising an amino acid sequence consisting of the sequence of SEQ ID NO:1.

In another aspect, provided herein are ActRIIB-Fc fusion proteins. In some embodiments, provided is an ActRIIB-Fc fusion protein comprising the amino acid sequence of SEQ ID NO:1, wherein said ActRIIB-Fc fusion protein lacks a C-terminal lysine, and wherein the protein comprises one or more of the following changes to said amino acid sequence: a. amidation of the C-terminal-most proline of SEQ ID NO:1; b. substitution of the N-terminal glutamate of SEQ ID NO: 1 with pyroglutamate; c. deamidation of one or more asparagine residues of SEQ ID NO: 1; d. isomerization of one or more aspartic acid residues of SEQ ID NO: 1; or e. oxidation of one or more methionine residues of SEQ ID NO:1.

In some embodiment, provided is an ActRIIB-Fc fusion protein comprising the amino acid sequence of SEQ ID NO:2, wherein the protein comprises one or more of the following changes to said amino acid sequence: a. Deletion of the C-terminal lysine of SEQ ID NO:2; b. amidation of the C-terminal-most proline of SEQ ID NO:2; c. substitution of the N-terminal glutamate of SEQ ID NO:2 with pyroglutamate; d. deamidation of one or more asparagine residues of SEQ ID NO:2; e. isomerization of one or more aspartic acid residues of SEQ ID NO: 2; or f. oxidation of one or more methionine residues of SEQ ID NO: 1.

In some embodiment, provided is an ActRIIB-Fc fusion protein comprising the amino acid sequence of SEQ ID NO:1, wherein said ActRIIB-Fc fusion protein lacks a C-terminal lysine, and wherein the protein comprises one or more of the following changes to said amino acid sequence: a. amidation of the C-terminal-most proline of SEQ ID NO: 1; b. substitution of the N-terminal glutamate of SEQ ID NO:1 with pyroglutamate; c. deamidation of asparagine residues 203, 249, 272 and/or 277 of SEQ ID NO:1; d. isomerization of aspartic acid residues 55, 56, 57, 168 and/or 289 of SEQ ID NO: 1; or e. oxidation of methionine residues 140, 246 and/or 316 of SEQ ID NO:1.

In some embodiment, provided is an ActRIIB-Fc fusion protein comprising the amino acid sequence of SEQ ID NO:2, wherein the protein comprises one or more of the following changes to said amino acid sequence: a. deletion of the C-terminal lysine of SEQ ID NO:2; b. amidation of the C-terminal-most proline of SEQ ID NO:2; c. substitution of the N-terminal glutamate of SEQ ID NO:2 with pyroglutamate; d. deamidation of asparagine residues 203, 249, 272 and/or 277 of SEQ ID NO:2; e. isomerization of aspartic acid residues 55, 56, 57, 168 and/or 289 of SEQ ID NO:2; or f. oxidation of methionine residues 140, 246 and/or 316 of SEQ ID NO: 2.

In another aspect, provide herein are compositions comprising an ActRIIB-Fc fusion protein. In some embodiments, provided is a composition comprising an ActRIIB-Fc fusion protein comprising the amino acid sequence of SEQ ID NO:1, wherein the composition comprises fusion proteins having one or more of the following changes to said amino acid sequence in the following amounts: a. at least 95% of said fusion proteins in said composition lack a C-terminal lysine; b. the C-terminal-most proline of SEQ ID NO: 1 is amidated in no more than 2.9% of said fusion proteins; c. the N-terminal glutamate of SEQ ID NO:1 is substituted with pyroglutamate in no more than 1.1% of said fusion proteins; d. one or more asparagine residues of SEQ ID NO: 1 are deamidated in no more than 3.9% of said fusion proteins; e. one or more aspartic acid residues of SEQ ID NO: 1 are isomerized in no more than 0.6% of said fusion proteins; or f. one or more methionine residues of SEQ ID NO: 1 are oxidized in no more than 1.2% of said fusion proteins.

In some embodiments, provided is a composition comprising an ActRIIB-Fc fusion protein comprising the amino acid sequence of SEQ ID NO:2, wherein the composition comprises fusion proteins having one or more of the following changes to said amino acid sequence in the following amounts: a. at least 95% of said fusion proteins in said composition lack the C-terminal lysine of SEQ ID NO: 2; b. the C-terminal-most proline of SEQ ID NO:2 is amidated in no more than 2.9% of said fusion proteins; c. the N-terminal glutamate of SEQ ID NO: 2 is substituted with pyroglutamate in no more than 1.1% of said fusion proteins; d. one or more asparagine residues of SEQ ID NO:2 are deamidated in no more than 3.9% of said fusion proteins; e. one or more aspartic acid residues of SEQ ID NO:2 are isomerized in no more than 0.6% of said fusion proteins; or f. one or more methionine residues of SEQ ID NO:2 are oxidized in no more than 1.2% of said fusion proteins.

In some embodiments, provided is a composition comprising an ActRIIB-Fc fusion protein comprising the amino acid sequence of SEQ ID NO:1, wherein said ActRIIB-Fc fusion protein lacks a C-terminal lysine, and wherein the composition comprises fusion proteins having one or more of the following changes to said amino acid sequence in the following amounts: a. the C-terminal-most proline of SEQ ID NO: 1 is amidated in 2.0%-2.9% of said fusion proteins; b. the N-terminal glutamate of SEQ ID NO:1 is substituted with pyroglutamate in 0.9%-1.1% of said fusion proteins; c. one or more asparagine residues of SEQ ID NO: 1 are deamidated in 0.6%-6.1% of said fusion proteins; d. one or more aspartic acid residues of SEQ ID NO: 1 are isomerized in 0.4%-0.6% of said fusion proteins; or e. one or more methionine residues of SEQ ID NO: 1 are oxidized in 0.2%-1.2% of said fusion proteins.

In some embodiments, provided is a composition comprising an ActRIIB-Fc fusion protein comprising the amino acid sequence of SEQ ID NO:2, wherein the composition comprises fusion proteins having one or more of the following changes to said amino acid sequence in the following amounts: a. the C-terminal lysine of SEQ ID NO:2 is deleted in at least 95% of said fusion proteins; b. the C-terminal-most proline of SEQ ID NO:2 is amidated in 2.0%-2.9% of said fusion proteins; c. the N-terminal glutamate of SEQ ID NO:2 is substituted with pyroglutamate in 0.9%-1.1% of said fusion proteins; d. one or more asparagine residues of SEQ ID NO:2 are deamidated in 0.6%-6.1% of said fusion proteins; e. one or more aspartic acid residues of SEQ ID NO:2 are isomerized in 0.4%-0.6% of said fusion proteins; or f. one or more methionine residues of SEQ ID NO:2 are oxidized in 0.2%-1.2% of said fusion proteins.

In another aspect, provide herein are compositions comprising a plurality of ActRIIB-Fc fusion protein. In some embodiments, provided is a composition comprising a plurality of ActRIIB-Fc fusion proteins comprising the amino acid sequence of SEQ ID NO:1, wherein the plurality of fusion proteins comprises fusion proteins having one or more of the following changes to said amino acid sequence in the following amounts: a. the C-terminal lysine of 95%-95.4% of said fusion proteins in said composition are deleted; b. the C-terminal-most proline of SEQ ID NO: 1 is amidated in 2.0%-2.9% of said fusion proteins; c. the N-terminal glutamate of SEQ ID NO:1 is substituted with pyroglutamate in 0.9%-1.1% of said fusion proteins; d. asparagine 203 of SEQ ID NO: 1 is deamidated in 3.6%-3.9% of said fusion proteins; e. asparagine 249 of SEQ ID NO: 1 is deamidated in 0.6% of said fusion proteins; f. asparagine 272/277 of SEQ ID NO: 1 are deamidated in 5.2%-6.1% of said fusion proteins; g. aspartic acid residues 55, 56 and/or 57 of SEQ ID NO: 1 are isomerized in 0.5%-0.6% of said fusion proteins; h. aspartic acid residue 168 of SEQ ID NO: 1 is isomerized in 0.4% of said fusion proteins; i. aspartic acid residue 289 of SEQ ID NO: 1 is isomerized in 0.4% of said fusion proteins; j. methionine residue 140 of SEQ ID NO: 1 is oxidized in 1.1%-1.2% of said fusion proteins; k. methionine residue 246 of SEQ ID NO: 1 is oxidized in 0.2%-0.3% of said fusion proteins; or l. methionine residue 316 of SEQ ID NO: 1 is oxidized in 0.6%-0.8% of said fusion proteins.

In some embodiments, provided is a composition comprising a plurality of ActRIIB-Fc fusion proteins comprising the amino acid sequence of SEQ ID NO:2, wherein the plurality of fusion proteins comprises fusion proteins having one or more of the following changes to said amino acid sequence in the following amounts: a. the C-terminal lysine of 95%-95.4% of said SEQ ID NO:2 in said composition are deleted; b. the C-terminal-most proline of SEQ ID NO:2 is amidated in 2.0%-2.9% of said fusion proteins; c. the N-terminal glutamate of SEQ ID NO:2 is substituted with pyroglutamate in 0.9%-1.1% of said fusion proteins; d. asparagine 203 of SEQ ID NO: 2 is deamidated in 3.6%-3.9% of said fusion proteins; e. asparagine 249 of SEQ ID NO:2 is deamidated in 0.6% of said fusion proteins; f. asparagine 272/277 of SEQ ID NO:2 are deamidated in 5.2%-6.1% of said fusion proteins; g. aspartic acid residues 55, 56 and/or 57 of SEQ ID NO:2 are isomerized in 0.5%-0.6% of said fusion proteins; h. aspartic acid residue 168 of SEQ ID NO:2 is isomerized in 0.4% of said fusion proteins; i. aspartic acid residue 289 of SEQ ID NO:2 is isomerized in 0.4% of said fusion proteins; j. methionine residue 140 of SEQ ID NO: 2 is oxidized in 1.1%-1.2% of said fusion proteins; k. methionine residue 246 of SEQ ID NO: 2 is oxidized in 0.2%-0.3% of said fusion proteins; or l. methionine residue 316 of SEQ ID NO: 2 is oxidized in 0.6%-0.8% of said fusion proteins.

In another aspect, provide herein are pharmaceutical formulations comprising Product 1. In some embodiments, provided is a pharmaceutical formulation comprising Product 1 wherein any heterogeneity is within the following ranges:

N-terminal pyroE: 0.9-1.1%
C-terminal Pro amidation: 2.0-2.9%
Asn203 deamidation: 3.6-3.9%
Asn249 deamidation: 0.6-0.6%
Asn272/277 deamidation: 5.2-6.1%
Asp55/56/57 isomerization: 0.5-0.6%
Asp168 isomerization: 0.4-0.4%
Asp289 isomerization: 0.4-0.4%
Met140 oxidation: 1.1-1.2%
Met246 oxidation: 0.2-0.3%
Met316 oxidation: 0.6-0.8%
Lys134/136 glycation: <0.3-0.4%
Lys208/210/214 glycation: 0.3-0.4%

In some embodiments, provided is a pharmaceutical formulation comprising Product 1 wherein the Pro-to-Ala sequence variant is less than 0.3%.

In some embodiments, provided is a polypeptide comprising the amino acid sequence of SEQ ID NO: 1 and one or more N-linked glycosylations.

In some embodiments, provided is a polypeptide comprising the amino acid sequence of SEQ ID NO:1 and one or more O-linked glycosylations.

In another aspect, provide herein are compositions comprising a plurality of polypeptides. In some embodiments, provided is a composition comprising a plurality of polypeptides comprising the amino acid sequence of SEQ ID NO:1, wherein the plurality of polypeptides, when digested to completion with trypsin endopeptidase, results in a trypsin peptide map essentially as shown in FIG. 4 or 5, wherein said peptides have been separated by reverse phase ultra performance liquid chromatography (RP-UPLC) using a C18 column with a gradient of acetonitrile in 0.05% trifluoroacetic acid (TFA) (v/v), monitoring of ultraviolet (UV) absorbance at 214 nm, and identification of peptides by inline mass spectrometry (MS) and tandem MS (MS/MS) analysis.

In some embodiments, provided is a composition comprising a plurality of polypeptides comprising the amino acid sequence of SEQ ID NO: 1, wherein the plurality of polypeptides results in a charge heterogeneity profile substantially as shown in FIG. 6, 7, 8 or 9 using imaged capillary isoelectrofocusing.

In some embodiments, provided is a polypeptide comprising amino acid SEQ ID NO: 1 wherein: a. the N-terminal glutamic acid is pyroglutamic acid (PCA or pyroE); b. the asparagine at 203 is deamidated; c. the asparagine at 249 is deamidated; d. the asparagine at 272/277 is deamidated; e. the aspartic acid at 55/56/57 is isomerized; f. the aspartic acid at 168 is isomerized; g. the aspartic acid at 289 is isomerized; h. the methionine at 140 is oxidized; i. the methionine at 246 is oxidized; j. the lysine at 134/136 is glycated; or k. the lysine at 208/210/214 is glycated.

In another aspect, provide herein are methods of manufacturing ActRIIB-Fc fusion proteins in vitro. In some embodiments, provided is a method of manufacturing ActRIIB-Fc fusion proteins in vitro, comprising expressing a nucleic acid sequence that comprises a nucleic acid sequence that encodes SEQ ID NO: 1 to produce a plurality of fusion proteins comprising the sequence of SEQ ID NO: 1, wherein said plurality of fusion proteins comprises fusion proteins lacking a C-terminal lysine and having one or more of the following changes to said amino acid sequence in the following amounts: a. the C-terminal-most proline of SEQ ID NO:1 is amidated in 2.0%-2.9% of said fusion proteins; b. the N-terminal glutamate of SEQ ID NO:1 is substituted with pyroglutamate in 0.9%-1.1% of said fusion proteins; c. one or more asparagine residues of SEQ ID NO: 1 are deamidated in 0.6%-6.1% of said fusion proteins; d. one or more aspartic acid residues of SEQ ID NO: 1 are isomerized in 0.4%-0.6% of said fusion proteins; or e. one or more methionine residues of SEQ ID NO: 1 are oxidized in 0.2%-1.2% of said fusion proteins.

In some embodiments, provided is a method of manufacturing ActRIIB-Fc fusion proteins in vitro, comprising expressing a nucleic acid sequence that comprises a nucleic acid sequence that encodes SEQ ID NO:2 to produce a plurality of fusion proteins comprising the sequence of SEQ ID NO:2, wherein said plurality of fusion proteins comprises fusion proteins having one or more of the following changes to said amino acid sequence in the following amounts: a. the C-terminal lysine of SEQ ID NO:2 is deleted in at least 95% of said fusion proteins; b. the C-terminal-most proline of SEQ ID NO:2 is amidated in 2.0%-2.9% of said fusion proteins; c. the N-terminal glutamate of SEQ ID NO:2 is substituted with pyroglutamate in 0.9%-1.1% of said fusion proteins; d. one or more asparagine residues of SEQ ID NO:2 are deamidated in 0.6%-6.1% of said fusion proteins; e. one or more aspartic acid residues of SEQ ID NO: 2 are isomerized in 0.4%-0.6% of said fusion proteins; or f. one or more methionine residues of SEQ ID NO:2 are oxidized in 0.2%-1.2% of said fusion proteins.

In some embodiments, provided is a method of manufacturing ActRIIB-Fc fusion proteins in vitro, comprising expressing a nucleic acid sequence that comprises a nucleic acid sequence that encodes SEQ ID NO: 1 to produce a plurality of fusion proteins comprising the sequence of SEQ ID NO: 1, wherein said plurality of fusion proteins comprises fusion proteins lacking a C-terminal lysine and having one or more of the following changes to said amino acid sequence in the following amounts: a. the C-terminal lysine of 95%-95.4% of said fusion proteins in said composition are deleted; b. the C-terminal-most proline of SEQ ID NO: 1 is amidated in 2.0%-2.9% of said fusion proteins; c. the N-terminal glutamate of SEQ ID NO: 1 is substituted with pyroglutamate in 0.9%-1.1% of said fusion proteins; d. asparagine 203 of SEQ ID NO: 1 is deamidated in 3.6%-3.9% of said fusion proteins; e. asparagine 249 of SEQ ID NO:1 is deamidated in 0.6% of said fusion proteins; f. asparagine 272/277 of SEQ ID NO: 1 are deamidated in 5.2%-6.1% of said fusion proteins; g. aspartic acid residues 55, 56 and/or 57 of SEQ ID NO: 1 are isomerized in 0.5%-0.6% of said fusion proteins; h. aspartic acid residue 168 of SEQ ID NO: 1 is isomerized in 0.4% of said fusion proteins; i. aspartic acid residue 289 of SEQ ID NO: 1 is isomerized in 0.4% of said fusion proteins; j. methionine residue 140 of SEQ ID NO: 1 is oxidized in 1.1%-1.2% of said fusion proteins; k. methionine residue 246 of SEQ ID NO: 1 is oxidized in 0.2%-0.3% of said fusion proteins; or l. methionine residue 316 of SEQ ID NO: 1 is oxidized in 0.6%-0.8% of said fusion proteins.

In some embodiments, provided is a method of manufacturing a plurality ActRIIB-Fc fusion proteins in vitro, comprising expressing a nucleic acid sequence that comprises a nucleic acid sequence that encodes SEQ ID NO:2 to produce a plurality of fusion proteins comprising the sequence of SEQ ID NO:2, wherein said plurality of fusion proteins comprises fusion proteins having one or more of the following changes to said amino acid sequence in the following amounts: a. the C-terminal lysine of 95%-95.4% of SEQ ID NO:2 are deleted; b. the C-terminal-most proline of SEQ ID NO:2 is amidated in 2.0%-2.9% of said fusion proteins; c. the N-terminal glutamate of SEQ ID NO:2 is substituted with pyroglutamate in 0.9%-1.1% of said fusion proteins; d. asparagine 203 of SEQ ID NO:2 is deamidated in 3.6%-3.9% of said fusion proteins; e. asparagine 249 of SEQ ID NO:2 is deamidated in 0.6% of said fusion proteins; f. asparagine 272/277 of SEQ ID NO:2 are deamidated in 5.2%-6.1% of said fusion proteins; g. aspartic acid residues 55, 56 and/or 57 of SEQ ID NO:2 are isomerized in 0.5%-0.6% of said fusion proteins; h. aspartic acid residue 168 of SEQ ID NO:2 is isomerized in 0.4% of said fusion proteins; i. aspartic acid residue 289 of SEQ ID NO:2 is isomerized in 0.4% of said fusion proteins; j. methionine residue 140 of SEQ ID NO:2 is oxidized in 1.1%-1.2% of said fusion proteins; k. methionine residue 246 of SEQ ID NO:2 is oxidized in 0.2%-0.3% of said fusion proteins; or l. methionine residue 316 of SEQ ID NO:2 is oxidized in 0.6%-0.8% of said fusion proteins.

In some embodiments, provided is a method of manufacturing a plurality of ActRIIB-Fc fusion proteins in vitro, wherein said plurality of fusion proteins may be accepted or rejected for further use, comprising expressing a nucleic acid sequence that comprises a nucleic acid sequence that encodes SEQ ID NO: 1 to produce a plurality of fusion proteins comprising the sequence of SEQ ID NO: 1, and determining that said plurality of fusion proteins comprises fusion proteins having one or more of the following changes to said amino acid sequence in the following amounts: a. The C-terminal lysine is deleted in 95.0%-95.4% of said fusion proteins; b. the C-terminal-most proline of SEQ ID NO: 1 is amidated in 2.0%-2.9% of said fusion proteins; c. the N-terminal glutamate of SEQ ID NO: 1 is substituted with pyroglutamate in 0.9%-1.1% of said fusion proteins; d. one or more asparagine residues of SEQ ID NO: 1 are deamidated in 0.6%-6.1% of said fusion proteins; e. one or more aspartic acid residues of SEQ ID NO: 1 are isomerized in 0.4%-0.6% of said fusion proteins; or f. one or more methionine residues of SEQ ID NO: 1 are oxidized in 0.2%-1.2% of said fusion proteins; wherein if any of said changes a-f are greater or less than said amounts, said plurality of fusion proteins is rejected for further use, and wherein if all of said changes a-f are within said amounts, said plurality of fusion proteins is accepted for further use.

In some embodiments, provided is a method of manufacturing a plurality of ActRIIB-Fc fusion proteins in vitro, wherein said plurality of fusion proteins may be accepted or rejected for further use, comprising expressing a nucleic acid sequence that comprises a nucleic acid sequence that encodes SEQ ID NO: 1 to produce a plurality of fusion proteins comprising the sequence of SEQ ID NO:1, wherein said plurality of fusion proteins comprises fusion proteins lacking a C-terminal lysine and having one or more of the following changes to said amino acid sequence in the following amounts: a. the C-terminal lysine of 95%-95.4% of said fusion proteins in said composition are deleted; b. the C-terminal-most proline of SEQ ID NO:1 is amidated in 2.0%-2.9% of said fusion proteins; c. the N-terminal glutamate of SEQ ID NO: 1 is substituted with pyroglutamate in 0.9%-1.1% of said fusion proteins; d. asparagine 203 of SEQ ID NO: 1 is deamidated in 3.6%-3.9% of said fusion proteins; e. asparagine 249 of SEQ ID NO:1 is deamidated in 0.6% of said fusion proteins; f. asparagine 272/277 of SEQ ID NO: 1 are deamidated in 5.2%-6.1% of said fusion proteins; g. aspartic acid residues 55, 56 and/or 57 of SEQ ID NO: 1 are isomerized in 0.5%-0.6% of said fusion proteins; h. aspartic acid residue 168 of SEQ ID NO: 1 is isomerized in 0.4% of said fusion proteins; i. aspartic acid residue 289 of SEQ ID NO: 1 is isomerized in 0.4% of said fusion proteins; j. methionine residue 140 of SEQ ID NO: 1 is oxidized in 1.1%-1.2% of said fusion proteins; k. methionine residue 246 of SEQ ID NO: 1 is oxidized in 0.2%-0.3% of said fusion proteins; or l. methionine residue 316 of SEQ ID NO: 1 is oxidized in 0.6%-0.8% of said fusion proteins; wherein if any of said changes a-l are greater or less than said amounts, said plurality of fusion proteins is rejected for further use, and wherein if all of said changes a-l are within said amounts, said plurality of fusion proteins is accepted for further use.

In another aspect, provide herein are methods of determining whether a plurality of ActRIIB-Fc fusion proteins produced in vitro may be accepted or rejected for further use. In some embodiments, provided is a method of determining whether a plurality of ActRIIB-Fc fusion proteins produced in vitro may be accepted or rejected for further use, comprising expressing a nucleic acid sequence that comprises a nucleic acid sequence that encodes SEQ ID NO: 1 to produce a plurality of fusion proteins comprising the sequence of SEQ ID NO:1, and determining whether said plurality of fusion proteins comprises fusion proteins having one or more of the following changes to said amino acid sequence in the following amounts: a. the C-terminal lysine is deleted in 95.0%-95.4% of said fusion proteins; b. the C-terminal-most proline of SEQ ID NO: 1 is amidated in 2.0%-2.9% of said fusion proteins; c. the N-terminal glutamate of SEQ ID NO: 1 is substituted with pyroglutamate in 0.9%-1.1% of said fusion proteins; d. one or more asparagine residues of SEQ ID NO: 1 are deamidated in 0.6%-6.1% of said fusion proteins; e. one or more aspartic acid residues of SEQ ID NO: 1 are isomerized in 0.4%-0.6% of said fusion proteins; or f. one or more methionine residues of SEQ ID NO: 1 are oxidized in 0.2%-1.2% of said fusion proteins; wherein if any of said changes a-f are greater or less than said amounts, said plurality of fusion proteins is rejected for further use, and wherein if all of said changes a-f are within said amounts, said plurality of fusion proteins is accepted for further use.

In some embodiments, provided is a method of determining whether a plurality of ActRIIB-Fc fusion proteins produced in vitro may be accepted or rejected for further use, comprising expressing a nucleic acid sequence that comprises a nucleic acid sequence that encodes SEQ ID NO: 1 to produce a plurality of fusion proteins comprising the sequence of SEQ ID NO: 1 and lacking a C-terminal lysine, and determining whether said plurality of fusion proteins comprises fusion proteins having one or more of the following changes to said amino acid sequence in the following amounts: a. the C-terminal lysine of 95%-95.4% of said fusion proteins in said composition are deleted; b. the C-terminal-most proline of SEQ ID NO: 1 is amidated in 2.0%-2.9% of said fusion proteins; c. the N-terminal glutamate of SEQ ID NO: 1 is substituted with pyroglutamate in 0.9%-1.1% of said fusion proteins; d. asparagine 203 of SEQ ID NO: 1 is deamidated in 3.6%-3.9% of said fusion proteins; e. asparagine 249 of SEQ ID NO:1 is deamidated in 0.6% of said fusion proteins; f. asparagine 272/277 of SEQ ID NO: 1 are deamidated in 5.2%-6.1% of said fusion proteins; g. aspartic acid residues 55, 56 and/or 57 of SEQ ID NO: 1 are isomerized in 0.5%-0.6% of said fusion proteins; h. aspartic acid residue 168 of SEQ ID NO: 1 is isomerized in 0.4% of said fusion proteins; i. aspartic acid residue 289 of SEQ ID NO: 1 is isomerized in 0.4% of said fusion proteins; j. methionine residue 140 of SEQ ID NO: 1 is oxidized in 1.1%-1.2% of said fusion proteins; k. methionine residue 246 of SEQ ID NO: 1 is oxidized in 0.2%-0.3% of said fusion proteins; or l. methionine residue 316 of SEQ ID NO: 1 is oxidized in 0.6%-0.8% of said fusion proteins; wherein if any of said changes a-l are greater or less than said amounts, said plurality of fusion proteins is rejected for further use, and wherein if all of said changes a-l are within said amounts, said plurality of fusion proteins is accepted for further use.

In another aspect, provide herein are dosage forms comprising Product 1. In some embodiments, provided is a dosage form comprising Product 1 wherein Product 1 is in a lyophilized form or in a liquid solution in a vial.

In some embodiments, the dosage form comprises about 15 mg, about 17.5 mg, about 20 mg, about 22.5 mg, about 25 mg, about 27.5 mg, about 30 mg, about 32.5 mg, about 35 mg, about 37.5 mg, about 40 mg, about 42.5 mg, about 45 mg, about 47.5 mg, about 50 mg, about 52.5 mg, about 55 mg, about 57.5 mg, about 60 mg, about 62.5 mg, about 65 mg, about 67.5 mg, about 70 mg, about 72.5 mg, about 75 mg, about 77.5 mg, about 80 mg, about 82.5 mg, about 85 mg, about 90 mg, about 92.5 mg, about 95 mg, about 97.5 mg or about 100 mg of Product 1.

In another aspect, provide herein are methods of treating a blood-related disorder in a subject. In some embodiments, provided is a method of treating a blood-related disorder in a subject wherein the method comprises administering to the subject the polypeptide, the ActRIIB-Fc fusion protein, the composition, the pharmaceutical formulation, or the dosage form provided herein.

6. BRIEF DESCRIPTION OF THE FIGURES

FIG. 1. Primary structure of Product 1 with key post-translational modifications shown.

FIG. 2. Restriction map of the Expression Vector 1 includes the open reading frame encoding SEQ ID NO:6.

FIG. 3. Trypsin peptide map profile of Product 1 DS batch A1. UV profile from retention times 0 through 50, and 50-100 are presented in top and bottom panel, respectively.

FIG. 4. Peptide map profiles for Product 1 DS batches A1, A2 and A3.

FIG. 5. Peptide map profiles for Product 1 DS batches A1, A4 and A5.

FIG. 6. icIEF analysis of Product 1 batch A1. Groupings for quantitative analysis are shown.

FIG. 7. icIEF analysis of batch A1 before and after treatment with sialidase.

FIG. 8. icIEF profiles for Product 1 batches A1, A2 and A3.

FIG. 9. icIEF profiles for Product 1 batches A1, A4 and A5.

FIG. 10 illustrates increase of isomerization of Asp residues in relation to potency loss under heat stress. A linear correlation between the Asp isomerization percentage and potency loss induced by heat stress was observed (r=−0.95).

FIGS. 11A and 11B illustrate increase of deamidation of Asn residues and low molecular weight species (LMWS) in relation to potency loss under high pH stress. FIG. 11A: A linear correlation between the Asn deamidation percentage and potency loss under high pH stress was observed (r=−0.75). FIG. 11B: A linear correlation between LMWS percentage measured by reduced CE-SDS and potency loss under high pH stress was also observed (r=−0.83).

FIGS. 12A and 12B illustrate increase of oxidation of Met residues at Met site 1 (Met140) and Met site 2 (Met316) in relation to FcRn binding loss under oxidation stress. FIG. 12A: A linear correlation between the percentage of oxidation of Met site 1 (Met140) and FcRn binding loss under oxidation stress was observed (r=−0.94). FIG. 12B: A linear correlation between the percentage of oxidation of Met site 2 (Met316) and FcRn binding loss under oxidation stress was also observed (r=−0.87).

Figure 15:
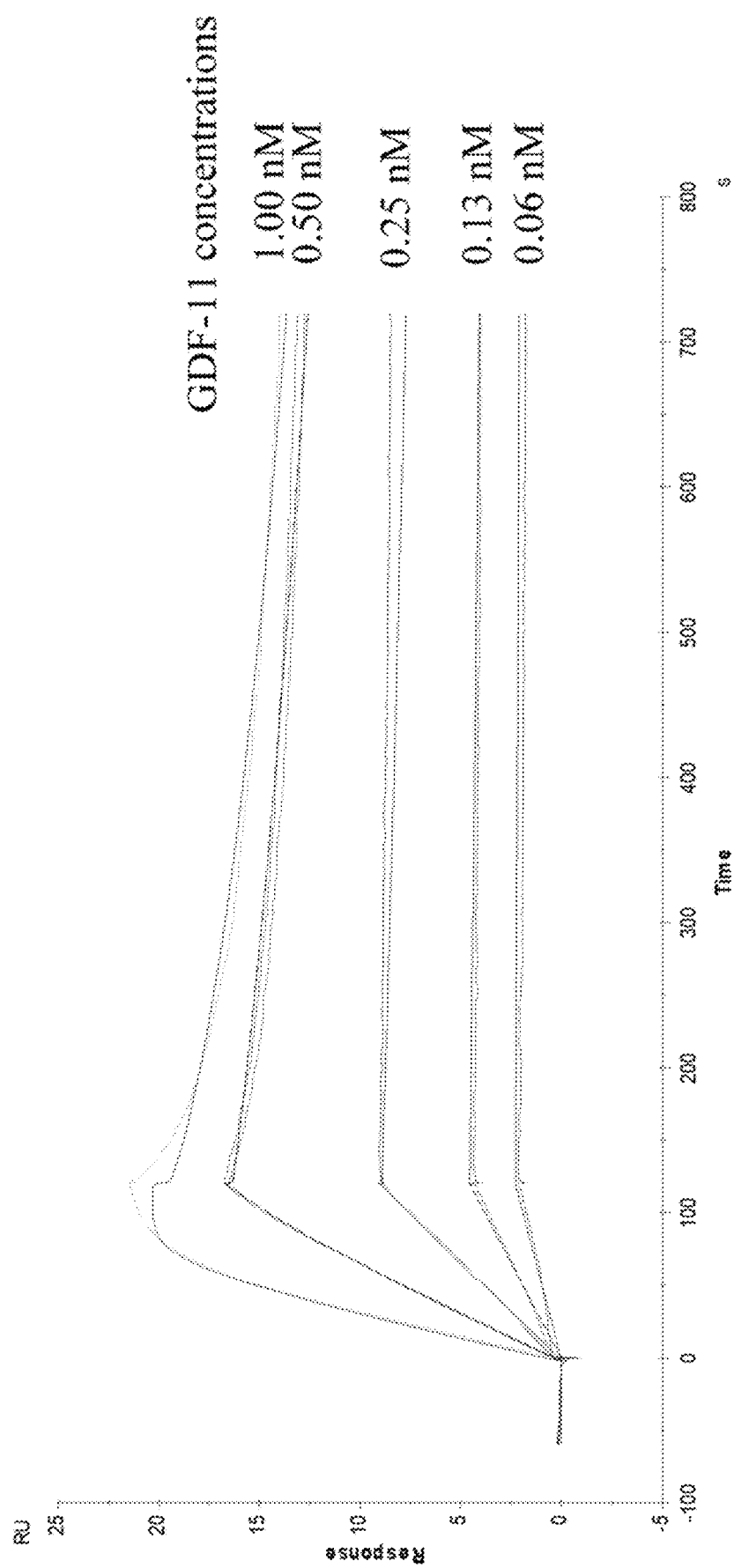

FIG. 15. Product 1 PRSA4 binding to human GDF-11.

Figure 16:
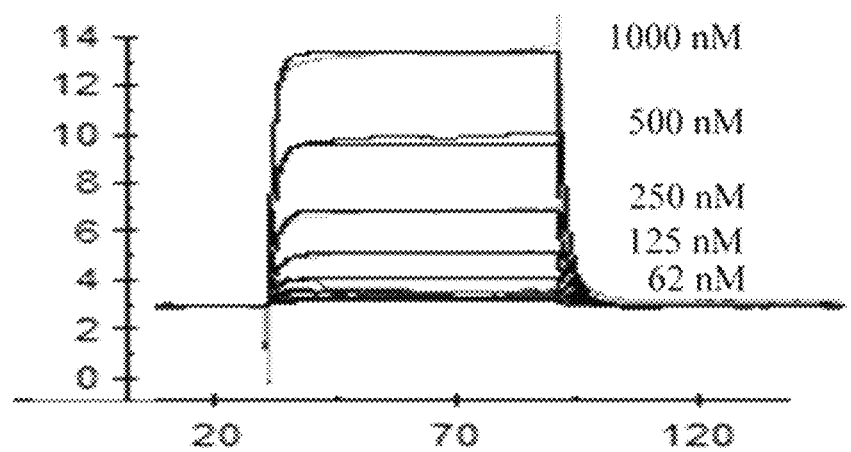

FIG. 16. Biacore sensogram for Product 1 binding to human FcRn.

Figure 17:
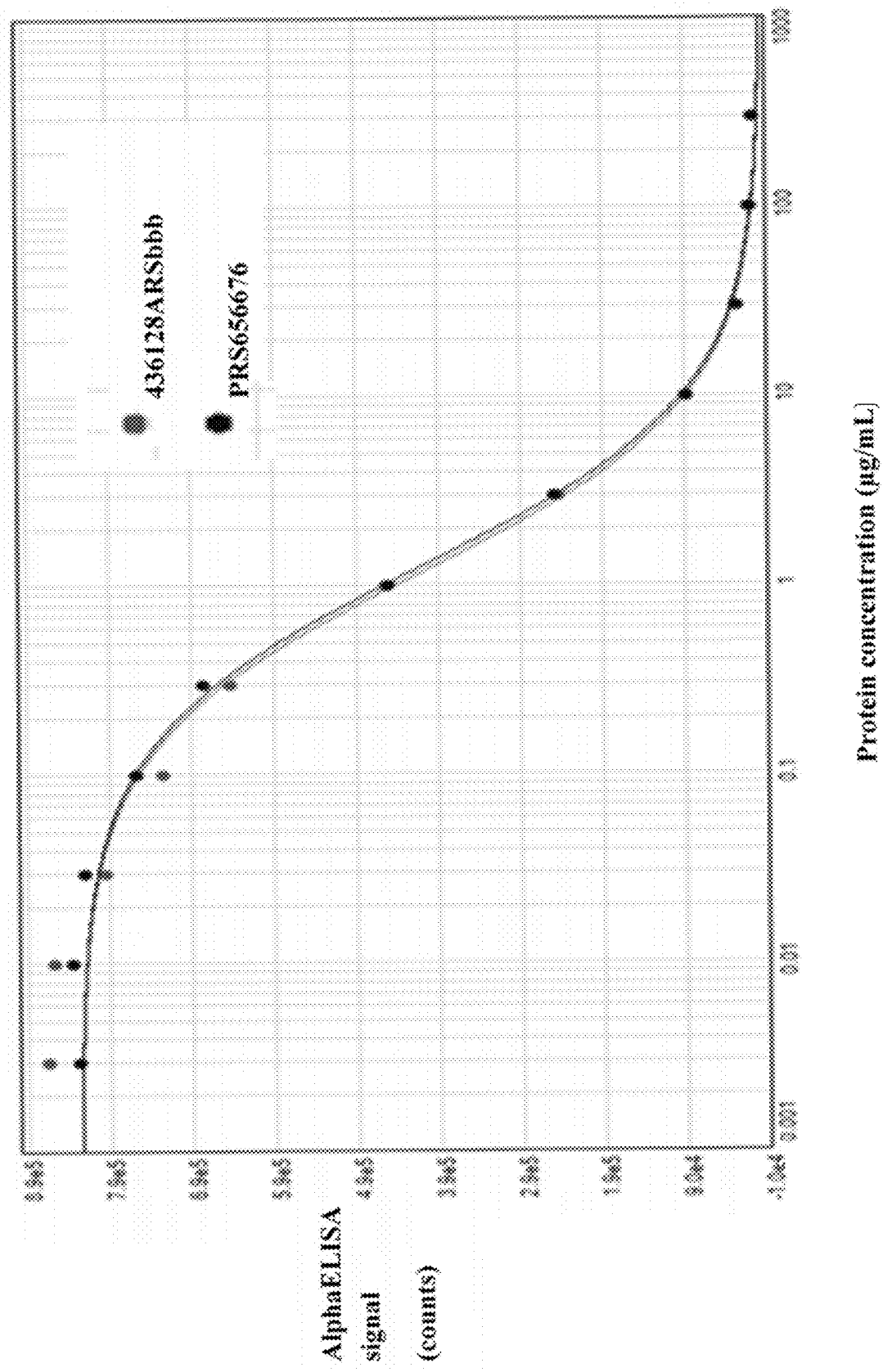

FIG. 17. Comparable binding of Product 1 lots to FcRn.

Figure 18C:
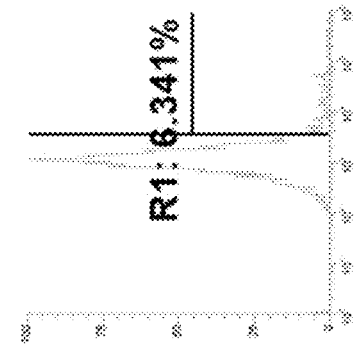
Figure 18B:
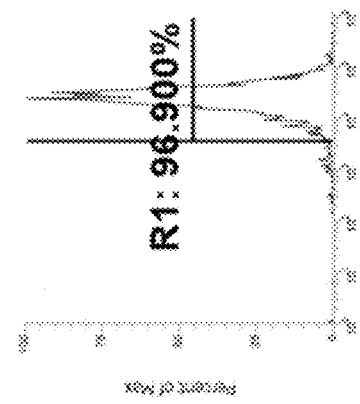
Figure 18A:
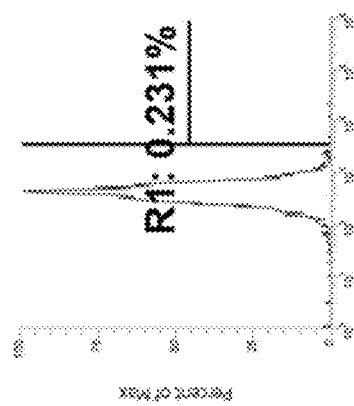
Figure 18F:
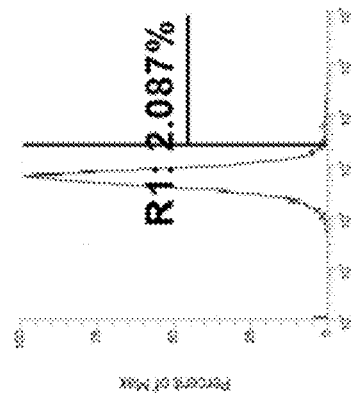
Figure 18E:
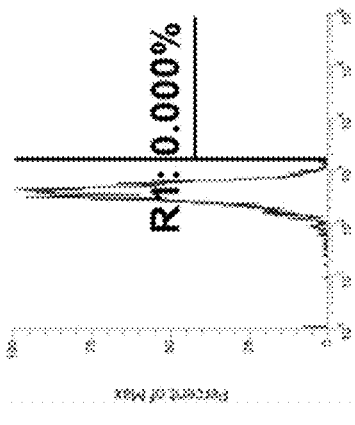
Figure 18D:
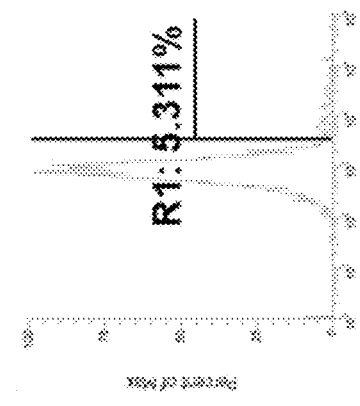
Figure 18G:
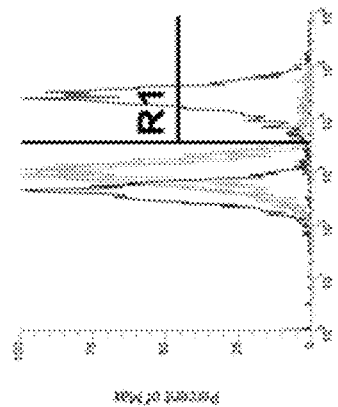
Figure 18H:
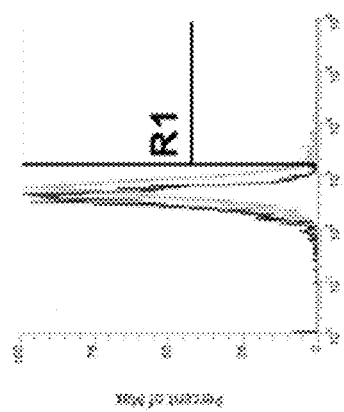
Figure 18I:
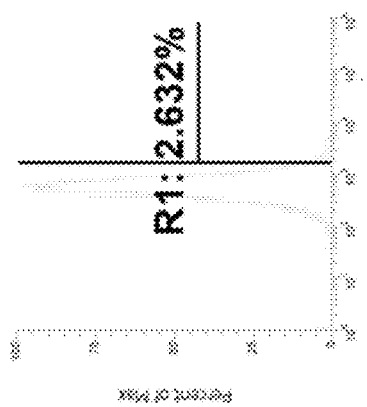
Figure 18J:
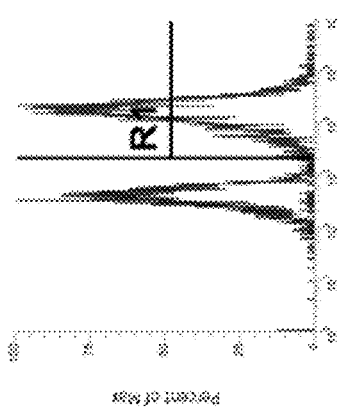
Figure 18K:
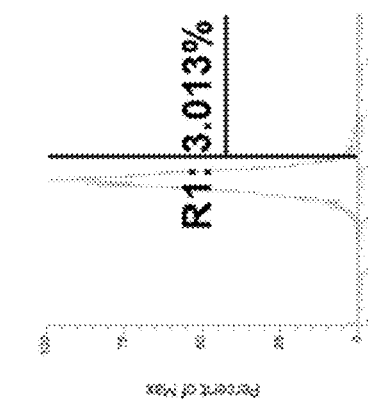
Figure 18L:
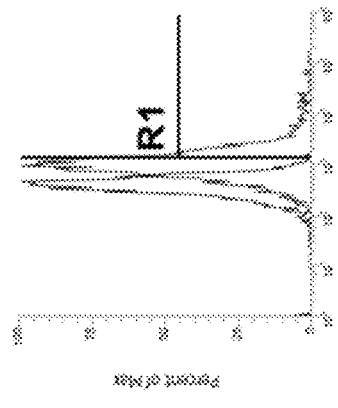

FIGS. 18A-18L. Product 1 does not bind to the cell surface or to GDF-11 bound to the cell surface. FIG. 18A shows isotype control. FIG. 18B shows that GDF-11 can be detected in complex with ActIIB receptor on the cell surface of the cell line used in the Product 1 bioassay when stained with an antibody to GDF-11. FIG. 18C shows that this is blocked if GDF-11 is pre-incubated with Product 1 lot PRSA4. FIG. 18D shows that Product 1 does not bind to the cell surface of the cells either in the absence of GDF-11. FIG. 18E shows isotype control antibody. Product 1 is not detected in complex with the A204-CAGA 12-Luc cell line that has been pre-incubated with high, medium, or low concentrations of GDF-11, as shown in FIG. 18F, FIG. 18G, and FIG. 18H, respectively. FIG. 18I shows overlay of FIG. 18A and FIG. 18B. FIG. 18J shows overlay of FIG. 18B and FIG. 18C. FIG. 18K shows overlay of FIG. 18D and FIG. 18E. FIG. 18L shows overlay of FIG. 18F, FIG. 18G, and FIG. 18H.

Figure 19:
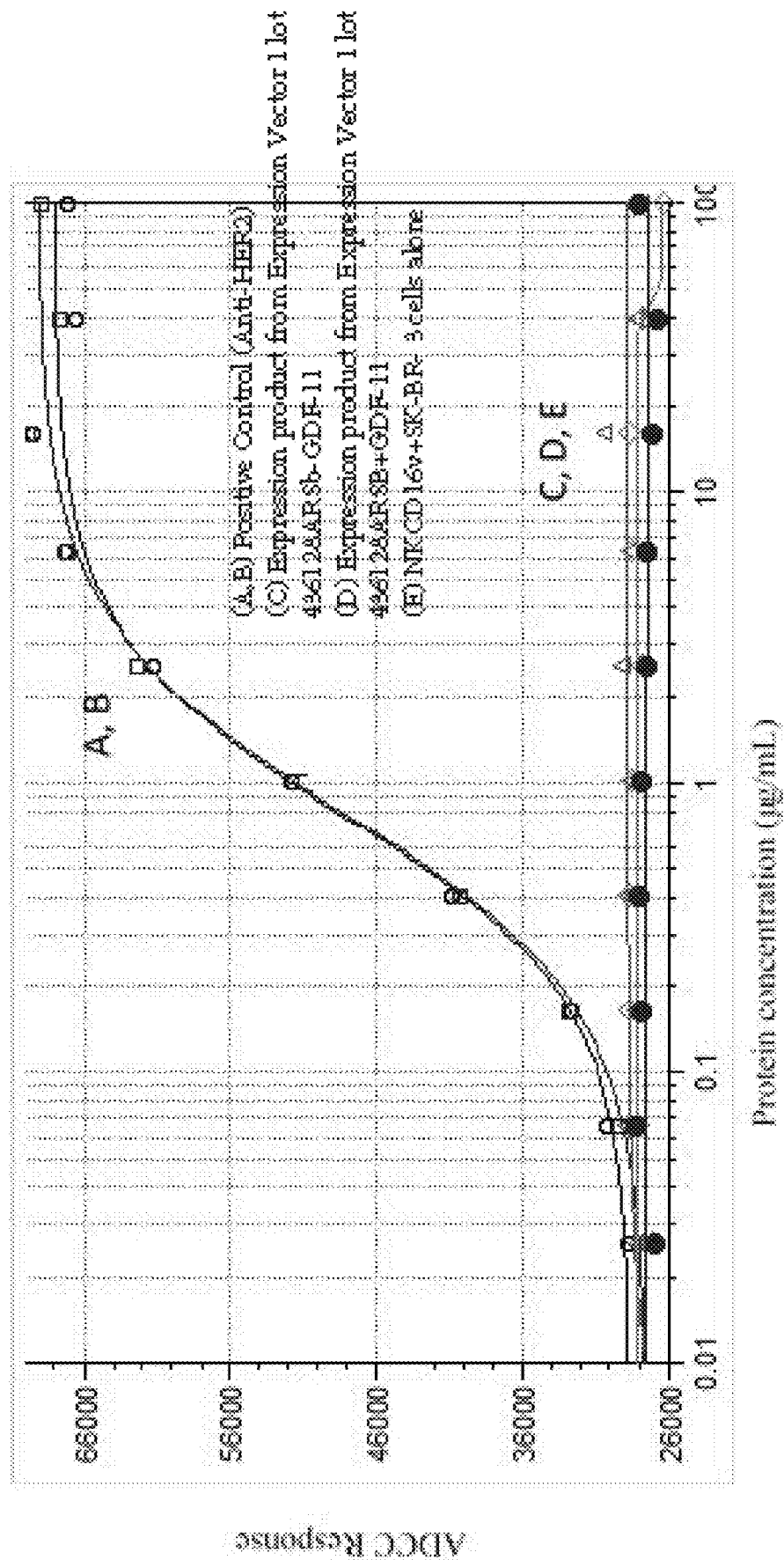

FIG. 19. Product 1 does not induce ADCC.

Figure 20:
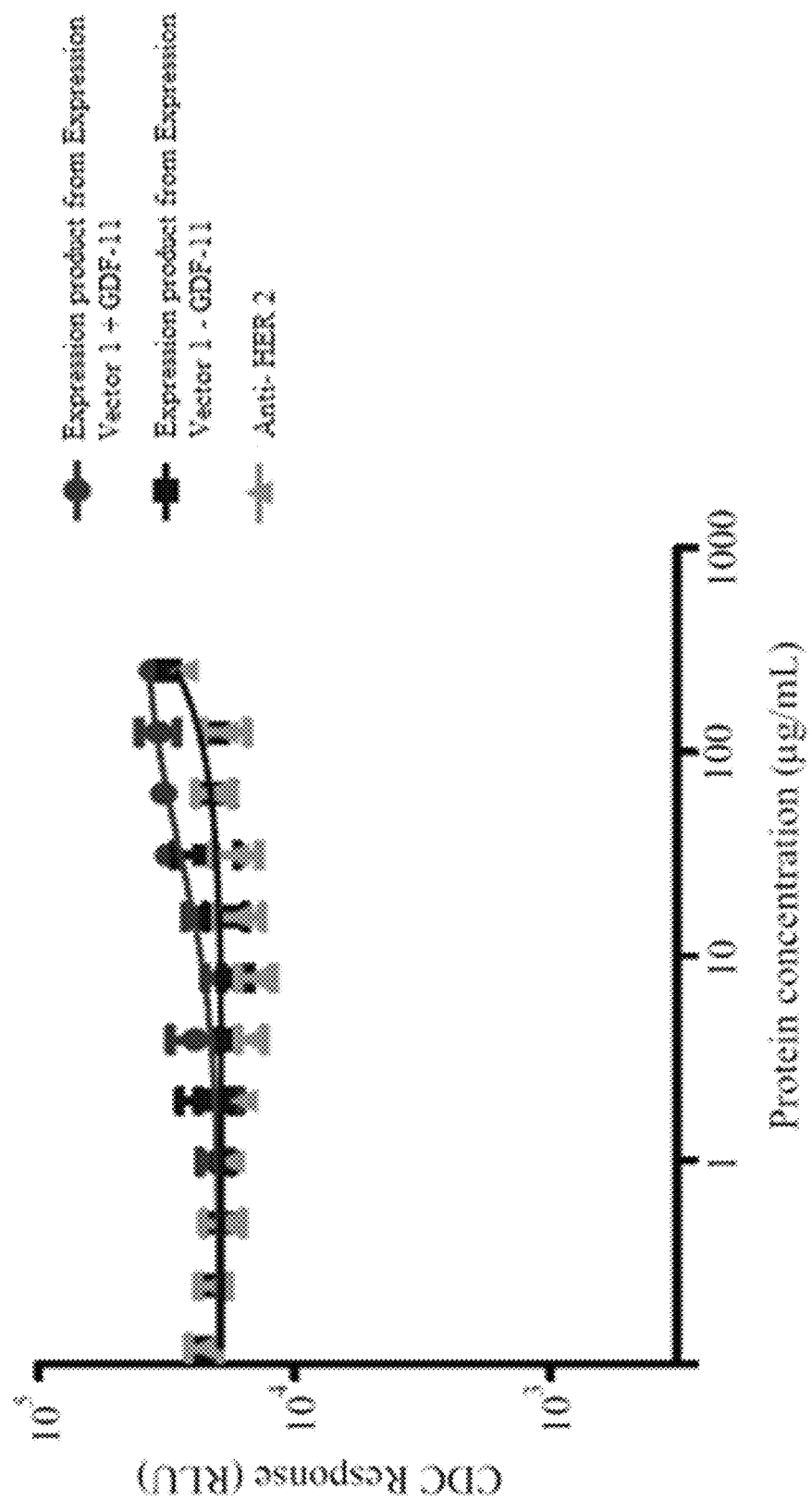

FIG. 20. Product 1 does not induce CDC.

FIG. 21. Coding sequence of Product 1 (SEQ ID NOs: 6 and 7). Nucleic acid sequence positions 1-72 encode the TPA signal peptide sequence.

7. TERMS AND ABBREVIATIONS

As used herein, "ActRII" refers to activin receptor type II.

As used herein, "ActRIIA" refers to activin receptor type IIA. See, for example, Mathews and Vale, 1991, Cell, 65:973-982. GenBank™ accession number NM_001278579.1 provides an exemplary human ActRIIA nucleic acid sequence. GenBank™ accession number NP_001265508.1 provides an exemplary human ActRIIA amino acid sequence.

As used herein, "ActRIIB" refers to activin receptor type IIB. See, for example, Attisano et al., Cell, 68:97-108 (1992). GenBank™ accession number NM_001106.3 provides an exemplary human ActRIIB nucleic acid sequence. GenBank™ accession number NP_001097.2 provides an exemplary human ActRIIB amino acid sequence.

As used herein, "ADCC" refers to antibody-dependent cellular cytotoxicity.

As used herein, "Amp" refers to ampicillin.

As used herein, "CDC" refers to complement-dependent cellular cytotoxicity.

As used herein, "CE-SDS (R & NR)" refers to capillary electrophoresis sodium dodecyl sulfate (reduced and nonreduced).

As used herein, "CHO" refers to Chinese Hamster Ovary cells.

As used herein, "CMV" refers to cytomegalovirus.

As used herein, "ColE1 ori" refers to colicin E1 origin of replication.

As used herein, "CTL" refers to C-terminal lysine.

As used herein, "CQA" refers to critical quality attribute.

As used herein, "DAR" refers to darbepoetin.

As used herein, "DHFR" refers to dihydrofolate reductase.

As used herein, "DS" refers to drug substance.

As used herein, "ECD" refers to extracellular domain.

As used herein, "ELISA" refers to enzyme-linked immunosorbent assay.

As used herein, "EPO" refers to erythropoietin.

As used herein, "Product 1" refers to a product resulting from expression from an opening reading frame with the nucleotide sequence of SEQ ID NO:7 or a degenerate version of SEQ ID NO:7 that encodes SEQ ID NO:1, and subsequent protein purification procedures.

As used herein, "G-CSF" refers to granulocyte colony-stimulating factor.

As used herein, "IU/L" refers to international unit per liter.

As used herein, "FcRn" refers to neonatal Fc receptor.

As used herein, "GDF8" refers to growth differentiation factor 8.

As used herein, "GDF11" refers to growth differentiation factor 11.

As used herein, "HMWS" refers to high molecular weight species.

As used herein, "ICH" refers to International Council for Harmonisation.

As used herein, "icIEF" refers to imaged capillary isoelectrofocusing.

As used herein, "IgG" refers to immunoglobulin G.

As used herein, "IgG1 Fc" refers to Immunoglobulin gamma-1 heavy chain constant region.

As used herein, "IRES" refers to internal ribosomal entry site.

As used herein, "LC-MS" refers to liquid chromatography mass spectrometry.

As used herein, "LMWS" refers to low molecular weight species.

As used herein, "MDS" refers to myelodysplastic syndromes.

As used herein, "MS" refers to mass spectrometry.

As used herein, "pI" refers to isoeletric point.

As used herein, "PPQ" refers to process performance qualification.

As used herein, "PTM" refers to post-translational modifications.

As used herein, "RA" refers to refractory anemia.

As used herein, "RAEB" refers to refractory anemia with an excess of blasts.

As used herein, "RBC" refers to red blood cells.

As used herein, "RP-UPLC" refers to reverse-phase ultra performance liquid chromatography.

As used herein, "SEC" refers to size-exclusion chromatography.

As used herein, "sEPO" refers to serum erythropoietin.

As used herein, "SPR" refers to Surface Plasmon Resonance.

As used herein, "SMAD2/3" refers to two proteins encoded by the SMAD gene, a family of proteins similar to the gene products of the *Drosophila* gene 'mothers against decapentaplegic' (Mad) and the *C. elegans* gene Sma.

As used herein, "SWFI" refers to sterile water for injection.

As used herein, "SV40 poly A" refers to simian virus 40 polyadenylation signal. As used herein, "SV40 ori/enhanger" refers to simian virus 40 origin/enhancer.

As used herein, "TBHP" refers to tert-butyl hydroperoxide.

As used herein, "TFA" refers to trifluroacetic acid.

As used herein, "TPA" refers to tissue plasminogen activator.

As used herein, "TGFβ" refers to transforming growth factor beta.

As used herein, "UV" refers to ultraviolet.

As used herein, "WCB2" refers to working cell bank two.

8. DETAILED DESCRIPTION OF THE INVENTION 8.1 Overview

Provided herein are compositions comprising a recombinant fusion protein comprising an extracellular domain (ECD) of human activin receptor IIB (ActRIIB) or derivatives thereof linked to a constant domain of an immunoglobulin, such as human IgG1 Fc domain. In a specific embodiment, provided herein is a polypeptide comprising an amino acid sequence consisting of SEQ ID NO: 1 (see Section 6.2). In certain embodiments, provided herein are polypeptides comprising the amino acid sequence of SEQ ID NO: 1 wherein at least one amino acid is modified as described in Section 6.2. In certain embodiments, such a fusion protein can act as an inhibitor of the ActRIIB signaling pathway. Also provided herein are methods of making the polypeptides of the invention (see Section 6.3). In certain, more specific, embodiments provided herein is an expression product from an expression vector described in Section 6.4. In an even more specific embodiment, such a polypeptide comprising an amino acid sequence consisting of SEQ ID NO: 1 has been expressed from Expression Vector 1. Also provided herein are dosage forms of Product 1 (see Section 6.5). Uses for Product 1 are also provided herein (see Section 6.6).

8.2 Polypeptides of the Invention

Figure 1:
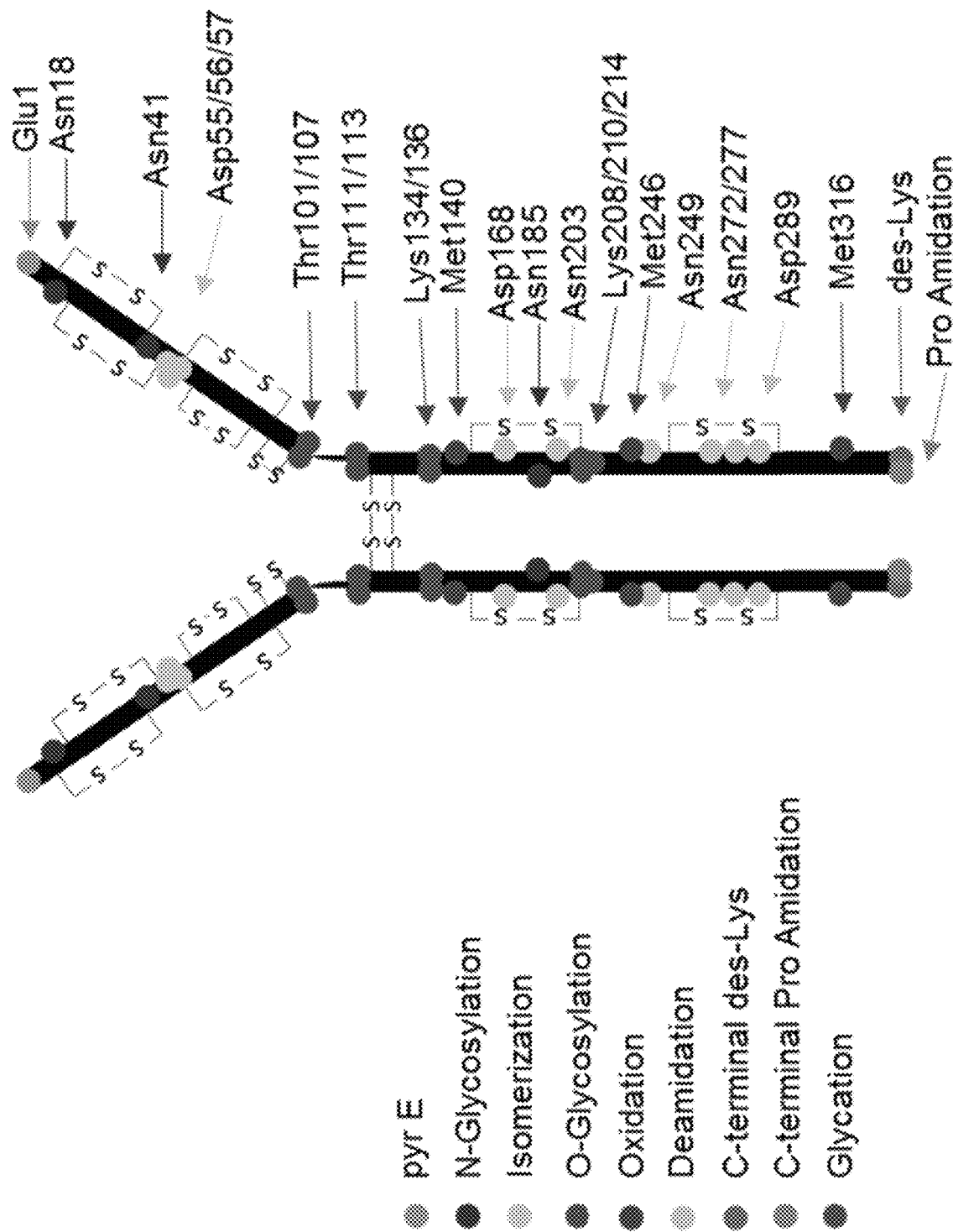

Provided herein are polypeptides comprising an extracellular domain (ECD) of human activin receptor IIB (ActRIIB) or derivatives thereof linked to a constant domain of an immunoglobulin, such as human IgG1 Fc domain. In a specific embodiment, provided herein is a product resulting from expression from an opening reading frame with the nucleotide sequence of SEQ ID NO:7 or a degenerate version of SEQ ID NO:7 that encodes SEQ ID NO: 1, and subsequent protein purification procedures (Product 1, exemplary primary structure illustrated in FIG. 1). In certain embodiments, provided herein are polypeptides comprising the amino acid sequence of SEQ ID NO: 1 wherein at least one amino acid is modified as described herein.

In certain embodiments, a polypeptide provided herein, such as Product 1, comprises a post-translational modification (PTM) such as a cyclized N-terminal glutamic acid, an N-glycosylation, a C-terminal Lysine (CTL) clipping, a C-terminal amidation, deamidation, isomerization, oxidation, glycation or O-glycosylation. In certain embodiments, Product 1 is a polypeptide that comprises at least one post-translational modification (PTM) such as a cyclized N-terminal glutamic acid, at least one N-glycosylation at an asparagine followed by the glycosylation consensus sequence (Asn-x-Ser/Thr), a C-terminal Lysine (CTL) clipping, a C-terminal proline amidation, at least one asparagine deamidation, at least one asparagine isomerization, at least one methionine oxidation, at least one lysine glycation or at least one threonine O-glycosylation. In a specific embodiment, Product 1 is a polypeptide that comprises at least one of the following post-translational modifications wherein modification positions correspond to positions in SEQ ID NO:2 such as a N-terminal pyroE, a C-terminal desLys, a C-terminal Pro amidation, a Asn203 deamidation, a Asn249 deamidation, a Asn272/277 deamidation, a Asp55/56/57 isomerization, a Asp168 isomerization, a Asp289 isomerization, a Met140 oxidation, a Met246 oxidation, a Met316 oxidation, a Lys134/136 glycation, Lys208/210/214 glycation, Thr101/107 O-glycosylation, or Thr111/113 O-glycosylation.

In certain embodiments, Product 1 is a mixture of polypeptides wherein at least one polypeptide comprises at least one post-translational modification (PTM) such as cyclized N-terminal glutamic acid, an N-glycosylation, a C-terminal Lysine (CTL) clipping, a C-terminal amidation, deamidation, isomerization, oxidation, glycation or O-glycosylation. In certain embodiments, Product 1 is a mixture of polypeptides wherein at least one polypeptide comprises at least one post-translational modification (PTM) such as a cyclized N-terminal glutamic acid, at least one N-glycosylation at an asparagine followed by the glycosylation consensus sequence (Asn-Xxx-Ser/Thr), a C-terminal Lysine (CTL) clipping, a C-terminal proline amidation, at least one asparagine deamidation, at least one asparagine isomerization, at least one methionine oxidation, at least one lysine glycation or at least one threonine O-glycosylation. In certain embodiments, Product 1 is a mixture of polypeptides wherein at least one polypeptide comprises at least one post-translational modification wherein modification positions correspond to positions in SEQ ID NO:2 such as a N-terminal pyroE, a C-terminal desLys, a C-terminal Pro amidation, a Asn203 deamidation, a Asn249 deamidation, a Asn272/277 deamidation, a Asp55/56/57 isomerization, a Asp 168 isomerization, a Asp289 isomerization, a Met140 oxidation, a Met246 oxidation, a Met316 oxidation, a Lys134/136 glycation, Lys208/210/214 glycation, Thr101/107 O-glycosylation, or Thr111/113 O-glycosylation. In a specific embodiment, Product 1 is a mixture of polypeptides wherein at least one polypeptide comprises at least one of the following post-translational modifications wherein modification positions correspond to positions in SEQ ID NO:2 in the following ranges such as: 0.5-1.5% N-terminal pyroE; 94-96% C-terminal desLys; 1.8-3.2% C-terminal Pro amidation; 3.4-4.2% Asn203 deamidation; 0.5-0.7% Asn249 deamidation; 5.0-6.3% Asn272/277 deamidation; 0.4-0.7% Asp55/56/57 isomerization; 0.3-0.5% Asp168 isomerization; 0.3-0.5% Asp289 isomerization; 1.0-1.3% Met140 oxidation; 0.1-0.4% Met246 oxidation; 0.5-1.0% Met316 oxidation; 0.1-0.5% Lys134/136 glycation; or 0.1-0.5% Lys208/210/214 glycation.

In certain embodiments, Product 1 is a mixture of polypeptides wherein at least 5%, at least 10%, at least 20%, at least 30%, at least 40%, at least 50%, at least 60%, at least 70%, at least 80%, at least 90%, at least 95% of the polypeptides comprises at least one of the following post-translational modifications wherein modification positions correspond to positions in SEQ ID NO: 2 such as N-terminal pyroE, a C-terminal desLys, a C-terminal Pro amidation, a Asn203 deamidation, a Asn249 deamidation, a Asn272/277 deamidation, a Asp55/56/57 isomerization, a Asp168 isomerization, a Asp289 isomerization, a Met140 oxidation, a Met246 oxidation, a Met316 oxidation, a Lys134/136 glycation, Lys208/210/214 glycation, Thr101/107 O-glycosylation, or Thr111/113 O-glycosylation. In a specific embodiment, Product 1 is a mixture of polypeptides wherein at least 5%, at least 10%, at least 20%, at least 30%, at least 40%, at least 50%, at least 60%, at least 70%, at least 80%, at least 90%, at least 95% of the polypeptides comprises at least one of the following post-translational modifications wherein modification positions correspond to positions in SEQ ID NO:2 in the following ranges such as: 0.5-1.5% N-terminal pyroE; 94-96% C-terminal desLys; 1.8-3.2% C-terminal Pro amidation; 3.4-4.2% Asn203 deamidation; 0.5-0.7% Asn249 deamidation; 5.0-6.3% Asn272/277 deamidation; 0.4-0.7% Asp55/56/57 isomerization; 0.3-0.5% Asp168 isomerization; 0.3-0.5% Asp289 isomerization; 1.0-1.3% Met140 oxidation; 0.1-0.4% Met246 oxidation; 0.5-1.0% Met316 oxidation; 0.1-0.5% Lys134/136 glycation; or 0.1-0.5% Lys208/210/214 glycation.

In certain embodiments, Product 1 is a mixture of polypeptides wherein at most 5%, at most 10%, at most 20%, at most 30%, at most 40%, at most 50%, at most 60%, at most 70%, at most 80%, at most 90% of the polypeptides comprises at least one of the following post-translational modifications wherein modification positions correspond to positions in SEQ ID NO: 2 such as N-terminal pyroE, a C-terminal desLys, a C-terminal Pro amidation, a Asn203 deamidation, a Asn249 deamidation, a Asn272/277 deamidation, a Asp55/56/57 isomerization, a Asp168 isomerization, a Asp289 isomerization, a Met140 oxidation, a Met246 oxidation, a Met316 oxidation, a Lys134/136 glycation, Lys208/210/214 glycation, Thr101/107 O-glycosylation, or Thr111/113 O-glycosylation. In a specific embodiment, Product 1 is a mixture of polypeptides wherein at most 5%, at most 10%, at most 20%, at most 30%, at most 40%, at most 50%, at most 60%, at most 70%, at most 80%, at most 90% of the polypeptides comprises at least one of the following post-translational modifications wherein modification positions correspond to positions in SEQ ID NO:2 in the following ranges such as: 0.5-1.5% N-terminal pyroE; 94-96% C-terminal desLys; 1.8-3.2% C-terminal Pro amidation; 3.4-4.2% Asn203 deamidation; 0.5-0.7% Asn249 deamidation; 5.0-6.3% Asn272/277 deamidation; 0.4-0.7% Asp55/56/57 isomerization; 0.3-0.5% Asp168 isomerization; 0.3-0.5% Asp289 isomerization; 1.0-1.3% Met140 oxidation; 0.1-0.4% Met246 oxidation; 0.5-1.0% Met316 oxidation; 0.1-0.5% Lys134/136 glycation; or 0.1-0.5% Lys208/210/214 glycation.

In certain embodiments, the mixture of polypeptides comprise at most 5%, most 10%, at most 20%, at most 30%, at most 40%, at most 50%, at most 60%, at most 70%, at most 80, or at most 90% Asn272/277 deamidation. In certain embodiments, the mixture of polypeptides comprise at most 60.6% Asn272/277 deamidation. In certain embodiments, the mixture of polypeptides comprise at most 88.7% Asn272/277 deamidation.

In certain embodiments, the mixture of polypeptides comprise at most 1%, at most 2%, at most 3%, at most 4%, at most 5%, at most 6%, at most 7%, at most 8%, at most 9%, at most 10%, at most 11%, or at most 20% low molecular weight species (LMWS) polypeptides. In certain embodiments, the mixture of polypeptides comprise at most 7.4% LMWS polypeptides. In certain embodiments, the mixture of polypeptides comprise at most 10.5% LMWS polypeptides.

In certain embodiments, the mixture of polypeptides comprise at most 1%, at most 2%, at most 3%, at most 4%, at most 5%, at most 6%, at most 7%, at most 8%, at most 9%, at most 10%, at most 11%, or at most 20% Asp55/56/57 isomerization. In certain embodiments, the mixture of polypeptides comprise at most 5.6% Asp55/56/57 isomerization. In certain embodiments, the mixture of polypeptides comprise at most 9.8% Asp55/56/57 isomerization.

In certain embodiments, the mixture of polypeptides comprise at most 1%, at most 2%, at most 3%, at most 4%, at most 5%, at most 6%, at most 7%, at most 8%, at most 9%, at most 10%, at most 15%, or at most 20% Met140 oxidation. In certain embodiments, the mixture of polypeptides comprise at most 8.9% Met140 oxidation. In certain embodiments, the mixture of polypeptides comprise at most 19.9% Met140 oxidation.

In certain embodiments, the mixture of polypeptides comprise at most 1%, at most 2%, at most 3%, at most 4%, at most 5%, at most 6%, at most 7%, at most 8%, at most 9%, at most 10%, at most 11%, or at most 20% Met316 oxidation. In certain embodiments, the mixture of polypeptides comprise at most 2.8% Met316 oxidation. In certain embodiments, the mixture of polypeptides comprise at most 9.1% Met316 oxidation.

In certain embodiments, the mixture of polypeptides comprise at most 1%, at most 2%, at most 3%, at most 4%, at most 5%, at most 6%, at most 7%, at most 8%, at most 9%, at most 10%, at most 11%, at most 20%, at most 25%, at most 30%, at most 35%, or at most 40% Lys208/210/214 glycation. In certain embodiments, the mixture of polypeptides comprise at most 23.9% Lys208/210/214 glycation. In certain embodiments, the mixture of polypeptides comprise at most 32.5% Lys208/210/214 glycation.

In certain embodiments, the mixture of polypeptides comprise at most 1%, at most 2%, at most 3%, at most 4%, at most 5%, at most 6%, at most 7%, at most 8%, at most 9%, or at most 10% high molecular weight species (HMWS) polypeptides. In certain embodiments, the mixture of polypeptides comprise at most 4.1% HMWS polypeptides. In certain embodiments, the mixture of polypeptides comprise at most 6.0% HMWS polypeptides.

In certain embodiments, the mixture of polypeptides comprise i) at most 60.6% or at most 88.7% Asn272/277 deamidation; ii) at most 7.4% or at most 10.5% LMW polypeptides; iii) at most 5.6% or at most 9.8% Asp55/56/57 isomerization; iv) at most 8.9% or at most 19.9% Met140 oxidation; v) at most 2.8% or at most 9.1% Met316 oxidation; vi) at most 23.9% or at most 32.5% Lys208/210/214 glycation; and vii) at most 4.1% or at most 6.0% HMW polypeptides.

In certain embodiments, the mixture of polypeptides comprise i) at most 60.6% Asn272/277 deamidation; ii) at most 7.4% LMW polypeptides; iii) at most 5.6% Asp55/56/57 isomerization; iv) at most 8.9% Met140 oxidation; v) at most 2.8% Met316 oxidation; vi) at most 23.9% Lys208/210/214 glycation; and vii) at most 4.1% HMW polypeptides.

In certain embodiments, the mixture of polypeptides comprise i) at most 88.7% Asn272/277 deamidation; ii) at most 10.5% LMW polypeptides; iii) at most 9.8% Asp55/56/57 isomerization; iv) at most 19.9% Met140 oxidation; v) at most 9.1% Met316 oxidation; vi) at most 32.5% Lys208/210/214 glycation; and vii) at most 6.0% HMW polypeptides.

Figure 6:
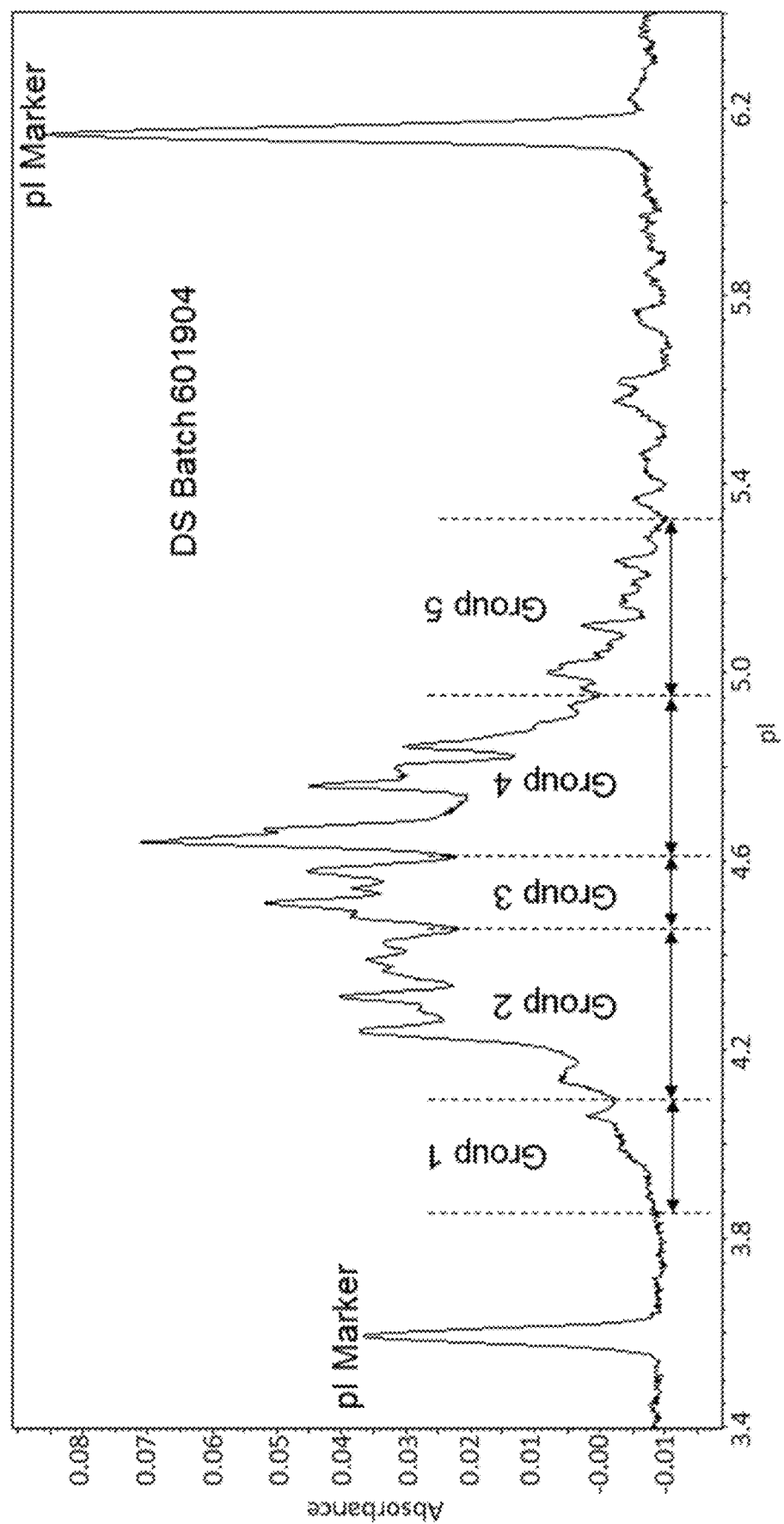

In certain embodiments, Product 1 can be characterized by charge heterogeneity. In certain embodiments, a charge heterogeneity icIEF profile for Product 1 is such that multiple peaks are observed in pI range from 1 to 7. In a specific embodiment, a charge heterogeneity icIEF profile for Product 1 is such that the profile can be divided into five groups wherein Group 1 is the most acidic and Group 5 is the most basic, and wherein the relative level of each group is as follows: Group 1 ranges between 2-5%; Group 2 ranges between 30-40%; Group 3 ranges between 18-25%; Group 4 ranges between 25-40%; and Group 5 ranges between 4-10%). In certain embodiments, the charge heterogeneity of Product 1 is substantially as shown in FIG. 6.

In certain embodiments, the biological activity of Product 1 can be characterized by bioassays such as binding to TGFβ ligand family members, effector function potential, and binding to neonatal receptor (FcRn).

In certain embodiments, Product 1 can be a potent inhibitor of GDF-11 dependent activation of ActIIB receptor SMAD2/3 signaling and can act as an erythroid maturation agent.

In certain embodiments, Product 1 can selectively bind to GDF-11 and GDF-8, but can have reduced affinity to other TGFβ ligand family members that bind to ACTIIB receptor.

In certain embodiments, Product 1 can act as a soluble ligand trap and does not induce effector function.

In certain embodiments, Product 1 can be associated with FcRn such that the association is consistent with that of an Fc containing protein and competed for binding to a wild-type human IgG1 antibody. Any suitable assay known to the skilled artisan can be used to demonstrate these activities.

8.3 Methods of Making Product 1, an ActRIIB Ligand Trap

Product 1, an ActRIIB ligand trap, is manufactured according to the methods provided herein. In certain embodiments provided herein, a host cell can be transfected with an expression vector including a coding sequence (e.g., SEQ ID NO:2) for the subject ActRIIB ligand trap. The host cell may be any prokaryotic or eukaryotic cell. For example, a ActRIIB ligand trap may be expressed in bacterial cells such as *E. coli*, insect cells (e.g., using a baculovirus expression system), yeast, or mammalian cells. Other suitable host cells are known to those skilled in the art. For example, a host cell transfected with an expression vector encoding a ActRIIB ligand trap can be cultured under appropriate conditions to allow expression of the ActRIIB ligand trap to occur. The ActRIIB ligand trap may be secreted and isolated from a mixture of cells and medium containing the ActRIIB ligand trap. Alternatively, the ActRIIB ligand trap may be retained cytoplasmically or in a membrane fraction and the cells harvested, lysed and the protein isolated. A cell culture includes host cells, media and byproducts. Suitable media for cell culture are well known in the art. The subject ActRIIB ligand traps can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the ActRIIB ligand traps.

In certain embodiments, ActRIIB ligand trap can be expressed in cell culture in a bioreactor such as a 100 L, 500 L, 1,000 L, 2,000 L, 3,000 L, 4,000 L, 5,000 L, 6,000 L, 7,000 L, 8,000 L, 9,000 L, 10,000 L, 20,000 L, 30,000 L, 40,000 L, or 50,000 L production bioreactor. In certain embodiments, the bioreactor can be inoculated with cells that comprise an expression vector encoding the ActRIIB ligand trap (see Section 6.2). The cell can be any prokaryotic or eukaryotic cell. For example, an ActRIIB ligand trap may be expressed in bacterial cells such as $E.$ $coli$, insect cells (e.g., using a baculovirus expression system), yeast, or mammalian cells. Other suitable host cells are known to those skilled in the art. The inoculation cell density can be $(2.5$ to $5.5) \times 10^4$ cells/mL, $(2.5$ to $5.5) \times 10^5$ cells/mL, or $(2.5$ to $5.5) \times 10^6$ cells/mL and the viability can be 70-90%. The medium can be any suitable production medium known to those skilled in the art supplemented with supplements such as L-glutamine, Liquid Cyclodextrin, Sodium Chloride, Hydrochloric Acid, Sodium Hydroxide Solution, L-Cystine Disodium, Medium 1 Powder, Medium 2 Powder, Amino Acid Mix Powder, Phytone UF, and/or Proyield Wheat.

In certain embodiments, the production medium is equilibrated to 37° C. and pH is set between 6.9-7.4 prior to inoculation. In certain embodiments, the bioreactor pH is controlled at a set point for 48 hours. The pH set point can be between 6.9-7.4. In certain embodiments, the pH is shifted down over a period of 48 hours to a target set point between 6.5-7.0. In certain embodiments, the bioreactor temperature is maintained at 37° C. until cell density reaches $(40.0$ to $130.0) \times 10^5$ cells/mL, then it can be lowered to a set point between 32-35° C. until harvest. In certain embodiments, the bioreactor is supplemented nutrient feeds. The nutrient feeds can be any suitable nutrient feed known to those skilled in the art for the delivery of essential nutrients to cell culture. In certain embodiments, the bioreactor is supplemented with glucose to maintain a concentration of at least 0.5 g/L. In certain embodiments, the cell culture duration in the bioreactor is between 10.0-20.0 days where culture viability is at least 10%.

In certain embodiments, depth filtration steps are introduced to harvest the bioreactor culture. The cell culture can be pumped through a depth filtration system at a flow rate of at most 5.0 L/min, at most 10.0 L/min, at most 15.0 L/min, or at most 20.0 L/min. In certain embodiments, the ActRIIB ligand trap is concentrated with an affinity chromatography step. The affinity chromatography step can be Protein A, Protein G, or a mixture of Protein A/G. In some embodiments, the ActRIIB ligand trap is a fusion protein containing a domain which facilitates its purification. In some embodiments, a fusion gene coding for a purification affinity tag, such as a poly-(His)/enterokinase cleavage site sequence at the N-terminus of the desired portion of the recombinant ActRIIB ligand trap, can allow purification of the expressed fusion protein by affinity chromatography using a $Ni^{2+}$ metal resin. The purification affinity tag sequence can then be subsequently removed by treatment with enterokinase to provide the purified ActRIIB ligand trap (e.g., see Hochuli et al., J. Chromatography, 411:177 (1987); and Janknecht et al., PNAS USA, 88:8972-8976 (1991)). Other suitable affinity capture methods are known to those skilled in the art.

In certain embodiments, filtration steps are introduced to reduce impurities and media components. The filtration steps can be viral filtration, ultrafiltration, or diafiltration. The filtration columns can be Q Sepharose or Phenyl Sepharose. In certain embodiments, an acidic pH shift is introduced during filtration to inactivate potential viral contaminants. The inactivation step can be held at a pH between 2.8-4.0. In certain embodiments, a shift in temperature can accompany the inactivation step. The temperature shift can be between 10-30° C. In certain embodiments, a final filtration step is performed before freezing the ActRIIB ligand trap for long-term storage at −65° C.

8.4 Polynucleotides

Figure 2:
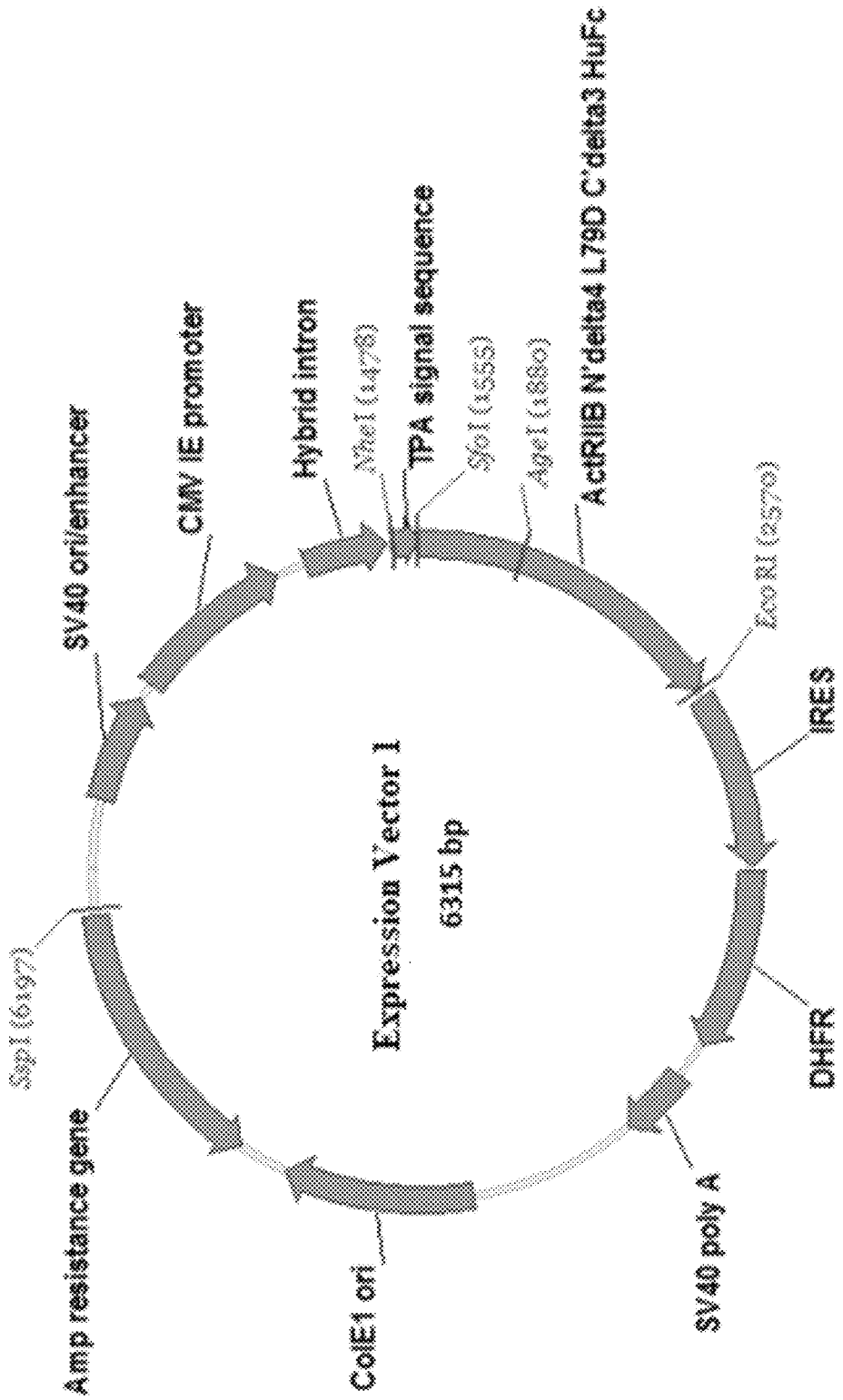

In a specific embodiment, an expression vector that can be used with the methods and compositions provided herein is Expression Vector 1. A restriction map of the Expression Vector 1 is shown in FIG. 2. In certain embodiments, Expression Vector 1 is used to generate Product 1, an ActRIIB Ligand Trap (see Section 6.2).

In certain embodiments, an expression vector that can be used to express the compositions provided herein comprises the following components: a promoter sequence, optionally a 5' untranslated region of a nucleotide sequence encoding a leader sequence, a 5' translated region encoding a signal sequence, a nucleotide sequence encoding an extracellular domain of ActRIIB or a derivative thereof, a nucleotide sequence encoding a linker sequence, a nucleotide sequence encoding the constant region of an immunoglobulin (such as IgG1), and optionally a 3' untranslated region.

In certain embodiments, the recombinant nucleic acids provided herein may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated herein. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, the subject nucleic acid is provided in an expression vector comprising a nucleotide sequence encoding a ActRIIB ligand trap and operably linked to at least one regulatory sequence. Regulatory sequences are art-recognized and are selected to direct expression of the ActRIIB ligand trap. Accordingly, the term regulatory sequence includes promoters, enhancers, and other expression control elements. Exemplary regulatory sequences are described in Goeddel; Gene Expression Technology: Methods in Enzymology, Academic Press, San Diego, CA (1990). For instance, any of a wide variety of expression control sequences that control the expression of a DNA sequence when operatively linked to it may be used in these vectors to express DNA sequences encoding a ActRIIB ligand trap. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid provided herein can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB ligand trap include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli. Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-I), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUWl), and pBlueBac-derived vectors (such as the β-gal containing pBlueBac III).

In a specific embodiment, a vector will be designed for production of the subject ActRIIB ligand traps in Chinese Hamster Ovary (CHO) cells, such as a Pcmv-Script vector (Stratagene, La Jolla, CA), pcDNA4 vectors (Invitrogen, Carlsbad, CA), PIRESneo3 vector (Takara Bio, Mountain View, CA) and pCI-neo vectors (Promega, Madison, WI). As will be apparent, the subject gene constructs can be used to cause expression of the subject ActRIIB ligand traps in cells propagated in culture, e.g., to produce proteins, including fusion proteins or variant proteins, for purification. In certain embodiments, the expression vector comprises restriction sites for incorporation of cDNA coding for the ActRIIB ligand trap extracellular domain (ECD). Suitable restriction sites and corresponding restriction enzymes are well-known in the art.

In certain embodiments, the expression vector comprises a nucleotide sequence encoding an extracellular domain (ECD) of human activin receptor IIB (ActRIIB) linked to a constant domain of an immunoglobulin, such as the human IgG1 Fc domain.

In certain embodiments, the expression vector comprises a nucleotide sequence encoding a truncated extracellular domain (ECD) of human activin receptor IIB (ActRIIB) linked to a constant domain of an immunoglobulin, such as human IgG1 Fc domain.

In certain embodiments, the expression vector comprises a nucleotide sequence encoding the extracellular domain (ECD) of human activin receptor IIB (ActRIIB). In certain embodiments, the expression vector comprises a nucleotide sequence encoding a modified extracellular domain (ECD) of human activin receptor IIB (ActRIIB) that starts at amino acid position 25 in sequence SEQ ID NO:3. In another embodiment, the expression vector comprises a nucleotide sequence encoding a modified extracellular domain (ECD) of human activin receptor IIB (ActRIIB) that ends at amino acid position 131 of sequence SEQ ID NO:3. In certain embodiments, the expression vector comprises a nucleotide sequence encoding a modified extracellular domain (ECD) of human activin receptor IIB (ActRIIB) that has an amino acid substitution at the position 79 of the amino acid sequence SEQ ID NO:3. In a specific embodiment, the leucine at position 79 of the amino acid sequence SEQ ID NO:3 is substituted with an acidic amino acid. In an even more specific embodiment, the leucine at position 79 of SEQ ID NO:3 is substituted with an aspartate ("L79D"). The mature Product 1 lacking the signal peptide has the L→D substitution at position 55. However, the nomenclature for this amino acid substitution as "L79D" is maintained throughout this application even if the expression product is truncated such that L79 is no longer at the 79th position of the truncated amino acid sequence. In certain embodiments, the expression vector comprises a nucleotide sequence encoding a modified extracellular domain (ECD) of human activin receptor IIB (ActRIIB) that starts at amino acid position 25 and ends at amino acid position 131 of sequence SEQ ID NO:3. In a more specific embodiment, the expression vector comprises a nucleotide sequence encoding a modified extracellular domain (ECD) of human activin receptor IIB (ActRIIB) that starts at amino acid position 25, has a L79D substitution, and ends at amino acid position 131 of sequence SEQ ID NO:3. In another specific embodiment, the expression vector comprises a nucleotide sequence encoding a modified extracellular domain (ECD) of human activin receptor IIB (ActRIIB) consisting of amino acid sequence SEQ ID NO:4.

In certain embodiments, the expression vector comprises a nucleotide sequence encoding a modified extracellular domain (ECD) of human activin receptor IIB (ActRIIB) linked to a constant domain of an immunoglobulin, such as the human IgG1 Fc domain, with a 5' translated signal sequence. In a specific embodiment, the expression vector comprises a nucleotide sequence encoding a modified extracellular domain (ECD) of human activin receptor IIB (ActRIIB) linked to a constant domain of an immunoglobulin, such as the human IgG1 Fc domain, with a 5' tissue plasminogen activator (TPA) signal sequence consisting of amino acid sequence SEQ ID NO:5.

In certain embodiments, the expression vector comprises a nucleotide sequence encoding a truncated extracellular domain (ECD) of human activin receptor IIB (ActRIIB) linked to a constant domain of an immunoglobulin, such as the human IgG1 Fc domain wherein the modified ECD lacks amino acid position 25, 26, 27, 28, 29, 30, 31, 32, 33, 34, or 35 of SEQ ID NO: 3. In certain embodiments, the expression vector comprises a nucleotide sequence encoding a truncated extracellular domain (ECD) of human activin receptor IIB (ActRIIB) linked to a constant domain of an immunoglobulin, such as the human IgG1 Fc domain wherein the modified ECD lacks amino acid position 121, 122, 123, 124, 125, 126, 127, 128, 129, 130, or 131 of SEQ ID NO:3. In certain embodiments, the expression vector comprises a nucleotide sequence encoding a truncated extracellular domain (ECD) of human activin receptor IIB (ActRIIB) linked to a constant domain of an immunoglobulin, such as the human IgG1 Fc domain wherein the modified ECD lacks amino acid position 25, 26, 27, 28, 29, 30, 31, 32, 33, 34, or 35 and lacks amino acid position 121, 122, 123, 124, 125, 126, 127, 128, 129, 130, or 131 of SEQ ID NO:3. In certain embodiments, the expression vector comprises a nucleotide sequence encoding a truncated extracellular domain (ECD) of human activin receptor IIB (ActRIIB) linked to a constant domain of an immunoglobulin, such as the human IgG1 Fc domain wherein the modified ECD lacks amino acid position 25, 26, 27, 28, 29, 30, 31, 32, 33, 34, or 35, has an L79D substitution, and lacks amino acid position 121, 122, 123, 124, 125, 126, 127, 128, 129, 130, or 131 of SEQ ID NO:3.

In certain embodiments, the expression vector comprises a nucleotide sequence encoding a modified extracellular domain (ECD) of human activin receptor IIB (ActRIIB) linked by a linker region to a constant domain of an immunoglobulin, such as the human IgG1 Fc domain, wherein the linker region is 1, 2, 3, 4, 5, 6, 7, 8, 9 or 10 amino acids long. In a specific embodiment, the expression vector comprises a nucleotide sequence encoding a truncated extracellular domain (ECD) of human activin receptor IIB (ActRIIB) linked by a linker region to a constant domain of an immunoglobulin, such as the human IgG1 Fc domain, consisting of SEQ ID NO: 6 wherein the linker region is three amino acids long.

8.5 Dosage Forms of Product 1

In another aspect, provide herein are dosage forms comprising Product 1. In certain embodiments, provided is a dosage form comprising Product 1 wherein Product 1 is in a lyophilized form or in a liquid solution in a vial.

In certain embodiments, the dosage form comprises about 15 mg, about 17.5 mg, about 20 mg, about 22.5 mg, about 25 mg, about 27.5 mg, about 30 mg, about 32.5 mg, about 35 mg, about 37.5 mg, about 40 mg, about 42.5 mg, about 45 mg, about 47.5 mg, about 50 mg, about 52.5 mg, about 55 mg, about 57.5 mg, about 60 mg, about 62.5 mg, about 65 mg, about 67.5 mg, about 70 mg, about 72.5 mg, about 75 mg, about 77.5 mg, about 80 mg, about 82.5 mg, about 85 mg, about 90 mg, about 92.5 mg, about 95 mg, about 97.5 mg or about 100 mg of Product 1.

8.6 Uses of ActRIIB Ligand Traps

In certain embodiments, an ActRIIB Ligand Trap described herein, such as the Product 1, can be used for treating a human subject diagnosed with anemia due to very low, low, or intermediate risk myelodysplastic syndromes (MDS).

The subjects treated in accordance with the methods described herein can be any mammals such as rodents and primates, and in a preferred embodiment, humans. In certain embodiments, the methods described herein can be used to treat anemia due to very low, low, or intermediate risk Myelodysplastic syndromes (MDS) in a subject, to reduce transfusion burden in a subject with anemia, or to monitor said treatment, and/or to select subjects to be treated in accordance with the methods provided herein, in any mammal such as a rodent or primate, and in a preferred embodiment, in a human subject.

In certain embodiments, the subject treated in accordance with the methods described herein is female. In certain embodiments, the subject treated in accordance with the methods described herein is male. In certain embodiments, the subject treated in accordance with the methods described herein can be of any age. In certain embodiments, the subject treated in accordance with the methods described herein is less than 18 years old. In a specific embodiment, the subject treated in accordance with the methods described herein is less than 13 years old. In another specific embodiment, the subject treated in accordance with the methods described herein is less than 12, less than 11, less than 10, less than 9, less than 8, less than 7, less than 6, or less than 5 years old. In another specific embodiment, the subject treated in accordance with the methods described herein is 1-3 years old, 3-5 years old, 5-7 years old, 7-9 years old, 9-11 years old, 11-13 years old, 13-15 years old, 15-20 years old, 20-25 years old, 25-30 years old, or greater than 30 years old. In another specific embodiment, the subject treated in accordance with the methods described herein is 30-35 years old, 35-40 years old, 40-45 years old, 45-50 years old, 50-55 years old, 55-60 years old, or greater than 60 years old. In another specific embodiment, the subject treated in accordance with the methods described herein is 18-64 years old, 65-74 years old, or greater than 75 years old.

In certain embodiments, a subject treated in accordance with the methods provided herein has been diagnosed with IPSS-R defined MDS. IPSS-R refers to the International Prognostic Scoring System-Revised, which is utilized in the evaluation of prognosis in myelodysplastic syndromes. See, e.g., Greenberg et al., Blood, 120 (12): 2454-2465 (2012). The IPSS-R utilizes a criteria point system to characterize myelodysplastic syndrome patient outcomes as very low risk (0-1.5 risk score, median survival 8.8 years), low risk (1.5-3.0 risk score; median survival of 5.3 years), intermediate (3.0-4.5 point; median survival of 3.0 years); high risk (4.5-6.0 points; median survival of 1.6 years); or very high risk (risk score higher than 6; median survival of 0.8 years). The point system evaluates (i) the percentage of bone marrow blasts in the subject; and (ii) cytogenetics in the subject which defined as hemoglobin concentration (g/dL), absolute neutrophil count ($\times 10^9$/L), and platelet count ($\times 10^9$/L).

In certain embodiments, a subject treated in accordance with the methods provided herein has MDS. In certain embodiments, the MDS is IPSS-defined very low risk MDS. In certain embodiments, the MDS is IPSS-R defined low risk MDS. In certain embodiments, the MDS is IPSS-R defined intermediate risk MDS. In certain embodiments, a subject treated in accordance with the methods provided herein has MDS-refractory cytopenia with multilineage dysplasia (MDS-RCMD).

In certain embodiments, the subject treated in accordance with the methods described herein has an Eastern Cooperative Oncology Group (ECOG) score of 0. In certain embodiments, the subject treated in accordance with the methods described herein has an ECOG score of 1. In certain embodiments, the subject treated in accordance with the methods described herein has an ECOG score of 2.

In certain embodiments, the percentage of erythroblasts in a subject treated in accordance with the methods provided herein that are ring sideroblasts is at least 5%, 6%, 7%, 8%, 9%, 10%, 11%, 12%, 13%, 14%, 15%, 16%, 17%, 18%, 19%, or at least 20%. In certain embodiments, the percentage of erythroblasts in a subject treated in accordance with the methods provided herein that are ring sideroblasts is at least 15%. In certain embodiments, the percentage of erythroblasts in a subject treated in accordance with the methods provided herein that are ring sideroblasts is about 15%. In certain embodiments, the percentage of erythroblasts in a subject treated in accordance with the methods provided herein that are ring sideroblasts is between about 15% and about 20%. In certain embodiments, the percentage of erythroblasts in a subject treated in accordance with the methods provided herein that are ring sideroblasts is between about 5% and 20%. In certain embodiments, a subject treated in accordance with the methods provided herein has a ringed sideroblast to normal erythroblast ratio of at least 1:20, at least 1:7, or at least 1:5.

In certain embodiments, a subject having anemia due to very low, low, or intermediate risk MDS treated requires regular, lifelong red blood cell transfusions. In certain embodiments, a subject having anemia due to very low, low, or intermediate risk MDS requires transfusion of 0 to 4 red blood cell units over a 8-weeks period. In certain embodiments, a subject having anemia due to very low, low, or intermediate risk MDS requires transfusion of 4 to 6 red blood cell units over a 8-weeks period. In certain embodiments, a subject having anemia due to very low, low, or intermediate risk MDS requires transfusion of less than 6 red blood cell units over a 8-weeks period. In certain embodiments, a subject having anemia due to very low, low, or intermediate risk MDS requires transfusion of more than 6 red blood cell units over a 8-weeks period. In certain embodiments, a subject having anemia due to very low, low, or intermediate risk MDS has a high transfusion burden. In certain embodiments, high transfusion burden is 12 or more red blood cell units over 24 weeks prior to treatment according to the methods provided herein. In certain embodiments, a subject treated in accordance with the methods provided herein has a low transfusion burden. In certain embodiments, the subject with a low transfusion burden treated in accordance with the methods provided herein requires at most 0, 1, 2, or 3 units of red blood cells per 8 weeks. In certain embodiments, a subject treated in accordance with the methods provided herein has a high transfusion burden. In certain embodiments, the subject with a high transfusion burden treated in accordance with the methods provided herein requires at least 4, 5, 6, 7, 8, 9, 10, 11, 12, or 13 units of red blood cells per 8 weeks.

In embodiments, a subject treated has one or more mutations in the SF3B1 gene. In certain embodiments, the one or more mutations in SF3B1 gene has been confirmed by genetic analysis. In certain embodiments, the one or more mutations is in a non-coding region. In certain embodiments, SF3B1 is the gene encoding SB3B1. In certain embodiments, the one or more mutations is in a coding region. In certain embodiments, SF3B1 is SF3B1 protein. In certain embodiments, the one or more mutations in SF3B1 protein is selected from the group consisting of E622D, R625C, H662Q, H662D, K66N, K666T, K666Q, K666E, A672D, K700E, 1704N. In certain embodiments, a subject treated in accordance with the methods provided herein expresses SF3B1 protein with the mutation E622D. In certain embodiments, a subject treated in accordance with the methods provided herein expresses SF3B1 protein with the mutation R625C. In certain embodiments, a subject treated in accordance with the methods provided herein expresses SF3B1 protein with the mutation H662Q. In certain embodiments, a subject treated in accordance with the methods provided herein expresses SF3B1 protein with the mutation H662D. In certain embodiments, a subject treated in accordance with the methods provided herein expresses SF3B1 protein with the mutation K66N. In certain embodiments, a subject treated in accordance with the methods provided herein expresses SF3B1 protein with the mutation K666T. In certain embodiments, a subject treated in accordance with the methods provided herein expresses SF3B1 protein with the mutation K666Q. In certain embodiments, a subject treated in accordance with the methods provided herein expresses SF3B1 protein with the mutation K666E. In certain embodiments, a subject treated in accordance with the methods provided herein expresses SF3B1 protein with the mutation A672D. In certain embodiments, a subject treated in accordance with the methods provided herein expresses SF3B1 with the mutation K700E. In certain embodiments, a subject treated in accordance with the methods provided herein expresses SF3B1 protein with the mutation 1704N. In a specific embodiment, a subject treated in accordance with the methods provided herein expresses SRSF2 with one or more mutations. In a specific embodiment, a subject treated in accordance with the methods provided herein expresses DNMT3A with one or more mutations. In a specific embodiment, a subject treated in accordance with the methods provided herein expresses TET2 with one or more mutations. In a specific embodiment, a subject treated in accordance with the methods provided herein expresses SETBP1 with one or more mutations.

In certain embodiments, a subject treated in accordance with the methods provided herein (i) has anemia due to very low, low or intermediate risk MDS, (ii) at least 15% of erythroblasts in the subject are ring sideroblasts. In certain embodiments, a subject treated in accordance with the methods provided herein (i) has anemia due to very low, low or intermediate risk MDS, (ii) at least 5% of erythroblasts in the subject are ring sideroblasts, and (iii) expresses SF3B1 with one or more mutations.

In certain embodiments, a subject treated in accordance with the methods provided herein has thrombocytopenia. In certain embodiments, a subject treated in accordance with the methods provided herein has less than $100 \times 10^9$ platelets per liter. In certain embodiments, a subject treated in accordance with the methods provided herein has 100 to $400 \times 10^9$ platelets per liter. In certain embodiments, a subject treated in accordance with the methods provided herein has more than $400 \times 10^9$ platelets per liter. In certain embodiments, a subject treated in accordance with the methods provided herein has neutropenia. In certain embodiments, a subject treated in accordance with the methods provided herein has an absolute neutrophil count of less than $1 \times 10^9$ per liter.

In certain embodiments, a subject treated in accordance with the methods provided herein has less than 13,000 white blood cells per µL, less than 12,000 white blood cells per µL, less than 11,000 white blood cells per µL, less than 10,000 white blood cells per µL, less than 7,500 white blood cells per µL, or less than 500 white blood cells per µL.

In certain embodiments, hemoglobin levels in a subject treated in accordance with the methods provided herein are less than 10 g/dL, 9 g/dL, 8 g/dL, or 7 g/dL. In certain embodiments, hemoglobin levels in a subject treated in accordance with the methods provided herein are between 7 g/dL and 7.5 g/dL, between 7.5 g/dL and 8 g/dL, between 8 g/dL and 8.5 g/dL, between 8.5 g/dL and 9.0 g/dL, between 9.0 g/dL and 9.5 g/dL, or between 9.5 g/dL and 10.0 g/dL.

In certain embodiments of any of the foregoing methods, a subject can be refractory to prior Erythropoiesis-stimulating agents (ESA) treatment. In certain embodiments of any of the foregoing methods, a subject can be intolerant to prior ESA treatment. In certain embodiments of any of the foregoing methods, a subject can be ineligible to ESA treatment.

In certain embodiments of any of the foregoing methods, a subject who is refractory to prior ESA treatment can be a subject who has a non-response or response that is no longer maintained to prior ESA-containing regimen, either as single agent or combination with other agent, at any time after introduction due to intolerance or an adverse event.

In certain embodiments of any of the foregoing methods, the subject is intolerant to prior ESA treatment. In certain embodiments, the prior ESA-containing regimen, either as single agent or combination with other agent, at any time after introduction has been discontinued in the subject due to intolerance or an adverse event.

In certain embodiments of any of the foregoing methods, the subject is intolerant to prior ESA treatment. In certain embodiments, the subject has a low chance to respond to ESA treatments due to a high endogenous serum erythropoietin (EPO) level. In certain embodiments of any of the foregoing methods, the subject has not been previously treated with ESAs and has a serum EPO level >200 IU/L.

In certain embodiments, a subject treated in accordance with the methods provided herein has undergone prior treatment with one or more ESAs or is currently undergoing treatment with one or more ESAs. In certain embodiments, a subject treated in accordance with the methods provided herein does not respond to treatment with one or more ESAs. In certain embodiments, a subject treated in accordance with the methods provided herein is refractory to treatment with one or more ESAs. In certain embodiments, a subject treated in accordance with the methods provided herein becomes refractory to treatment with one or more ESAs. In certain embodiments, a subject treated in accordance with the methods provided herein is refractory to prior ESA treatment. In certain embodiments, a subject who is refractory to prior ESA treatment has documented non-response or response that is no longer maintained to prior ESA-containing regimen, either as single agent or combination with other agents (e.g., with G-CSF); the ESA regimen must have been either (a) recombinant human erythropoietin of greater than 40,000 IU/week for at least 8 doses or equivalent, or (b) darbepoetin alpha of greater than 500 µg once every three weeks for at least 4 doses or equivalent. In certain embodiments, a subject treated in accordance with the methods provided herein is intolerant to prior ESA-treatment. In certain embodiments, a subject who is intolerant to prior ESA-treatment has documented discontinuation of prior ESA-containing regimen, either as single agent or combination (e.g., with G-CSF), at any time after introduction due to intolerance or an adverse event. In certain embodiments, a subject treated in accordance with the methods provided herein is ESA-ineligible. In certain embodiments, a subject who is ESA-ineligible has a low chance of response to ESA based on an endogenous serum erythropoietin level of greater than 200 IU/L for subjects not previously treated with ESAs.

In certain embodiments, the subject treated in accordance with the methods described herein has MDS. In certain embodiments, the subject treated in accordance with the methods described herein has MDS and intact chromosome 5q. In certain embodiments, the subject treated in accordance with the methods provided herein has MDS, intact chromosome 5q, and does not have documented treatment failure with lenalidomide. In certain embodiments, the subject treated in accordance with the methods provided herein has MDS, intact chromosome 5q, and documented treatment failure with lenalidomide. In certain embodiments, the subject treated in accordance with the methods described herein has MDS with chromosome 5q deletion. MDS with chromosome 5q deletion comprises a deletion of the long arm of chromosome 5 and is characterized by, inter alia, macrocytic anemia with oval macrocytes, normal to slightly reduced white blood cell counts, normal to elevated platelet counts, and less than 5% blasts in the bone marrow and blood. In certain embodiments, the subject treated in accordance with the methods provided herein has MDS with chromosome 5q deletion and does not have documented treatment failure with lenalidomide. In certain embodiments, the subject treated in accordance with the methods provided herein has MDS with chromosome 5q deletion and documented treatment failure with lenalidomide. In certain embodiments, treatment failure with lenalidomide comprises loss of response to lenalidomide, no response to lenalidomide after 4 months of treatment with lenalidomide, intolerance to treatment with lenalidomide, or cytopenia precluding treatment with lenalidomide.

In certain embodiments, a subject treated in accordance with the methods provided herein has an EPO serum concentration of greater than 500 IU/L. In certain embodiments, a subject treated in accordance with the methods provided herein has an EPO serum concentration between 200 and 500 IU/L. In certain embodiments, a subject treated in accordance with the methods provided herein has an EPO serum concentration between 100 and 200 IU/L. In certain embodiments, a subject treated in accordance with the methods provided herein has an EPO serum concentration less than 100 IU/L.

In certain embodiments, a subject treated in accordance with the methods provided herein has a renal creatinine clearance rate between 40-60 mL/min. In certain embodiments, a subject treated in accordance with the methods provided herein has a renal creatinine clearance rate greater than 60 mL/min.

In certain embodiments, a subject treated in accordance with the methods provided herein has a baseline platelet count less than $100 \times 10^9$ count/L. In certain embodiments, a subject treated in accordance with the methods provided herein has a baseline platelet count between 100 to $400 \times 10^9$ count/L. In certain embodiments, a subject treated in accordance with the methods provided herein has a baseline platelet count greater than $400 \times 10^9$ count/L.

In certain embodiments, a subject treated in accordance with the methods provided herein has received initial diagnosis of MDS between 0 to 2 years prior to the administration of a polypeptide comprising an amino acid sequence of SEQ ID NO:1 or SEQ ID NO:2. In certain embodiments, a subject treated in accordance with the methods provided herein has received initial diagnosis of MDS between 2 to 5 years prior to the administration of a polypeptide comprising an amino acid sequence of SEQ ID NO: 1 or SEQ ID NO:2. In certain embodiments, a subject treated in accordance with the methods provided herein has received initial diagnosis of MDS more than 5 years prior to the administration of a polypeptide comprising an amino acid sequence of SEQ ID NO: 1 or SEQ ID NO:2.

9. EXAMPLES

9.1 Example 1: Expression and Purification of Product 1

(a) Introduction

This example is a characterization of the methods used for expression and purification of Product 1. The plasmid map for Expression Vector 1 is shown in FIG. 2, see also FIG. 21, showing the coding sequence (SEQ ID NO:7) and base polypeptide sequence of Product 1.

(b) Strategy and Methods

Host CHO cells were transfected with Expression Vector 1 (FIG. 2). CHO cells with Expression Vector 1 were cultured in a bioreactor at an optimal cell density and viability. The production medium was equilibrated for temperature and pH prior to inoculation of host cells with Expression Vector 1.

The production bioreactor was fed nutrient feeds of Medium 1 and amino acid mix medium prior to harvesting the cells. Basal culture media, Medium 1 and a second medium, Medium 2, were prepared by a commercial vendor, supplied as a sterile liquid in bags, and used for cell culture. The liquid medium was converted to a powder form and rehydrated prior to use. Medium 1 was made up of hydrated Medium 1 powder which contained at least the following components: L-alanine, glycine, L-arginine HCl, L-asparagine $H_2O$, L-cysteine HCl $H_2O$, L-glutamic Acid, glutathione reduced, L-histidine HCl $H_2O$, L-isoleucine, L-leucine, L-lysine HCl, L-methionine, L-phenylalanine, L-proline, L-serine, L-threonine, L-tryptophan, L-valine, D, glucose (dextrose), HEPES, para amino benzoic acid, vitamin B-12, biotin, choline chloride, folic acid, I-inositol, niacinamide, D-calcium pantothenate, pyridoxine HCl, riboflavin, thiamine HCl, DL lipoic acid (thioctic), aluminum chloride $6H_2O$, ammonium meta vanadate, ammonium molybdate $4H_2O$, barium acetate, cadmium chloride $2.5H_2O$, calcium chloride anhydrous, chromium chloride $6H_2O$, L-cystine disodium salt, ethanolamine HCl, ferric chloride $6H_2O$, ferric nitrate $9H_2O$, germanium dioxide, linoleic acid, magnesium chloride anhydrous, magnesium sulfate anhydrous, nickelous sulfate $6H_2O$, potassium bromide, potassium chloride, putrescine 2HCl, rubidium chloride, silver nitrate, sodium citrate $2H_2O$, sodium fluoride, sodium metasilicate $9H_2O$, sodium selenite, sodium phosphate dibasic anhydrous, L-tyrosine disodium salt, stannous chloride $2H_2O$, zirconyl chloride $8H_2O$, dextran sulfate, sodium pyruvate, cobalt chloride $6H_2O$, cupric sulfate $5H_2O$, ferrous sulfate $7H_2O$, manganous sulfate $H_2O$, potassium iodide, sodium bicarbonate, sodium chloride, sodium phosphate monobasic, zinc sulfate $7H_2O$, L-aspartic Acid, recombinant human insulin, and milled pluronic F-68. The amino acid medium was made up of hydrated amino acid mix powder which contained the following components: L-asparagine $H_2O$, L-isoleucine, L leucine, L-aerine, L-valine) at a target amount between 2.0-4.0% wet weight.

Product 1 was harvested from the bioreactor cell culture by being pumped through a depth filtration system at a fixed flow rate. Product 1 was concentrated using a Protein A affinity chromatography step. The Product 1 was further purified and concentrated using an acidic shift in pH to inactivate viral contaminants, followed by two additional filtration steps using Q Sepharose or Phenyl Sepharose chromatography. Final purification steps included a Virosart viral filtration followed by ultrafiltration/diafiltration. Bulk Product 1 was stored and frozen at ≤ −65° C.

9.2 Example 2: An In-Depth Characterization of Primary Structure of Product 1

(a) Introduction

This example presents an in-depth characterization of primary structure of Product 1 that was performed on representative DS batch A1. The amino acid sequence was confirmed by peptide mapping using trypsin or Glu-C endopeptidase. Protein was digested with proteolytic enzyme and resulting peptides were separated using a reversed-phase column and the peaks were detected by UV as well as by inline mass spectrometry (MS). Sequence variants and post-translational modifications (PTM) were also identified and their relative levels were quantitated from extracted ion chromatograms. Cyclized N-terminal glutamic acid, C-terminal Lysine (CTL) clipping, C-terminal amidation, deamidation, isomerization, oxidation and glycation were all detected at low levels in drug substance (DS) batch A1.

(b) Strategy and Methods

For peptide map analysis, Product 1 was diluted in denaturing solution containing 6 M guanidine hydrochloride. The denatured sample was reduced with dithiothreitol, alkylated with iodoacetamide, and buffer exchanged into digestion buffer prior to digestion with trypsin endopeptidase. Resulting peptides were separated by RP-UPLC using a C18 column. Ultraviolet (UV) absorbance was monitored at 214 nm and peptides were identified by inline MS and MS/MS analysis. Peaks in the peptide map profile were identified by comparing the observed accurate mass with the expected peptide mass for unmodified peptides. MS/MS data was collected to confirm the order of amino acid.

PTM or sequence variants were identified by a shift in the retention time and/or mass-to-charge ratio (m/z) of expected peptide. Exact location and nature of each PTM was identified by MS/MS. The levels of modification were quantitated by peak area integration of the extracted ion chromatograms. The results for PTM were expressed as the percentage of total peak area for unmodified and modified peptides.

Additionally, peptide map analysis with Glu-C enzyme was also performed to supplement the gaps in the MS/MS sequence coverage from trypsin map and to identify and quantitate glycation on Lys residues. Trypsin cleaves on the C-terminal side of Lys residues, and it is not considered ideal for identification and quantitation of Lys-glycation. Conversely, Glu-C enzyme cleaves on the C-terminal side of Glu and doesn't interfere with identification and quantitation of Lys-glycation. For Glu-C peptide mapping, a procedure similar to trypsin mapping was used. Product 1 was diluted in denaturing solution, reduced with dithiothreitol, alkylated with sodium iodoacetate, and buffer exchanged into digestion buffer prior to digestion with Glu-C endopeptidase. Resulting peptides were separated by RP-UPLC using a C18 column. UV absorbance was monitored at 214 nm and peptides were identified by in-line MS and MS/MS analysis. Peaks in the peptide map profile were identified by comparing the observed accurate mass with the expected peptide mass for unmodified peptides. MS/MS data was collected to confirm the order of amino acid. The levels of glycation were quantitated by peak area integration of the extracted ion chromatograms. The results for PTM were expressed as the percentage of total peak area for unmodified and modified peptide.

(c) Results

Figure 3:
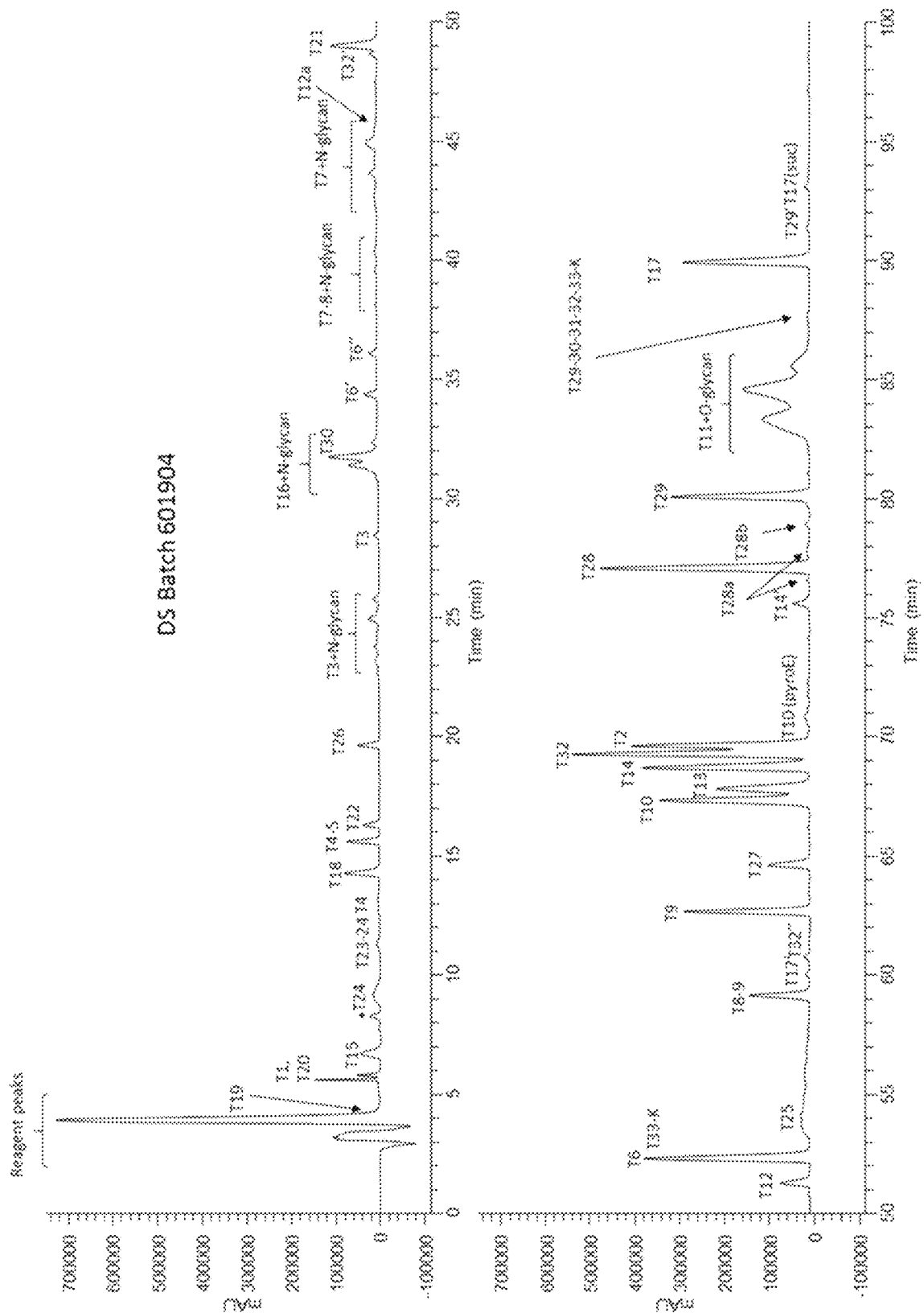
Figure 4:
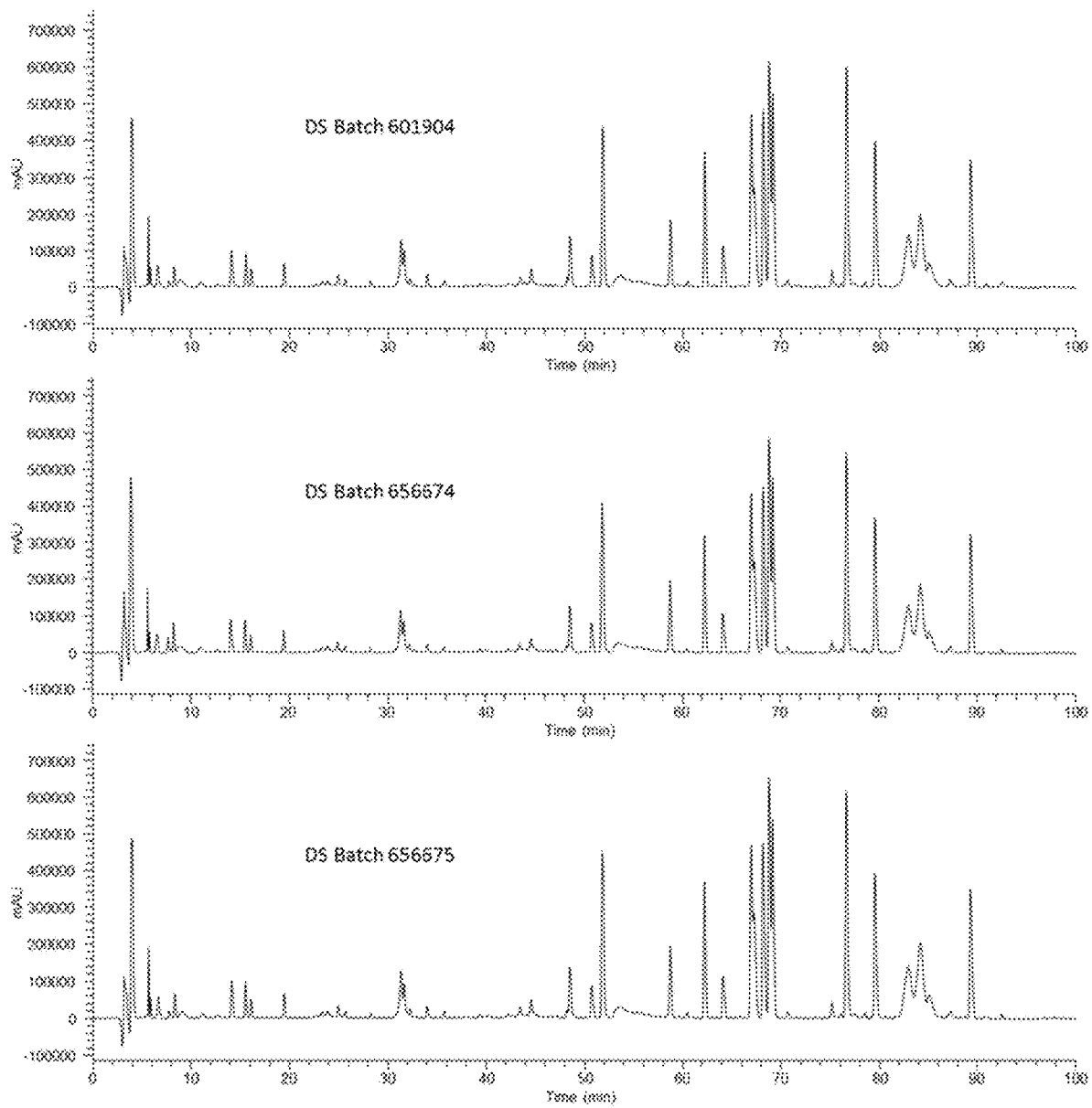
Figure 5:
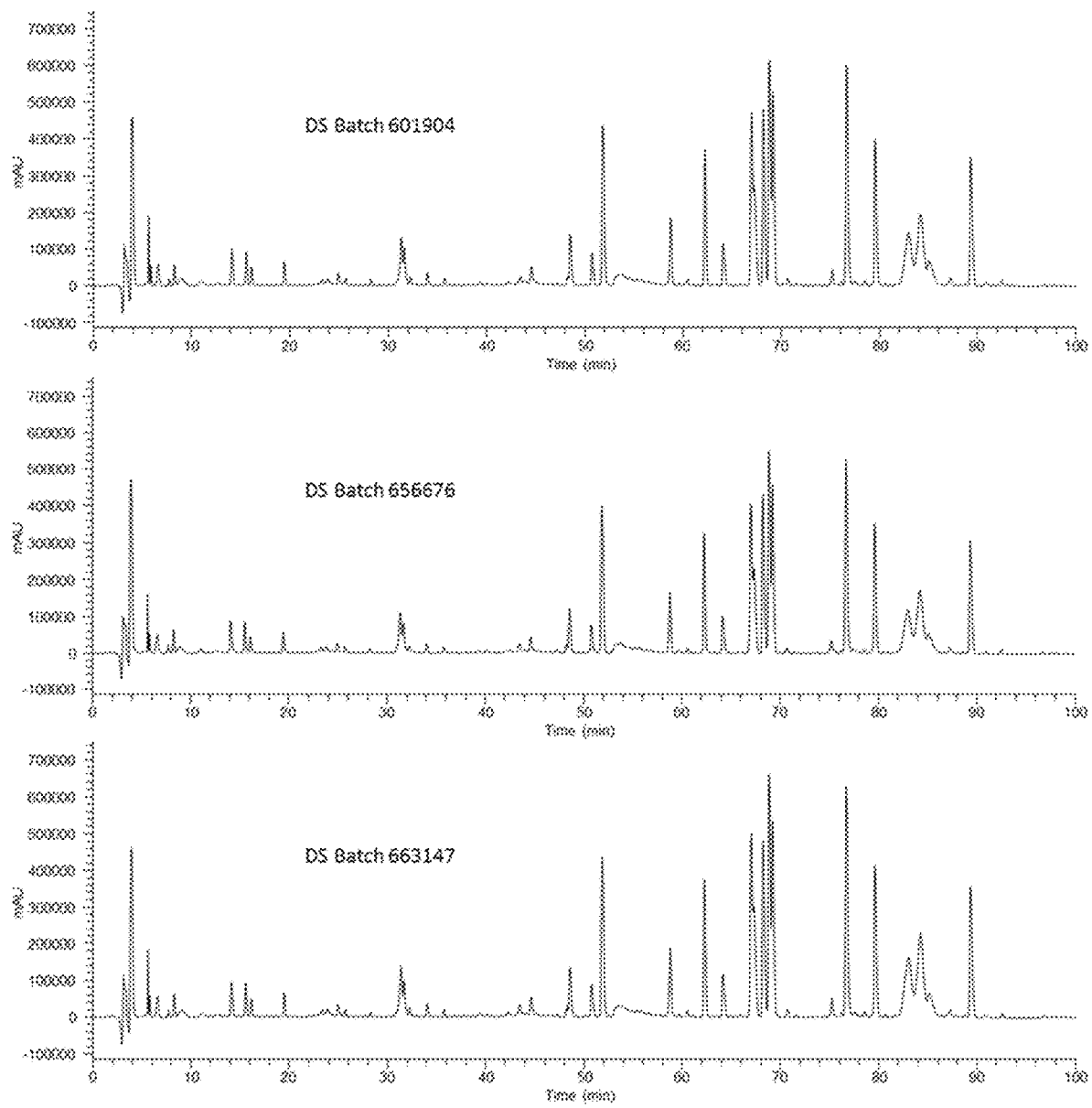

Results from in-depth characterization of Product 1 is presented in FIGS. 3-5 and summarized in Table 1.

TABLE 1

| Analysis | Results |
| --- | --- |
| Sequence Coverage (DS batch A1) | The coverage of digested peptides from trypsin map was 100% by mass spectrometry. MS/MS sequence coverage from trypsin map was about 89%, and it was further increased using Glu-C map to 93%. |
| Sequence Variants (DS batch A1) | Sequence variants were identified as Pro to Ala substitutions. Most prolines in the Product 1 sequence showed about 0.3% Ala variant. |
| Amino Acid Modifications (DS batch A1) | Low levels of N-terminal pyroE, C-terminal proline amidation, Asn-deamidation, Asp-isomerization and Met-oxidation were observed. The levels and sites of PTMs observed at levels ≥0.3% are listed in Table 2. |

| Sub-sections | Results |
| --- | --- |
| Product Quality Consistency (DS batches A1, A2, A3, A4 and A5) | One clinical DS and 4 PPQ DS batches showed similar peptide map profiles. The levels of sequence variants were consistent across all batches. The levels of N- and C-terminal heterogeneity, deamidation, isomerization, oxidation and glycation were also consistent (Table 3) |

Sequence Variants

Amino acid sequence variants result from gene sequence variant or unintended amino acid substitution during protein expression. Trypsin peptide map data were also evaluated for the presence of sequence variants. Single base pair substitutions were searched using biopharmafinder software and results were evaluated to differentiate true positives from false positives. Primarily, Pro-to-Ala substitutions were observed. Almost all prolines residues were substituted by alanine at levels ranging from 0.2% to 0.6%. Levels of all Pro-to-Ala substitutions were added and the sum was divided by the total number of prolines in the molecule to obtain the overall average of Pro-to-Ala substitutions per molecule. No other amino acid variants were observed at levels >0.1%. The average levels of Pro-to-Ala substitutions for DS batches A1 were 0.3%. The sequence variants were limited to substitution of only proline residues and all proline residues appear susceptible to substitution with alanine.

Consistent with the data for DS batch A1 the Pro-to-Ala sequence variants were observed in all batches. Almost all prolines residues were substituted by alanine at levels ranging from 0.2% to 0.9%. Levels of all Pro-to-Ala variants were added, and the sum was divided by the total number of proline residues in the molecule to obtain overall average of Pro-to-Ala variants per molecule. The average levels for Pro-to-Ala variants for DS batches A1, A2, A3, A4, and A5 were 0.3%, 0.4%, 0.5%, 0.3, and 0.5% respectively. No other amino acid variants were observed at levels >0.1%.

Post-Translational Modifications

Various post-translational modifications, including N- and C-terminal variants, Asn-deamidation, Asp-Isomerization, Met-Oxidation were observed in Product 1 batch A1. The relative levels were quantitated from extracted ion chromatograms by dividing the peak area for all the modified forms of peptide with a total peak area of modified and unmodified peptides. The results are summarized in Table 2. The PTM in the ECD region of the protein are highlighted in bold font.

TABLE 2

| Attribute | Relative Levels (%) |
| --- | --- |
| N-terminal pyroE | 0.9 |
| C-terminal (Lys + amidated proline) | 4.6 |
| C-terminal desLys | 95.4 |
| C-terminal Pro amidation | 2.0 |
| Asn203 deamidation | 3.7 |
| Asn 249/Gln250 deamidation | 0.6 |
| Asn272/277 deamidation | 5.2 |
| Asp55/56/57 isomerization | 0.6 |
| Asp168 isomerization | 0.4 |
| Asp 289 isomerization | 0.4 |
| Met140 oxidation | 1.2 |
| Met246 oxidation | 0.3 |
| Met316 oxidation | 0.8 |
| Lys134/136 glycation | 0.4 |
| Lys208/210/214 | 0.3 |

The relative levels of PTM were quantitated from extracted ion chromatograms by dividing the peak area for all the modified forms of peptide with a total peak area of modified and unmodified peptides. The results are presented in Table 3. Low levels of PTM including, N- and C-terminal variants, Asn-deamidation, Asp-isomerization, Met-oxidation, and Lys-glycation were observed in all PPQ batches of Product 1. The levels were consistent among all batches.

TABLE 3

| | Relative Levels (%) | | | | |
| --- | --- | --- | --- | --- | --- |
| Attribute | A1 | A2 | A3 | A4 | A5 |
| N-terminal pyroGlu | 0.9 | 1.0 | 1.1 | 1.0 | 1.0 |
| C-terminal des-Lys | 95.4 | 95.0 | 95.2 | 95.0 | 95.1 |
| C-terminal Pro amidation | 2.0 | 2.5 | 2.5 | 2.3 | 2.9 |
| Asn203 deamidation | 3.7 | 3.8 | 3.8 | 3.6 | 3.9 |
| Asn 249/Gln250 deamidation | 0.6 | 0.6 | 0.6 | 0.6 | 0.6 |
| Asn272/277 deamidation | 5.2 | 5.5 | 6.1 | 5.3 | 5.5 |
| Asp55/56/57 isomerization | 0.6 | 0.6 | 0.6 | 0.5 | 0.6 |
| Asp168 isomerization | 0.4 | 0.4 | 0.4 | 0.4 | 0.4 |
| Asp 289 isomerization | 0.4 | 0.4 | 0.4 | 0.4 | 0.4 |
| Met140 oxidation | 1.2 | 1.2 | 1.1 | 1.2 | 1.2 |
| Met246 oxidation | 0.3 | 0.2 | 0.2 | 0.3 | 0.3 |
| Met316 oxidation | 0.8 | 0.7 | 0.6 | 0.7 | 0.7 |
| Lys134/136 glycation | 0.4 | 0.4 | 0.4 | <0.3 | 0.4 |
| Lys208/210/214 glycation | 0.3 | 0.4 | 0.3 | 0.3 | 0.4 |

N- and C-Terminal Heterogeneity

Product 1 contains a Glu at the N-terminal and the level of N-terminal pyroGlu was 0.9%. The impact of pyroGlu on structure function properties of Product 1 was further studied using stressed samples.

Product 1 is an IgG-based fusion protein that contains a conserved Fc portion of the IgG heavy chain. C-terminal modifications were also observed in Product 1. The C-terminal residues of Product 1 were either Pro333, Gly334 or Lys335 and the levels of C-terminal ending in Lys335, Gly334 or amidated Pro333 were 2.6%, 95.4% and 2.0%, respectively. Combined total of minor species containing C-terminal Lys or amidated proline was 4.6%.

Deamidation

Low levels of deamidation were observed at various Asn residues of Product 1 including Asn203 (3.7%), Asn 249/Gln250 (0.6%) and Asn272/277 (5.2%). Deamidation observed at other sites were ≤0.3%. Results are summarized in Table 3.

Isomerization

Low levels of isomerization were observed at various Asp residues of Product 1 including Asp55/56/57 (0.6%), Asp168 (0.4%), and Asp 289 (0.4%). Isomerization observed at other sites were ≤0.3%. Results are summarized in Table 3.

Oxidation

Oxidation is another common degradation pathway in proteins. Methionine, tryptophan, cysteine, histidine, and tyrosine residues can undergo oxidation with exposure to oxidizing agents. Low levels of oxidation were observed at three Met residues of Product 1. The relative levels of oxidation of Met140 and Met316 were 1.2% and 0.8%, respectively. The level at Met246 was <0.3%. Results are summarized in Table 3.

Other amino acids including cysteine, tyrosine and tryptophan can also get oxidized by exposure to different wavelengths of light. Tryptophan is especially sensitive to light at 280-305 nm range. Oxidation of tryptophan results in the formation of both hydroxytryptophan and kynurenine derivatives. Like methionine oxidation surface exposure and solvent accessibility play an important role in susceptibility of a given tryptophan in a protein. Levels of tryptophan oxidation in Product 1 were very low, with no tryptophan showing levels >0.1%.

Glycation

Glycation occurs due to chemical reaction of a reducing sugar with the amine group in the side chain of lysine residues. Low levels of glycation were observed at various Asn residues of Product 1 including Lys134/136 (0.4%) and Lys208/210/214 (0.3%). All these residues are in the conserved Fc region. Glycation levels observed at other sites were ≤0.3%. Results are summarized in Table 3. The impact of glycation on structure-function properties of Product 1 was further studied using stressed samples.

N- and O-Glycosylation

Product 1 contains three consensus sequences (Asn-Xxx-Ser/Thr) for N-linked glycosylation and a few potential sites for O-glycosylation.

Product Quality Consistency

To demonstrate consistency of product quality, primary structure characterization by peptide map analyses was also performed on 4 DS batches from the PPQ campaign, including A2, A3, A4, and A5. The trypsin map profiles for PPQ batches is presented in FIG. 4 and FIG. 5. The profiles for all batches were nearly identical in terms of number of peaks, peak shape, retention times, and relative peak intensities.

Three DS batches, A6, A7 and A8, were also characterized by this approach.

9.3 Example 3: A Charge Heterogeneity Characterization of Product 1

(a) Introduction

A charge heterogeneity characterization of Product 1 by imaged capillary iso-electrofocusing (icIEF) method was performed on representative drug substance (DS) batch A1.

(b) Strategy and Methods

To evaluate consistency of product quality, four DS batches from the process performance qualification (PPQ) campaign, A2, A3, A4, and A5, were also characterized for charge heterogeneity by icIEF.

The charge heterogeneity of Product 1 drug substance batch A1 was characterized by icIEF.

In addition, Product 1 treated with sialidase was also evaluated to better understand the primary source of charge heterogeneity and study its impact on the structure-function properties of Product 1.

(c) Results

A summary of charge heterogeneity characterization of Product 1 is presented in Table 4.

TABLE 4

| Sub-section | Results |
| --- | --- |
| Charge heterogeneity Characterization by icIEF (DS batch A1) | Multiple peaks were observed in pI range 3.8 to 5.4. The profile was divided into 5 groups from Group 1 (most acidic) through Group 5 (most basic). Relative level of each group is presented in Table 5. |
| Extended Characterization using Exoglycosidase Enzymes (DS batch A1) | Results confirmed that majority of charge heterogeneity in Product 1 was due to sialic acid heterogeneity on N- and O-glycans. Desialylated Product 1 showed one major peak at pI 5.6, corresponding to Product 1 with zero net charge. The levels of acidic, main, and basic peaks were 3.0%, 88.0% and 9.0%. The levels for acidic peaks correlate well with the small levels of deamidation observed on various Fc Asn residues. The levels of basic peaks correlate well with the small levels of unclipped C-terminal Lys and amidation of C-terminal Pro. The desialylated Product 1 retains full biological function as no loss potency of GDF11 binding or FcRn was observed. |
| Product Quality Consistency (DS batches A1, A2, A3, A4 and A5) | Peak profile for all batches were highly similar. Relative levels of each group were consistent for 1 clinical and 4 PPQ batches (Table 8). |

Charge Heterogeneity Characterization of Product 1 by icIEF ichEF separates proteins based on the net surface charge and provides an effective method for quantitating acidic and basic species. As shown in FIG. 6, the icIEF profile of Product 1 is very complex and shows multiple peaks in the pI range of 3.8 and 5.4. For quantitative analysis, the icIEF peaks are integrated into five groups and relative level of each group is reported. Out of 5 groups, Group 1 consists of the most acidic forms and Group 5 consists of the most basic forms. The relative levels of each group are summarized in Table 5.

TABLE 5

| Attribute (icIEF Group) | Relative Levels (%) |
|---|---|
| Group 1 | 3.7 |
| Group 2 | 32.6 |
| Group 3 | 20.7 |
| Group 4 | 35.2 |
| Group 5 | 7.7 |

Identification of Primary Source of Product 1 Charge Heterogeneity

Figure 7:
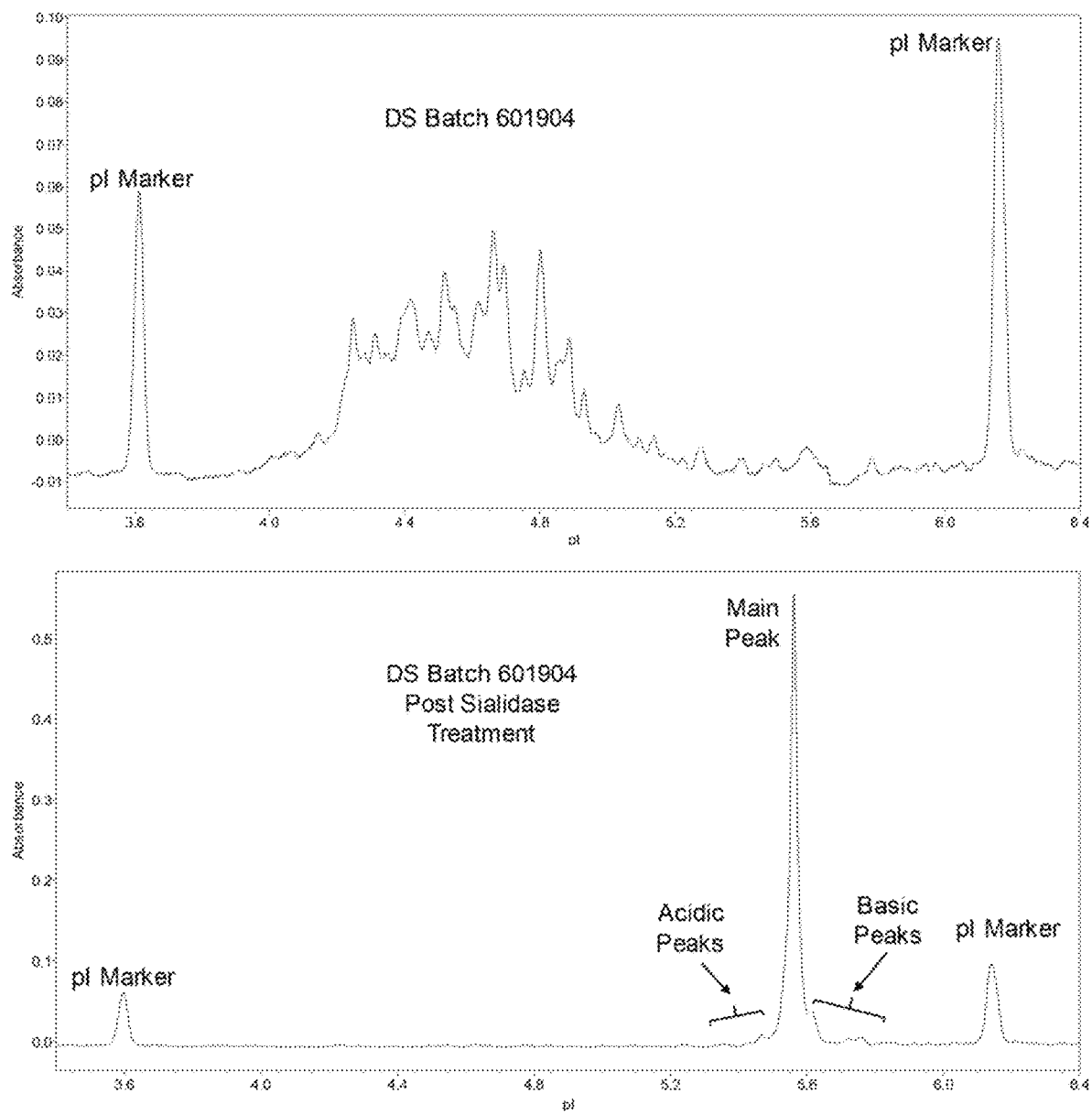

Product 1 contains significant heterogeneity due to number of sialic acid on N- and O-glycans. To confirm that hypothesis, Product 1 was treated with sialidase and analyzed by icIEF. A comparison of icIEF profiles of DS batch A1 before and after sialidase treatment is presented in FIG. 7. Removal of sialic acids removed most of charge heterogeneity complexity and significantly simplified the icIEF profile. Desialylated Product 1 showed one major peak at pI 5.6, corresponding to Product 1 with zero net charge. The peak areas were integrated, and relative peak areas of main peak, total acidic peak and total basic peaks were quantified. After removing sialic acid heterogeneity, Product 1 DS batch contained 3.0% acidic peaks, 88.0% main peak, and 9.0% basic peaks.

The peptide map analysis results for desialylated and control Product 1 are presented in Table 6.

TABLE 6

| Attribute | DS A1 Control | Desialylated DS A1 |
|---|---|---|
| N-terminal pyroGlu (%) | 0.8 | 1.0 |
| C-terminal des-Lys (%) | 2.0 | 2.5 |
| C-terminal proline amidation (%) | 2.4 | 2.3 |
| Met140 oxidation (%) | 2.2 | 2.4 |
| Met246 oxidation (%) | 0.7 | 0.6 |
| Met316 oxidation (%) | 1.0 | 0.9 |
| Asn203 deamidation (%) | 0.8 | 0.9 |
| Asn213 deamidation (%) | ND | ND |
| Asn272/277 deamidation (%) | 3.8 | 2.7 |
| Asp55/56/57 isomerization (%) | 1.7 | 1.0 |
| Asp289 isomerization (%) | 0.3 | 0.6 |

ND = Not detected.

This distribution of acidic and basic peaks correlated well with the PTM observed by peptide mapping. Based on peptide map analysis, Product 1 contains deamidation, an acidic variant, at levels about 2% to 3% combined on various sites per chain, which converts to about 5% acidic variants per Product 1 molecule. Similarly, the levels of basic variants, including C-terminal Lys and C-terminal Pro amidation were about 4% to 5%, which converts to about 9% basic variant per Product 1 molecule. Most other modifications are not expected to impact the surface charge to substantially alter the charge heterogeneity profile. These modifications levels correlate well with the observed values for acidic (3.0%) and basic variants (9.0%) by icIEF analysis of sialidase treated Product 1.

To study the impact of primary source of charge heterogeneity on the biological function, desialylated Product 1 molecule was also analyzed by potency assay and FcRn binding assay. The results for these assays are summarized in Table 7.

TABLE 7

| Assay | DS A1 Control | De-sialylated DS A1 |
|---|---|---|
| Potency by In-Vitro Reporter Gene Assay (%) | 104 | 97 |
| FcRn binding (%) | 99 | 95 |

No loss of biological function was observed due to removal of sialic acids. The potency and FcRn binding of desialylated Product 1 were comparable to the control Product 1 sample, not treated with sialidase.

Product Quality Consistency

To demonstrate consistency of product quality, charge heterogeneity characterization by icIEF analysis was also performed on four Product 1 batches from the PPQ campaign, A2, A3, A4 and A5.

Three DS batches, A6, A7 and A8, were also characterized by this approach.

Figure 8:
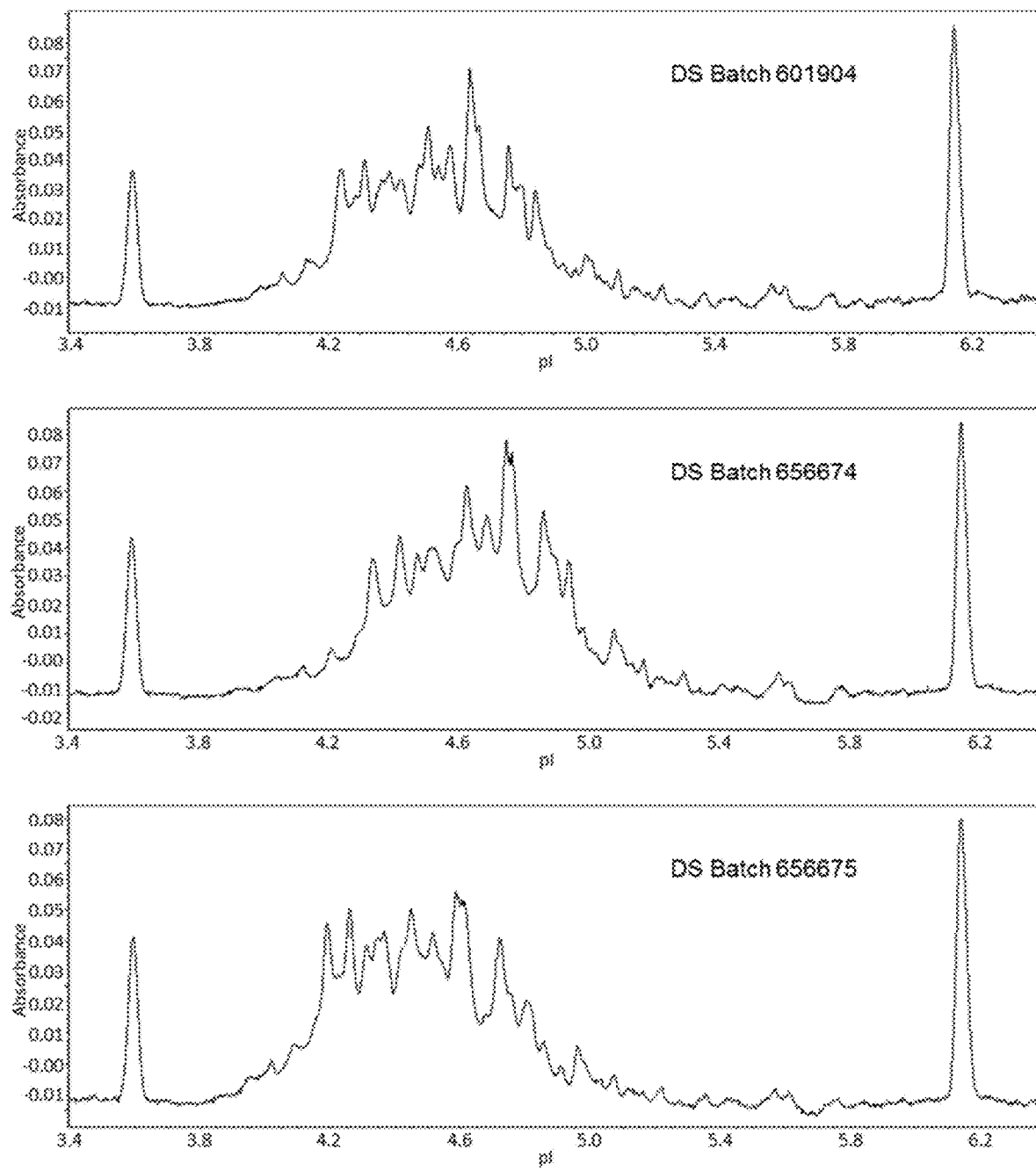
Figure 9:
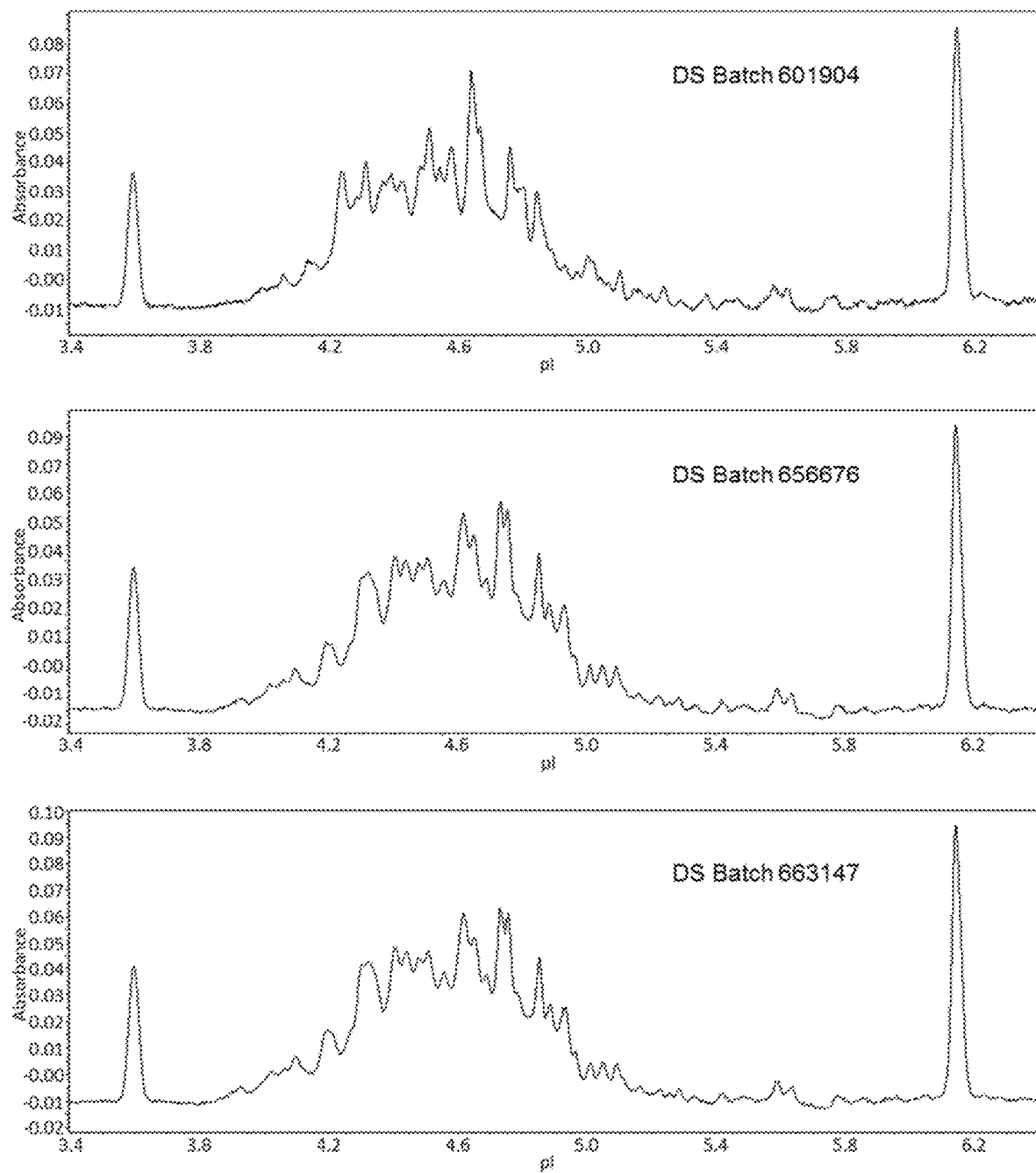

Results for icIEF analysis are presented in FIG. 8 and FIG. 9 and summarized in Table 8.

TABLE 8

| Attribute (icIEF Group) | Relative Levels (%) | | | | |
|---|---|---|---|---|---|
| | A1 | A2 | A3 | A4 | A5 |
| Group 1 | 3.7 | 3.4 | 3.9 | 6.0 | 6.7 |
| Group 2 | 32.6 | 33.4 | 35.3 | 36.9 | 38.3 |
| Group 3 | 20.7 | 21.3 | 22.4 | 22.1 | 21.8 |
| Group 4 | 35.2 | 35.4 | 32.6 | 29.6 | 28.1 |
| Group 5 | 7.7 | 6.5 | 5.9 | 5.6 | 5.1 |

The results for all batches were consistent. Each batch showed a complex profile with multiple peaks in the pI range 3.8 to 5.4. Although, batches showed some shift in pI due to assay-to-assay variability and batch-to-batch heterogeneity of sialic acids, overall range of pI and peak pattern were similar. The relative levels of 5 groups of peaks were also consistent among all batches.

9.4 Example 4: Structure-Function Relationships of Product 1

Structure-function studies of Product 1 were performed to understand the degradation pathways and to assess the criticality of structural changes. Structural changes were introduced by forced degradation and evaluated by structural and functional characterization. In addition, the functional impact of structural changes due to glycans were evaluated by treating Product 1 with exoglycosidase.

Clinical DS batch A9 was used for most structure-function studies, except to study structure-function relationships due to glycan changes, for which DS batch A1 was used. Multi-point forced degradation studies were designed to introduce sufficient degradation to study its impact on the biological activity. It should be noted that forced degradation conditions far exceeded the conditions Product 1 is expected to experience during manufacturing process. In addition, three glycan variants were generated by removal of the terminal sialic acid, removal of O-glycans, removal of N-glycans.

All forced degraded and deglycosylated samples were characterized for primary structure changes by peptide mapping, size heterogeneity changes by size exclusion chromatography (SEC), capillary electrophoresis sodium dodecyl sulfate (CE-SDS (reducing and non-reducing)), and charge heterogeneity changes by icIEF. Functional impact of these changes was evaluated by reporter gene assay and FcRn binding alphaELISA.

The results of the structure function analysis are summarized in Table 9.

TABLE 9

| Study | Results |
| --- | --- |
| Stress Type 1 | The following changes due to Type 1 Stress of Product 1 were detected:<br>Asp isomerization and Asn deamidation by peptide mapping<br>LMWS by reduced CE-SDS<br>Potency by Bioassay<br>A linear correlation between Asp Isomerization and bioactivity was observed. A 20% loss in potency was correlated to about 7.7% isomerization at Asp55/56/57. |
| Stress Type 2 | Following changes due to Type 2 Stress of Product 1 were detected:<br>HMWS and LMWS by SEC<br>LMWS by reduced CE-SDS<br>Basic shift in charge profile by icIEF<br>No impact on biological function was observed<br>Reduced CE-SDS method was significantly more sensitive to detect the LMWS than SEC. A linear correlation between HMWS levels and basic shift was observed. |
| Stress Type 3 | Following changes due to Type 3 Stress of Product 1 were detected:<br>Asn deamidation and N-terminal pyroGlu by peptide mapping<br>LMWS by reduced CE-SDS<br>Acidic shift in charge profile by icIEF<br>Potency by Bioassay<br>A linear correlation between Asn deamidation and Stress Type 3 was observed. In addition, a correlation between LMWS and bioactivity was also observed. A 20% loss in potency was correlated to about 9.0% LMWS by reduced CE-SDS. |
| Stress Type 4 | Following changes due to Type 4 Stress of Product 1 were detected:<br>Met oxidation by peptide mapping<br>Slight basic shift in charge profile by icIEF<br>FcRn binding by alphaELISA<br>Met140 residue was most sensitive to chemical oxidation by Type 4 Stress. A linear correlation between Met140 oxidation loss of FcRn binding was observed. A 20% loss in FcRn binding was correlated to about 18.5% Met140 oxidation. |
| Stress Type 5 | Following changes due to Type 5 Stress of Product 1 were detected:<br>Met and Trp oxidation by peptide mapping<br>HMWS by SEC<br>HMWS by non-reduced and reduced CE-SDS<br>Slight basic shift in charge profile by icIEF<br>Loss of potency by Bioassay<br>Change in FcRn binding by alphaELISA<br>Met140 residue was most sensitive to oxidation by Stress Type 5. SEC method was most sensitive to detect HMWS. A linear correlation between bioactivity and HMWS by SEC was observed. A 20% loss in bioactivity was correlated with about 5.2% HMWS by SEC. |
| Type 6 Stress | Following changes due to Type 6 Stress of Product 1 were detected:<br>Lys Glycation by Glu-C peptide mapping<br>Acidic shift in the icIEF profile<br>Loss of potency by Bioassay<br>Lys50 in the ECD was identified as most sensitive residue for glycation. A 20% loss in bioactivity was correlated with about 20% glycation on Lys50.<br>Loss in FcRn binding was attributed to method induced oxidation of Met due to Type 6 Stress. |
| Exoglycosidase Treatment to Remove Sialic Acid or O-Glycans or N-Glycans | Following changes due to deglycosylation of Product 1 were detected:<br>Generation of new early eluting peaks or an increase in early eluting shoulder peak was observed due to removal of N-glycans.<br>Complex icIEF profile collapses to a simple profile with because of removal of sialic acid heterogeneity<br>No loss of bioactivity or FcRn binding was observed |

Further Structure-function characterization of mAbs were conducted to identify quality attributes that may affect antigen binding, Fc effector function, pharmacokinetics, immunogenicity and stability. Forced degradation studies of mAbs aid in the identification of certain quality attributes by studying the impact of post-translational modifications, e.g. oxidation, deamidation, isomerization, glycation and glycosylation on biological functions. Structure-function characterizations were performed by under conditions including, e.g., heat stress, high pH stress, low pH stress, oxidation stress, and glucose stress.

(a) Structure-Function Characterization by Heat Stress

The structure-function characterization by heat stress was carried out at 40° C. for 28 days. Modification of Asp residues located in the CDR region to isomerized form contributes to the potency loss. The results of Asp (including Asp55/56/57) isomerization percentages and corresponding potency percentages measured at different times are summarized in Table 10.

Figure 10:
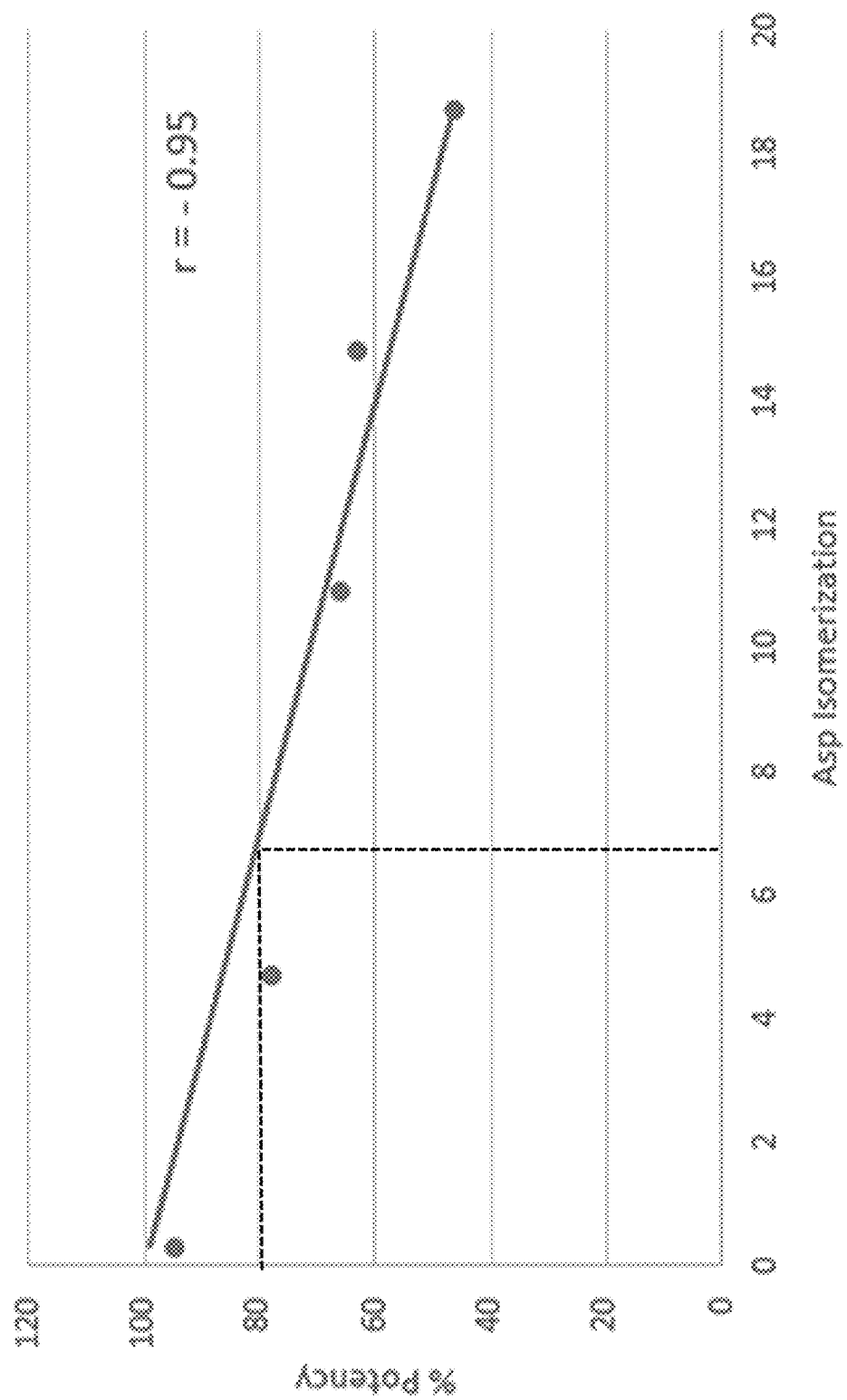

As shown in FIG. 10, a linear correlation between Asp isomerization and potency loss under heat stress was observed (r=−0.95). As calculated, a 20% loss in potency was correlated to about 5.6% Asp isomerization.

TABLE 10

| Heat Stress | Asp isomerization (%) | % Potency |
|---|---|---|
| Control | 0.3 | 95 |
| 40° C., 7 days | 4.7 | 78 |
| 40° C., 14 days | 10.9 | 66 |
| 40° C., 21 days | 14.8 | 63 |
| 40° C., 28 days | 18.7 | 46 |

(b) Structure-Function Characterization by High pH Stress

In the structure-function characterization by high pH stress, deamidation of Asn residues was most sensitive to high pH stress. The results of Asn (including Asn272/277) deamidation percentages, low molecular weight (LMW) percentages, and corresponding potency percentages measured at different times are summarized in Table 11.

Figure 11A:
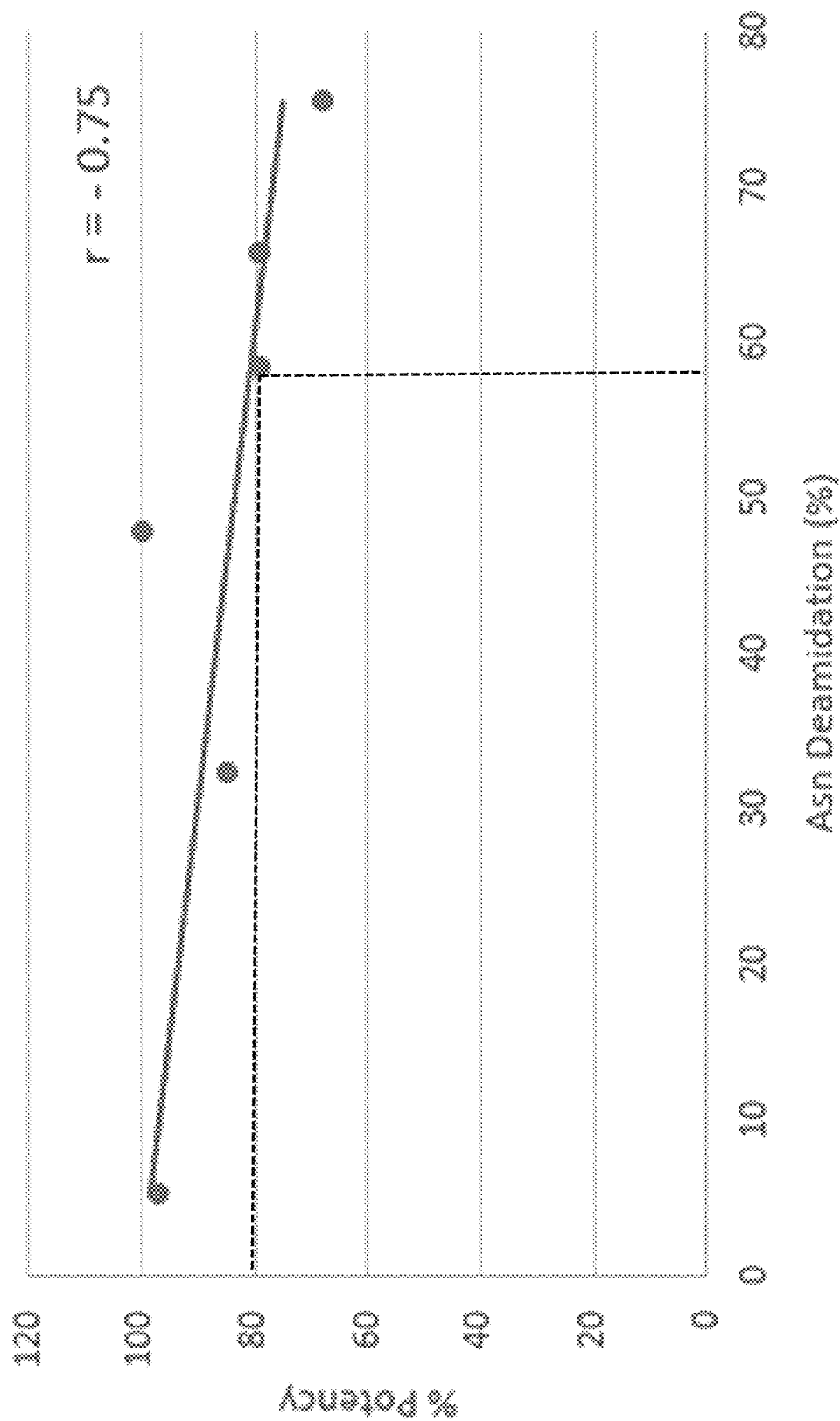
Figure 11B:
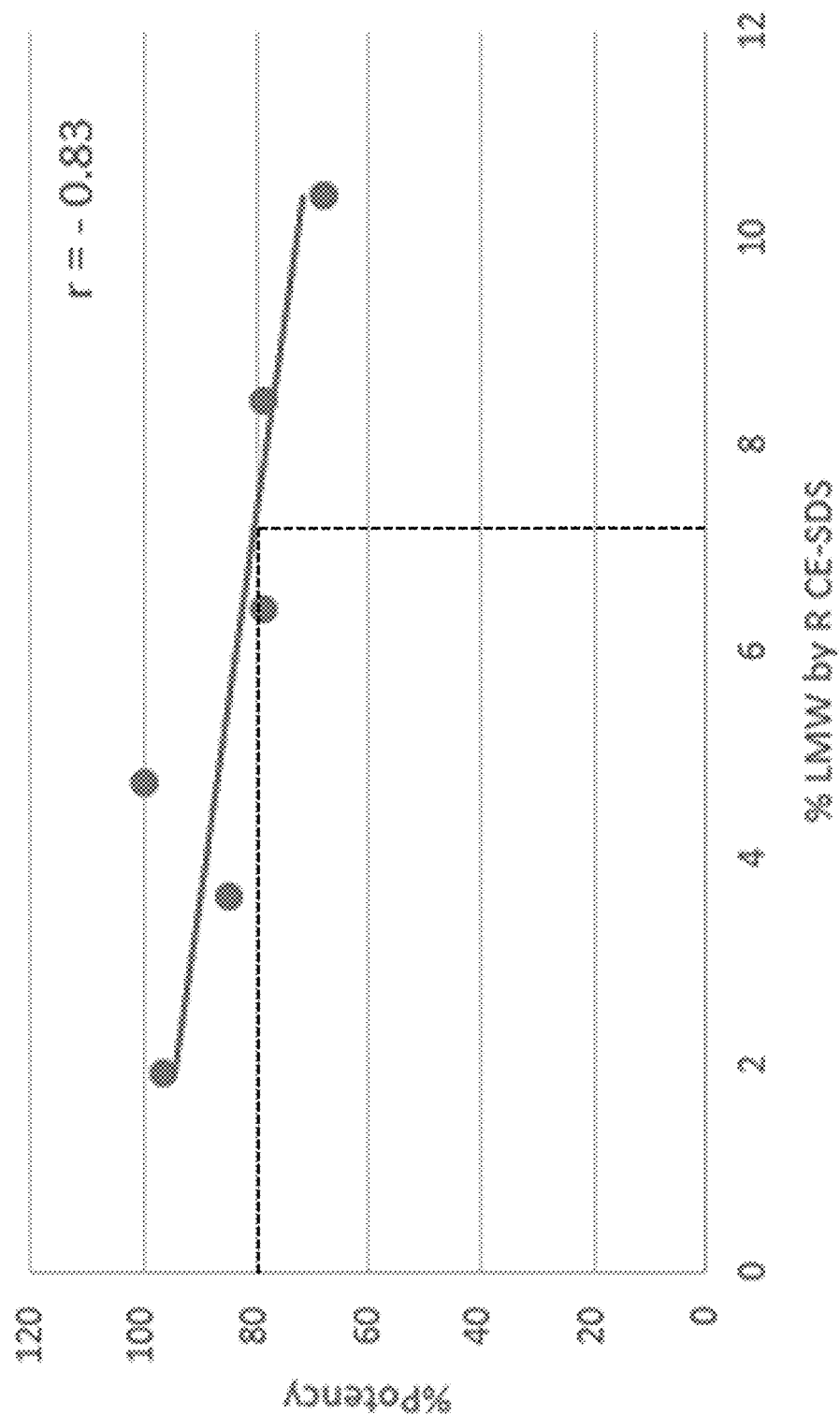

As shown in FIG. 11A, a linear correlation between Asn deamidation and potency loss under high pH stress was observed (r=−0.75). As calculated, a 20% loss in potency was correlated to about 60.6% Asn deamidation. In addition, as shown in FIG. 11B, a correlation between LMW percentage measured by reduced CE-SDS and potency loss was also observed (r=−0.83). As calculated, a 20% loss in potency was correlated to about 7.4% LMWS.

TABLE 11

| Days | % Potency | Asn residues Deamidation (%) | % LMWS |
|---|---|---|---|
| T0 | 97 | 5.2 | 1.9 |
| T4 | 85 | 32.4 | 3.6 |
| T8 | 100 | 47.7 | 4.7 |
| T12 | 79 | 58.4 | 6.4 |
| T16 | 79 | 65.6 | 8.4 |
| T22 | 68 | 75.4 | 10.4 |

(c) Structure-Function Characterization by Oxidation

Methionine residues located in the Fc region are known to have impact on the binding to FcRn receptor. The structure-function characterization by oxidation stress was carried out under the conditions of different tert-butyl hydroperoxide (tBHP) concentrations. The results of Met oxidation (at Met site 1 and at Met site 2) percentages and corresponding FcRn binding percentages measured at different tBHP concentrations are summarized in Table 12.

Figure 12A:
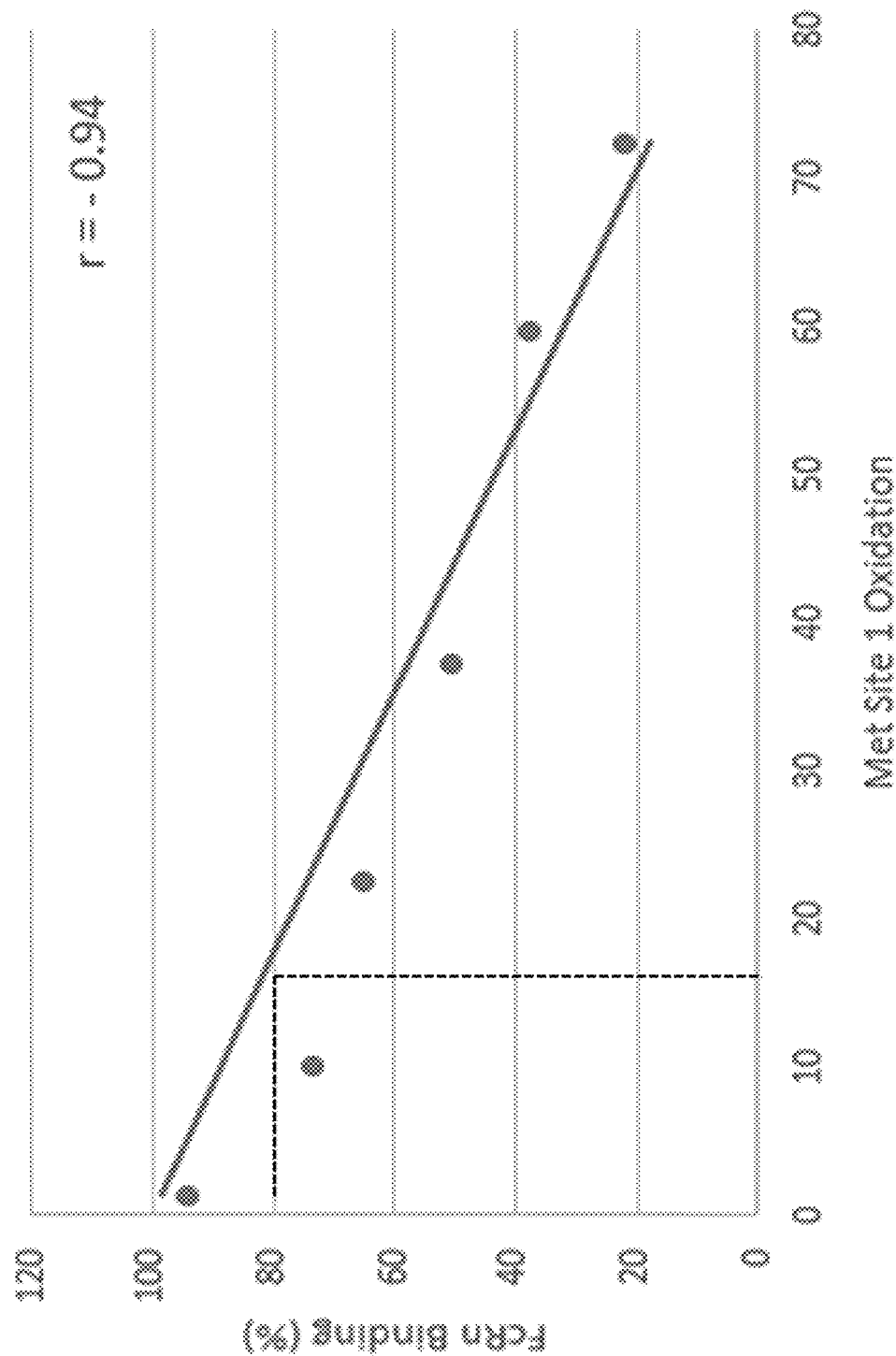
Figure 12B:
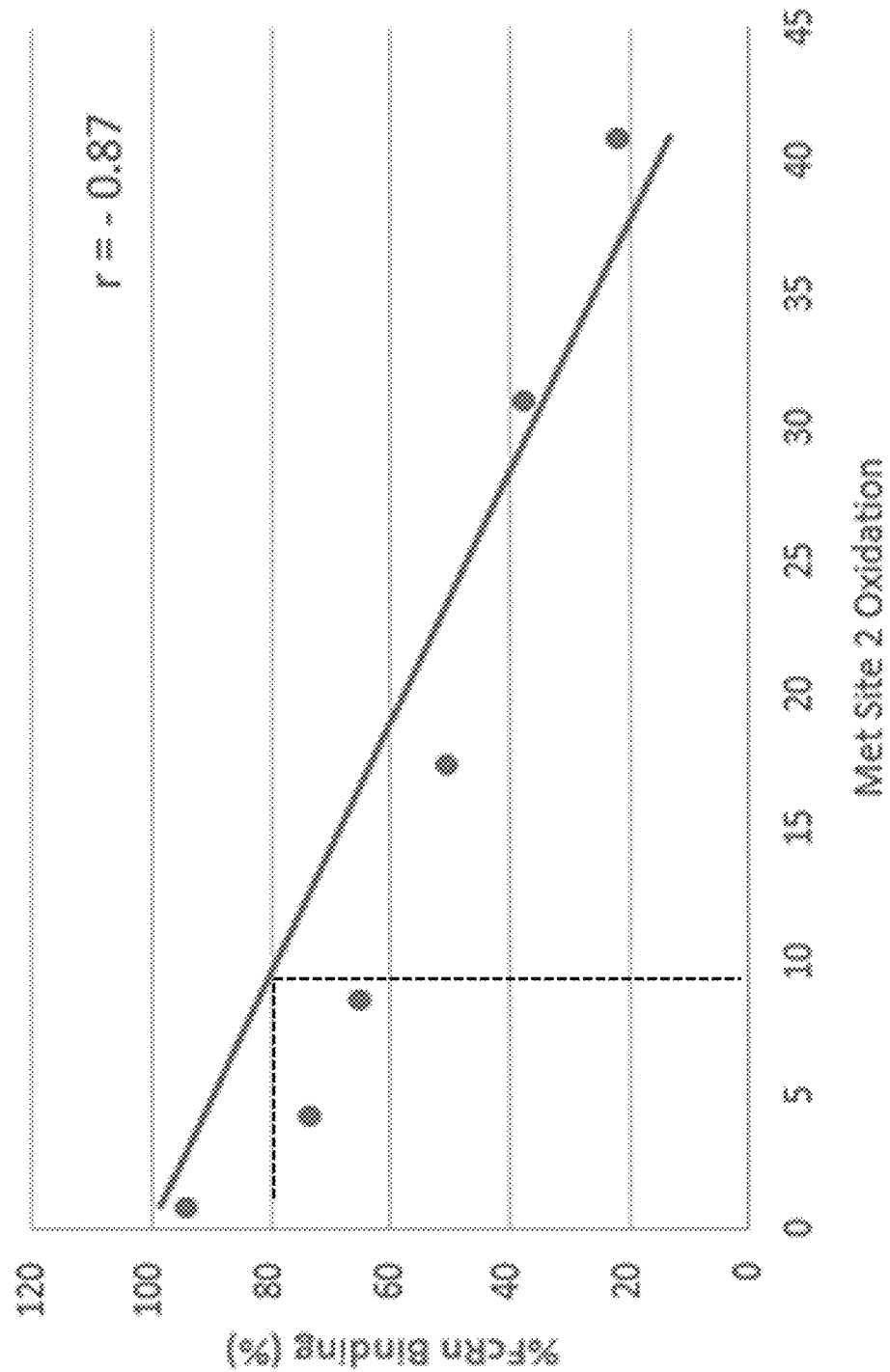

Met site 1 (Met140) residue was most sensitive to chemical oxidation by tBHP. As shown in FIG. 12A, a linear correlation between Met140 oxidation and loss of FcRn binding was observed (r=−0.94). As calculated, a 20% loss in FcRn binding was correlated to about 8.9% Met140 oxidation. In addition, as shown in FIG. 12B, a linear correlation between Met site 2 (Met316) oxidation and loss of FcRn binding was also observed (−0.87). As calculated, a 20% loss in FcRn binding was correlated to about 2.8% Met316 oxidation.

TABLE 12

| tBHP conc. | Met Site 1 oxidation (%) | Met site 2 oxidation (%) | FcRn binding (%) |
|---|---|---|---|
| Control | 1.3 | 0.8 | 94.3 |
| 2 mM | 10 | 4.2 | 73.7 |
| 5 mM | 22.5 | 8.5 | 65.2 |
| 10 mM | 37.2 | 17.4 | 50.5 |
| 20 mM | 59.6 | 31 | 37.5 |
| 30 mM | 72.3 | 40.9 | 21.9 |

(d) Structure-Function Characterization by Glucose Stress

Glycation of Lys residue located in the CDR region at higher amount of glucose stress contributes to the potency loss. The structure-function characterization by glucose stress was carried out under the conditions of different glucose concentrations. The results of Lys (including Lys208/210/214) glycation percentages and corresponding potency percentage measured at different glucose concentrations are summarized in Table 13.

Figure 13:
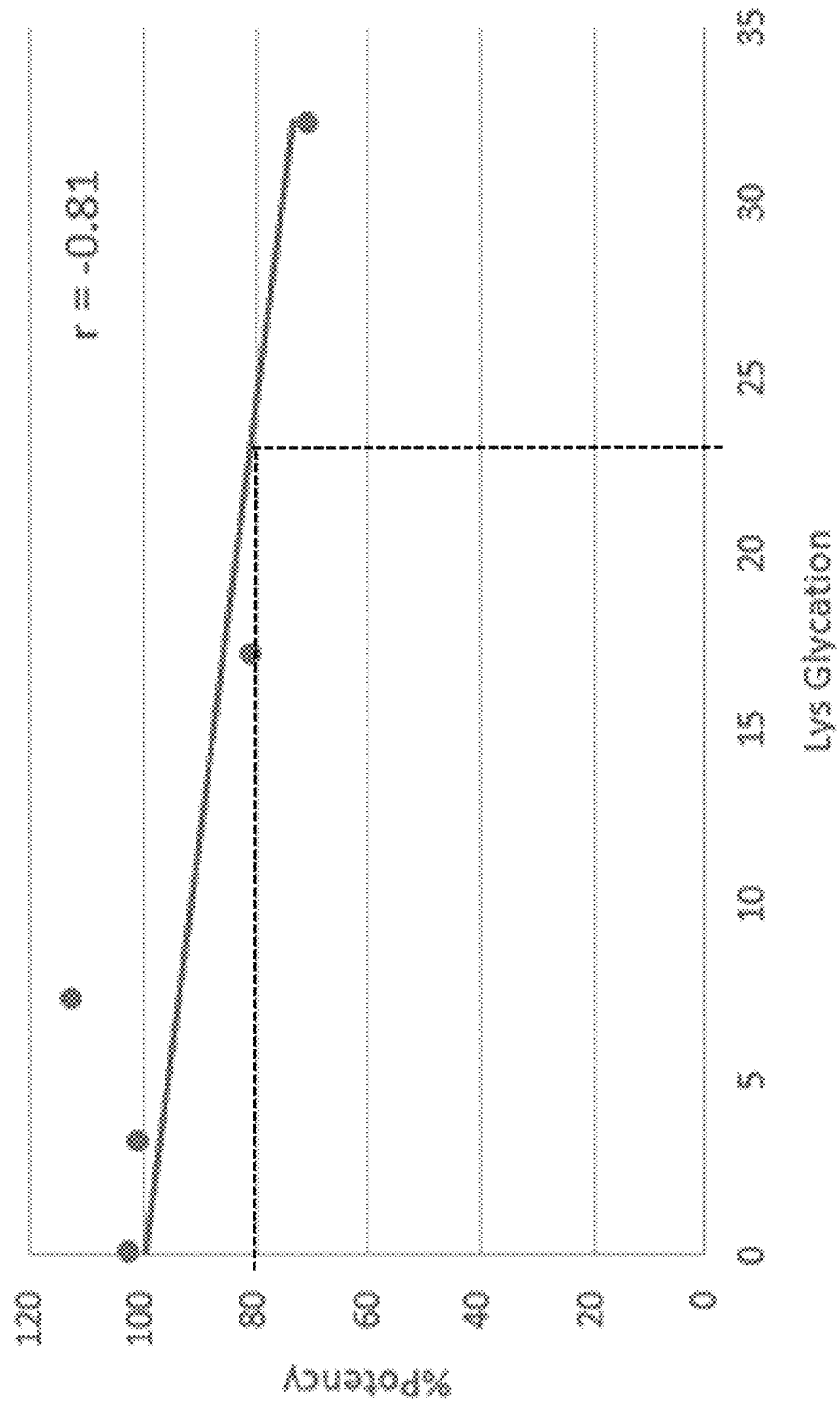
FIG. 13 illustrates increase of glycation of Lys residues in relation to potency loss under glucose stress. A linear correlation between the Lys glycation percentage and potency loss under glucose stress was observed (r=−0.81).

As shown in FIG. 13, a linear correlation between Lys glycation and potency loss under glucose stress was observed (r=−0.81). As calculated, a 20% loss in potency was correlated to about 23.9% Lys glycation.

TABLE 13

| Glucose Conc. (mM) | % Potency | Lys Glycation |
|---|---|---|
| Control | 103 | 0.1 |
| 50 | 101 | 3.3 |
| 100 | 113 | 7.3 |
| 250 | 81 | 17.1 |
| 500 | 71 | 32.3 |

(e) Structure-Function Characterization by Photo Stress

Formation of HMWS and other potential structural changes to the higher order structure of the molecule caused by light exposure contribute to the potency loss. The structure-function characterization by photo stress was carried out under different levels of exposures. The results of high molecular weight species (HMWS) percentages and corresponding potency percentages measured under different exposure levels are summarized in Table 14.

Figure 14:
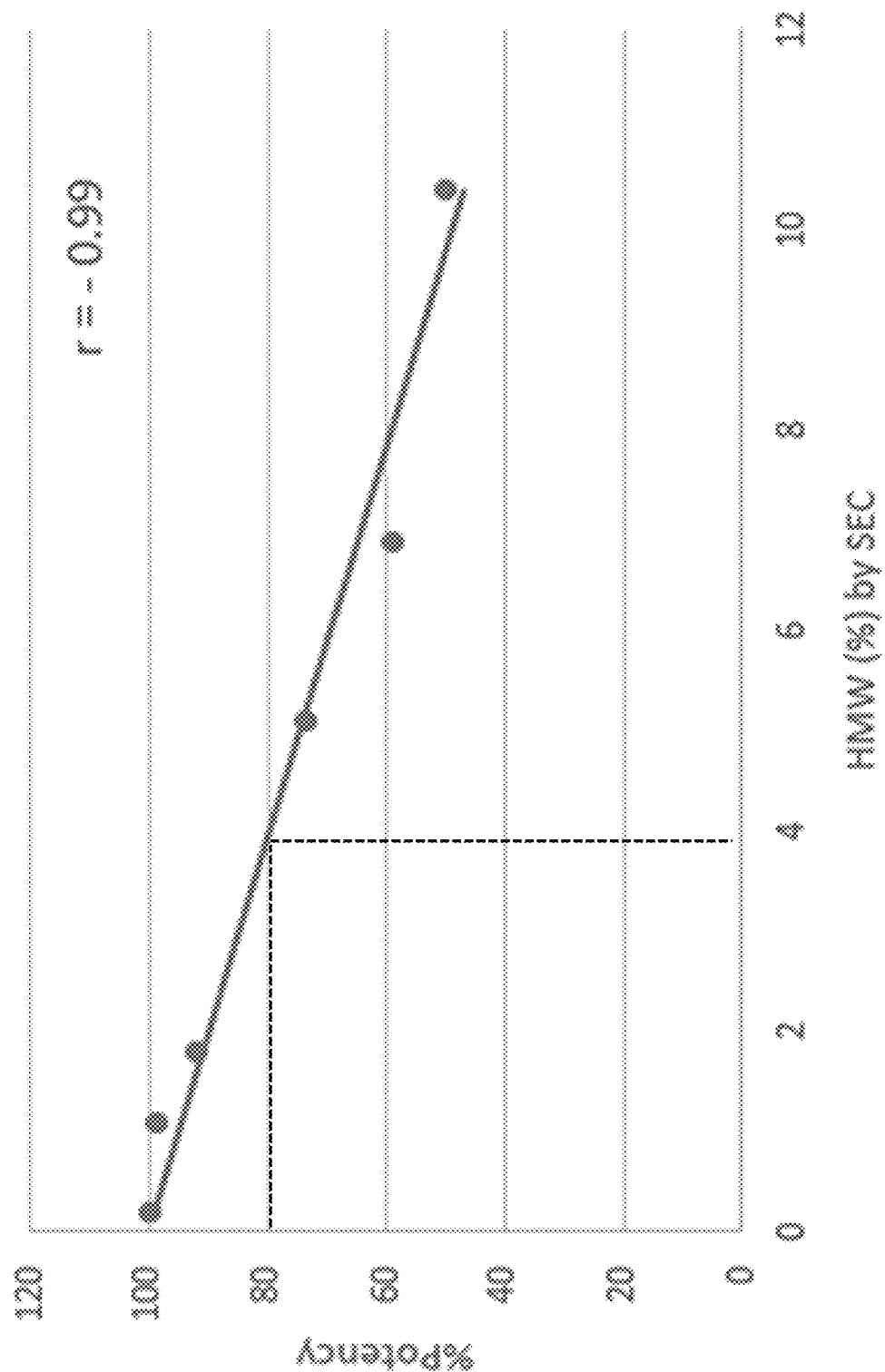
FIG. 14 illustrates increase of high molecular weight species (HMWS) in relation to potency loss under photo stress. A linear correlation between HMWS percentage measured by size-exclusion chromatography (SEC) and potency loss under photo stress was also observed (r=−0.99).

As shown in FIG. 14, a linear correlation between HMWS percentage measured by SEC and potency loss under photo stress was observed (r=−0.99). As calculated, a 20% loss in potency was correlated to about 4.1% HMWS.

TABLE 14

| Photo Stress | HMWS (%) | % Potency |
|---|---|---|
| Dark CTL | 0.2 | 100 |
| 0.25 × ICH | 1.1 | 99 |

TABLE 14-continued

| Photo Stress | HMWS (%) | % Potency |
|---|---|---|
| 0.5 × ICH | 1.8 | 92 |
| 1.0 × ICH | 5.1 | 74 |
| 1.5 × ICH | 6.9 | 59 |
| 2.0 × ICH | 10.4 | 50 |

*Data normalized with the Dark CTL

9.5 Example 5: Biological Characterization of Product 1

(a) Introduction

The biological function characterization of Product 1 was performed on primary reference standard PRSA4, prepared from representative drug substance (DS) batch A4. Product 1 was characterized for biological function by bioassay, binding to TGFβ ligand family members, effector function potential, and binding to neonatal receptor (FcRn). Clinical reference standard A10 was also evaluated for biological function in the in the same assays to compare reference standards. To evaluate consistency of product quality, four DS batches, including 1 clinical batch A1 and three batches from the process performance qualification (PPQ) campaign, A2, A3 and A5, were also characterized for potency, GDF-11 binding and FcRn binding assays.

(b) Strategy and Methods

The biological activity of representative Product 1 batches, including PRSA4, A10, A1, A11, A3 and A5 were determined using a cell-based reporter gene potency assay that measures the inhibition of GDF-11 induced activation of ActIIB receptor signaling. The reporter gene potency assay is used as a release and stability assay to monitor potency. In addition, Product 1 binding to TGFβ family members that bind to ActIIB receptor (Activin A, GDF-8, GDF-11, BMP-2, and BMP-7) was assessed using a Biacore binding characterization assay. Other TGFβ ligands were not assessed since they do not bind to ActIIB receptor due to the structure of the receptor ligand-receptor interface. FcRn association with Product 1 lot PRSA4 and representative process batches was also assessed using a Biacore FcRn binding assay and a competitive alphaELISA binding assay. Since Product 1 contains an intact Fc domain, PRSA4 and clinical reference standard A10 were characterized for binding to Fcγ receptors and lot A10 was assessed for the capability to trigger antibody-dependent cellular cytotoxicity (ADCC) and complement-dependent cellular cytotoxicity (CDC).

Biological Activity

The assay biological activity of Product 1 is determined using a cell-based reporter gene assay. The bioassay measures the dose-dependent ability of Product 1 to sequester GDF-11 and inhibit ActIIB phosphorylation of Smad2/3 as measured by the decreased transcriptional induction of a reporter gene under the regulation of a Smad2/3 specific promoter element. Product 1 inhibition of ActIIB signaling is measured using a stable human reporter gene cell line, A204-CAGA12-Luciferase. The cell response to recombinant human GDF-11 (rhGDF-11) stimulation of A204-CAGA12-Luc cells are quantitated from the amount of firefly luciferase luminescent signal. The luminescent signals of dilutions of Product 1 reference standard, assay control, and test samples are plotted using a 4-parameter logistic curve fit, assessed for similarity, and potency determined by the ratio of the IC50 of the reference standard to the test sample. The stable cell line Product 1 reporter gene bioassay format was validated and bridged to the historical transient transfection assay and used for measuring potency for Product 1 release and stability testing. The potency of PRSA4 was 96% relative to the previous reference standard A10.

Selective Binding of Product 1 to Specific TGFβ Ligand Family Members

The L79D point mutation in Product 1 results in selective binding to GDF-11 and reduced binding to other TGFβ family members. Binding of GDF-11 and other TGFβ family members to representative Product 1 lots and forced degraded samples was evaluated using Surface Plasmon Resonance. Product 1 was captured using an anti-human IgG (Fc) CM5 chip. Product 1 reference standard and test samples were diluted in 1×HPB-EP+buffer and then injected sequentially at 1.5 μg/mL concentration in 1×HBS-EP buffer manually to generate a constant level of bound Product 1 of approximately 100 RU for all experiments. For the GDF-11 binding assay, different concentrations of recombinant human GDF-11 were injected over the Product 1-bound surface and measurements for binding ($k_a$) were determined. The bound complexes were held in continuous flow of running buffer to measure the rate of dissociation ($k_d$). Response signals were background subtracted using a black surface and running buffer. Additional TGFβ family members (Activin A, GDF-8, BMP-2, and BMP-7) were also evaluated for Product 1 binding. The sensograms generated from the ActIIB ligand dilution series for each Product 1 sample were evaluated using Biacore T200 evaluation software and the affinity constant $K_D$ (M) was calculated using 1:1 Langmuir binding model. For the 1:1 binding model $k_a$, $k_d$, $R_{max}$ and $t_c$ was set to global fitting and RI was set to local fitting. A total of at least 3 replicates were performed and the observed binding kinetics were averaged to report mean binding parameter for each Product 1 test sample. FIG. 15 shows a sensogram of Product 1 binding to recombinant human GDF-11 for PRSA4. The mean KD for PRSA4 from three independent replicates was 1.03 pM. Binding to other representative lots of GDF-11 was also of high affinity and ranged between 0.02 to 1.8 pM, and fell within the within the variability of the assay. Average binding affinity of PRSA4 to GDF-8 was similar compared to GDF-11 with an average of 4 pM, consistent with the high level of sequence and functional similarity of GDF-8 and GDF-11 (Sako, J. Biol. Chem., 285 (27): 21037-48 (2010); Walker, BMC Miol., 15 (1): 19 (2017)). No detectable binding activity was observed for Activin A, BMP-2 and BMP-7 consistent with the role of the L79D mutation in Product 1 to impact binding to these other TGFβ ligand family members. These data agree with published results for other preparations of ActIIB (L79D)-Fc (Sako, J. Biol. Chem., 285 (27): 21037-48 (2010); Suragani, Nat. Med., 20 (4): 408-14 (2014)).

Evaluation of Product 1 Effector Functional Potential

Product 1 contains the fragment crystallizable (Fc) domain and has the potential to bind to Fcγ receptors (FcγR) and complement (C1q) to elicit Fc-dependent effector functions (Nimmerjahn and Ravetch, Nat Rev Immunol., 8 (1): 34-47 (2007)). Product 1 binding to FcγRIA, FcγRIIA-His, FcγRIIA-Arg, FcγRIIIA-Val, and FcγRIIIA-Phe was assessed using a competitive alphaELISA assay format that measures the ability of Product 1 to compete for binding to a human IgG antibody.

Binding of Product 1 to Neonatal Receptor (FcRn)

The half-life of IgG antibodies is impacted by the pH-dependent interaction with the neonatal receptor (FcRn). The binding of representative lots of Product 1 to human FcRn was assessed using both Surface Plasmon Resonance (Biacore, Sweden) and by alphaELISA. For Biacore evaluation, purified Human FcRn was immobilized covalently using primary amine coupling to a flow cell of a biosensor chip using a Biacore T-200 instrument (Biacore, Sweden). Dilutions of Product 1 were injected in a buffer a pH 6.0 in triplicate to measure the rate of association ($K_a$). Running buffer at pH 7 was passed over continuously to measure the rate of dissociation ($K_d$). The resulting sensograms were globally fit to a 1:1 binding model and analyzed using Biacore T-200 evaluation software to determine the $k_a$, $k_d$ and $K_D$ kinetic constants. A representative sensogram for Product 1 PRSA4 is shown in FIG. 16. The mean $K_D$ of PRSA4 was 1.96.

Product 1 binding to FcRn was also assessed by alpha-ELISA using a homogeneous AlphaScreen competition assay format (Perkin Elmer, Waltham, MA). The assay measures the ability of Product 1 test samples to compete with human IgG1 for binding to biotinylated FcRn. In the assay, serial dilutions of Product 1 test sample are mixed with a fixed amount of biotin-FcRn, human IgG1-conjugated to acceptor beads, and streptavidin-coated donor beads and incubated in assay buffer at pH 6 in an assay plate. After a timed incubation, assay plates are read for the signal generated by the signal generated using a plate reader. The level of interaction of IgG1-FcRn is determined by the signal generated by the AlphaELISA donor-acceptor signal and the results plotted versus Product 1 concentration (Log scale) to fit a 4-parameter logistic dose response curve. If the curves are parallel, the % relative binding to reference sample is determined by the ratio of the IC50 of the reference standard and test sample. FIG. 17 shows a representative dose-response curve evaluating the similarity of FcRn binding across the dilution range of the test samples between representative lots of Product 1. The binding affinity for A10 and PRSA4 were 1.145 and 1.229. The binding of PRSA4 relative to A10 was 93%.

Product Quality Consistency

To demonstrate consistency of product quality, biological function characterization was also performed on four additional DS batches, including one clinical batch A1 and three batches from PPQ campaign, A2, A3 and A5. Results of potency assay, GDF-11 binding by Biacore and FcRn binding by ELISA are presented in Table 15. Representative Product 1 process batches show highly similar potency, GDF-11 binding, and FcRn binding.

Biological Function Characterization Results for Product 1 Batches A1, A2, A3, A4 and A5

TABLE 15

| Parameter | Relative Levels (%) | | | | |
| --- | --- | --- | --- | --- | --- |
| | A1 | A2 | A3 | A4 | A5 |
| Potency (Relative to A10) (%) | 93 | 88 | 107 | 96 | 95 |
| GDF-11 Binding (SPR) Mean ka (1/Ms) | 2.38E+08 | 5.84E+07 | 1.35E+08 | 4.90E+07 | 9.85E+10 |
| GDF-11 Binding Mean ka (1/S) | 4.48E−05 | 3.46E−05 | 3.39E−05 | 5.06E−05 | 4.61E−05 |
| GDF Binding Assay Mean kp (M) | 1.88E−13 | 5.92E−13 | 2.51E−13 | 1.03E−12 | 4.68E−14 |
| GDF Binding Assay Mean kp (pmol) | 0.19 | 0.59 | 0.25 | 1.03 | 0.25 |
| FcRn binding (Relative to A10) (%) | 103 | 100 | 95 | 93 | 102 |

(c) Results

A summary of the biological characterization results for Product 1 is presented in Table 16.

TABLE 16

| Sub-section | Results |
| --- | --- |
| Biological activity by cell-based reporter gene assay | Results confirmed the biological activity of PRSA4 relative to A10 reference standard with a potency of 96%. Product 1 batches A1, A11, A3 and A5 were determined to have a potency relative to reference standard of 93%, 88%, 107% and 94%, respectively. |
| TGFβ ligand binding (GDF-11 binding) | Product 1 selectively binds to GDF-11 with high affinity. Product 1 binds with reduced affinity to GDF-8 compared to GDF-11, or no detectable binding to other TGFβ family members. Product 1 from all DS batches tested binds to GDF-11 with similar affinity. |
| Evaluation of Fc Effector Function | Product 1 acts as a selective soluble ligand trap and does not induce effector function (ADCC, CDC). |
| FcRn binding | Product 1 PRSA4 and A10 reference standard bind to FcRn with similar affinities. Product 1 from all DS batches tested binds to FcRn with similar affinity. |
| Product Quality Consistency | All drug substance batches from the PPQ and prior Product 1 process batches show similar potency, and GDF-11 binding and FcRn binding affinity. |

Mechanism of Action

Product 1 is a recombinant fusion protein consisting of the extracellular domain (ECD) of human activin receptor IIB (ActRIIB) linked to the human IgG1 Fc domain. The ActIIB receptor and its ligands are members of the TGFβ superfamily that induce signaling pathways regulating cellular development and differentiation, including erythropoiesis. Product 1 contains a single point mutation (L79D) in the ligand binding domain which enables high affinity binding to Growth Differentiation Factor 11 (GDF-11), but eliminates or reduces binding to other TGFβ ligands (Sako, J. Biol. Chem., 285 (27): 21037-48 (2010)). GDF-11 binding to ActIIB receptor induces the phosphorylation of the transcriptional regulators Smad2 and Smad3, resulting in the inhibition of erythropoiesis (Suragani, Nat. Med., 20 (4): 408-14 (2014)). Product 1 is an erythroid maturation agent that binds and sequesters GDF-11 preventing its binding to the ActIIB receptor which results in an increased number of red blood cells.

Selective Binding of Product 1 to Specific TGFβ Ligand Family Members

FIG. 15 shows a sensogram of Product 1 binding to recombinant human GDF-11 for PRSA4. The mean $K_D$ for PRSA4 from three independent replicates was 1.03 pM. Binding to other representative lots of GDF-11 was also of high affinity and ranged between 0.02 to 1.8 pM, and fell within the within the variability of the assay. Average binding affinity of PRSA4 to GDF-8 was similar compared to GDF-11 with an average of 4 pM, consistent with the high level of sequence and functional similarity of GDF-8 and GDF-11 (Sako, J. Biol. Chem., 285 (27): 21037-48 (2010); Walker, BMC Miol., 15 (1): 19 (2017)). No detectable binding activity was observed for Activin A, BMP-2 and BMP-7 consistent with the role of the L79D mutation in Product 1 to impact binding to these other TGFβ ligand family members. These data agree with published results for other preparations of ActIIB (L79D)-Fc (Sako, J. Biol. Chem., 285 (27): 21037-48 (2010); Suragani, Nat. Med., 20 (4): 408-14 (2014)).

Evaluation of Product 1 Effector Functional Potential

Table 17 shows the experimentally determined binding constants for Product 1 A10 and PRSA4 that are consistent with the expected affinity for Fcγ receptors to human Fc (Bruhns, (2018)).

Product 1 Binding to FcγR

TABLE 17

| Fcγ Receptor | IC50 (µg/mL) | |
|---|---|---|
| | A10 | PRSA4 |
| FcγRIA (CD64) | 0.04 | 0.03 |
| FcγRIIA-His (CD32A-H) | 3.26 | 3.16 |
| FcγRIIA-Arg (CD32A-R) | 10.82 | 11.23 |
| FcγRIIIA-Val (CD16A-V) | 0.23 | 0.39 |
| FcγRIIIA-Phe (CD16A-F) | 1.59 | 2.50 |

Product 1 is a high affinity soluble ligand trap for GDF-8 and GDF-11 (FIGS. 18A-18L). The data presented in FIG. 18B demonstrates that GDF-11 can be detected in complex with ActIIB receptor on the cell surface of the cell line used in the Product 1 bioassay (A204-GAGA12-Luc) when stained with an antibody to GDF-11 compared to isotype control (FIG. 18A; overlay FIG. 18I), but this is blocked if GDF-11 is pre-incubated with Product 1 lot PRSA4 (FIG. 18C, overlay FIG. 18J). Product 1 does not bind to the cell surface of the cells either in the absence of GDF-11 (FIG. 18D) as compared to iso-type control antibody (FIG. 18E, overlay FIG. 18K). Product 1 is not detected in complex with the A204-CAGA12-Luc cell line that has been pre-incubated with high, medium, or low concentrations of GDF-11 (FIG. 18F, FIG. 18G, and FIG. 18H; overlay FIG. 18L) demonstrating that Product 1 cannot form a cell surface ligand-receptor complex with ActIIB/ActIB receptor expressing cells. Binding to target antigen on the surface of target cells is required for an antibody or Fc containing protein to recruit or activate effector cells or elicit Fc effector function via a stable complex formed between the antigen on the surface of the target cell, the Fc containing protein, and FcγRs expressed on the surface of the effector cell (Nimmerjahn and Ravetch, Nat Rev Immunol., 8 (1): 34-47 (2007)). Therefore, while Product 1 binds to FcγRs it cannot elicit effector functions due to the inability to bind to the cell surface that is required to recruit and thereby activate FcγR-expressing effector cells.

In order to further demonstrate the inability of Product 1 to induce effector functions, other cell types that express ActIIB receptor were used to assess the effector function potential of Product 1. Human sk-br-3 cells that endogenously express high HER2 receptor were transduced to express Activin receptors ActIA and ActIIB to the same level as HER2 receptor. Anti-HER2 antibody (trastuzumab, Herceptin) and an engineered human NK cell line stably expressing CD16-Val were incubated with the SK-BR-3/ActIA, ActIIB cell line. As shown in FIG. 19, Anti-HER2 antibodies were shown to dose-dependently induce antibody-dependent cellular cytotoxicity (ADCC). However, as shown in FIG. 19, Product 1 lot A10 either in the (C) absence or (D) presence of GDF-11 binding did not induce an ADCC response at any protein concentration, comparable to (E) SK-BR-3 and NK92-CD16 cell only negative controls. Therefore, Product 1 does not induce ADCC.

Similarly, using the same transfected cell target (sk-br-3/ActIB,ActIIB), Product 1 lot A10 does not induce complement-dependent cellular cytotoxicity (CDC) in the presence of complement (C1q) containing serum (FIG. 20).

The inability of Product 1 to elicit a detectable cell surface binding or effector function is consistent with other soluble ligand traps that bind to secreted or cell surface non-processed ligands. Therefore, the mechanism of action of Product 1 does not include effector function.

Five batches from current process, including 4 batches from PPQ campaign, were analyzed for potency by reporter gene assay, GDF-11 binding by biacore and FcRn binding by ELISA. Results for all batches were consistent.

10. EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

11. SEQUENCES

The Sequences in Table 18 are amino acid and nucleic acid sequences that can be used with the methods and compositions described herein.

TABLE 18

| SEQ ID NO: | Description | Sequence |
|---|---|---|
| 1 | Amino acid sequence of Product 1 minus the C-terminus lysine. Conserved N-glycosylation sites are underlined and shown in bold. 334 amino acids in length | ETRECIYYNA NWELERTNQS GLERCEGEQD KRLHCYASWR NSSGTIE<u>L</u>VK KGCWDDDFNC YDRQECVATE ENPQVYFCCC EGNFCNERFT HLPEAGGPEV TYEPPPTGGG THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNK<u>A</u>LPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPG |
| 2 | Amino acid sequence of full length Product 1. Conserved N-glycosylation sites are underlined and shown in bold. 335 amino acids in length | ETRECIYYNA NWELERTNQS GLERCEGEQD KRLHCYASWR NSSGTIE<u>L</u>VK KGCWDDDFNC YDRQECVATE ENPQVYFCCC EGNFCNERFT HLPEAGGPEV TYEPPPTGGG THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNK<u>A</u>LPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 3 | Full length extracellular domain (ECD) of ActRIIB including signal peptide (underlined) | <u>MTAPWVALAL LWGSLWPGSG</u> RGEAETRECI YYNANWELER TNQSGLERCE GEQDKRLHCY ASWRNSSGTI ELVKKGCWLD DENCYDRQEC VATEENPQVY FCCCEGNFCN ERFTHLPEAG GPEVTYEPPP TAPT |
| 4 | Modified extracellular domain (ECD) of ActRIIB Conserved N-glycosylation sites are underlined and shown in bold. Threonines (T) shown in bold and underlined indicate potential O-glycosylation sites. Asp55 amino acid (corresponding to L79D amino acid substitution in full-length ECD) is underlined and shown in bold. 107 amino acids in length | ETRECIYYNA NWELERTNQS GLERCEGEQD KRLHCYASWR NSSGTIE<u>L</u>VK KGCWDDDFNC YDRQECVATE ENPQVYFCCC EGNFCNERFT HLPEAGGPEV TYEPPPT |
| 5 | Tissue plasminogen activator (TPA) signal sequence 24 amino acids in length | MDAMKRGLCC VLLLCGAVFV SPGAAETREC |
| 6 | Encoded sequence from Expression Vector 1. TPA signal sequence is underlined and shown in bold. Linker region is underlined and shown in bold. * Encodes TGA nontranslated stop codon. | MDAMKRGLCC VLLLCGAVFV SPGAAETREC IYYNANWELE RTNQSGLERC EGEQDKRLHC YASWRNSSGT IELVKKGCWD DDFNCYDRQE CVATEENPQV YFCCCEGNFC NERFTHLPEA GGPEVTYEPP PTGGGTHTCP PCPAPELLGG PSVFLFPPKP <u>KDTLM</u>ISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK * |
| 7 | Nucleic acid sequence that encodes Product 1 from Expression Vector 1. TPA signal sequence is underlined and shown in bold. | <u>ATGGATGCAATGAAGAGA GGGCTCTGCTGTGTGCTG CTGCTGTGTGGAGCAGTC TTCGTTTCGCCCGGCGCC</u>GCCGAAACCCGCGAATGT ATTTATTACAATGCTAAT TGGGAACTCGAACGGACG AACCAATCCGGGCTCGAA CGGTGTGAGGGGGAACAG GATAAACGCCTCCATTGC TATGCGTCGTGGAGGAAC TCCTCCGGGACGATTGAA CTGGTCAAGAAAGGGTGC TGGGACGACGATTTCAAT TGTTATGACCGCCAGGAA TGTGTCGCGACCGAAGAG |

TABLE 18-continued

| SEQ ID NO:Description | Sequence |
|---|---|
| | AATCCGCAGGTCTATTTC TGTTGTTGCGAGGGGAAT TTCTGTAATGAACGGTTT ACCCACCTCCCCGAAGCC GGCGGGCCCGAGGTGACC TATGAACCCCCGCCCACC GGTGGTGGAACTCACACA TGCCCACCGTGCCCAGCA CCTGAACTCCTGGGGGGA CCGTCAGTCTTCCTCTTC CCCCCAAAACCCAAGGAC ACCCTCATGATCTCCCGG ACCCCTGAGGTCACATGC GTGGTGGTGGACGTGAGC CACGAAGACCCTGAGGTC AAGTTCAACTGGTACGTG GACGGCGTGGAGGTGCAT AATGCCAAGACAAAGCCG CGGGAGGAGCAGTACAAC AGCACGTACCGTGTGGTC AGCGTCCTCACCGTCCTG CACCAGGACTGGCTGAAT GGCAAGGAGTACAAGTGC AAGGTCTCCAACAAAGCC CTCCCAGCCCCCATCGAG AAAACCATCTCCAAAGCC AAAGGGCAGCCCCGAGAA CCACAGGTGTACACCCTG CCCCCATCCCGGGAGGAG ATGACCAAGAACCAGGTC AGCCTGACCTGCCTGGTC AAAGGCTTCTATCCCAGC GACATCGCCGTGGAGTGG GAGAGCAATGGGCAGCCG GAGAACAACTACAAGACC ACGCCTCCCGTGCTGGAC TCCGACGGCTCCTTCTTC CTCTATAGCAAGCTCACC GTGGACAAGAGCAGGTGG CAGCAGGGGAACGTCTTC TCATGCTCCGTGATGCAT GAGGCTCTGCACAACCAC TACACGCAGAAGAGCCTC TCCCTGTCTCCGGGTAAA TGA |

What is claimed:

1. A composition comprising an ActRIIB-Fc fusion protein comprising the amino acid sequence of SEQ ID NO:1, wherein the composition comprises fusion proteins having one or more of the following changes to said amino acid sequence in the following amounts:
  a. one or more aspartic acid residues of SEQ ID NO: 1 are isomerized in 0.4% to 0.6% of said fusion proteins; or
  b. one or more methionine residues of SEQ ID NO: 1 are oxidized in 0.2% to 1.2% of said fusion proteins.

2. The composition of claim 1, wherein the composition comprises a plurality of fusion proteins having one or more of the following additional changes to the amino acid sequence of SEQ ID NO: 1 in the following amounts:
  a. the C-terminal amino acid of 95%-95.4% of said fusion proteins is glycine; or
  b. the C-terminal-most proline of SEQ ID NO: 1 is amidated in 2.0%-2.9% of said fusion proteins; or
  c. the N-terminal glutamate of SEQ ID NO: 1 is substituted with pyroglutamate in 0.9%-1.1% of said fusion proteins; or
  d. asparagine 203 of SEQ ID NO: 1 is deamidated in 3.6%-3.9% of said fusion proteins; or
  e. asparagine 249 of SEQ ID NO: 1 is deamidated in 0.6% of said fusion proteins; or
  f. asparagine 272 or 277 of SEQ ID NO: 1 are deamidated in 5.2%-6.1% of said fusion proteins; or
  g. aspartic acid residues 55, 56 and/or 57 of SEQ ID NO: 1 are isomerized in 0.5%-0.6% of said fusion proteins; or
  h. aspartic acid residue 168 of SEQ ID NO: 1 is isomerized in 0.4% of said fusion proteins; or
  i. aspartic acid residue 289 of SEQ ID NO: 1 is isomerized in 0.4% of said fusion proteins; or
  j. methionine residue 140 of SEQ ID NO: 1 is oxidized in 1.1%-1.2% of said fusion proteins; or
  k. methionine residue 246 of SEQ ID NO: 1 is oxidized in 0.2%-0.3% of said fusion proteins; or
  l. methionine residue 316 of SEQ ID NO: 1 is oxidized in 0.6%-0.8% of said fusion proteins.

3. The composition of claim 1, wherein the fusion proteins have one or more of the following changes to the amino acid sequence of SEQ ID NO: 1 in the following amounts:
  a. at least 95% of said fusion proteins in said composition lack a C-terminal lysine; or
  b. the C-terminal-most proline of SEQ ID NO: 1 is amidated in no more than 2.9% of said fusion proteins; or
  c. the N-terminal glutamate of SEQ ID NO: 1 is substituted with pyroglutamate in no more than 1.1% of said fusion proteins; or
  d. one or more asparagine residues of SEQ ID NO:1 are deamidated in no more than 3.9% of said fusion proteins.

4. The composition of claim 1, wherein the fusion proteins have one or more of the following changes to the amino acid sequence of SEQ ID NO: 1 in the following amounts:
  a. the C-terminal-most proline of SEQ ID NO: 1 is amidated in 2.0%-2.9% of said fusion proteins; and/or
  b. the N-terminal glutamate of SEQ ID NO:1 is substituted with pyroglutamate in 0.9%-1.1% of said fusion proteins; and/or
  c. one or more asparagine residues of SEQ ID NO: 1 are deamidated in 0.6%-6.1% of said fusion proteins.

5. A polypeptide comprising the amino acid sequence of SEQ ID NO:1, wherein:
  a. the polypeptide comprises one or more N-linked glycosylations; and/or
  b. the polypeptide comprises one or more O-linked glycosylations; and/or
  c. the N-terminal glutamic acid is pyroglutamic acid (PCA or pyroE); and/or
  d. the asparagine at 203 is deamidated; and/or
  e. the asparagine at 249 is deamidated; and/or
  f. the asparagine at 272 or 277 is deamidated; and/or
  g. the aspartic acid at 55, 56, or 57 is isomerized; and/or
  h. the aspartic acid at 168 is isomerized; and/or
  i. the aspartic acid at 289 is isomerized; and/or
  j. the methionine at 140 is oxidized; and/or
  k. the methionine at 246 is oxidized; and/or
  l. The lysine at 134 or 136 is glycated; and/or
  m. the lysine at 208, 210, or 214 is glycated.

6. A composition comprising a plurality of polypeptides comprising the amino acid sequence of SEQ ID NO:1, wherein:
  a. the plurality of polypeptides, when digested to completion with trypsin endopeptidase, results in a trypsin peptide map essentially as shown in FIG. 4 or 5, wherein said peptides have been separated by reverse phase ultra performance liquid chromatography (RP-UPLC) using a C18 column with a gradient of acetonitrile in 0.05% trifluoroacetic acid (TFA) (v/v), monitoring of ultraviolet (UV) absorbance at 214 nm, and identification of peptides by inline mass spectrometry (MS) and tandem MS (MS/MS) analysis; or
  b. the plurality of polypeptides results in a charge heterogeneity profile substantially as shown in FIG. 6, 7, 8 or 9 using imaged capillary isoelectrofocusing.

* * * * *

SEQUENCE LISTING

<160> NUMBER OF SEQ ID NOS: 7

<210> SEQ ID NO 1
<211> LENGTH: 334
<212> TYPE: PRT
<213> ORGANISM: Artificial Sequence
<220> FEATURE:
<223> OTHER INFORMATION: Amino acid sequence of Product 1 minus the C-terminus lysine

<400> SEQUENCE: 1

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
            35                  40                  45

Val Lys Lys Gly Cys Trp Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

```
Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly
                325                 330

<210> SEQ ID NO 2
<211> LENGTH: 335
<212> TYPE: PRT
<213> ORGANISM: Artificial Sequence
<220> FEATURE:
<223> OTHER INFORMATION: Amino acid sequence of full length Product 1

<400> SEQUENCE: 2

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205
```

```
Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 3
<211> LENGTH: 134
<212> TYPE: PRT
<213> ORGANISM: Artificial Sequence
<220> FEATURE:
<223> OTHER INFORMATION: Full length extracellular domain (ECD) of
      ActRIIB including signal peptide

<400> SEQUENCE: 3

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
    130

<210> SEQ ID NO 4
<211> LENGTH: 107
<212> TYPE: PRT
<213> ORGANISM: Artificial Sequence
<220> FEATURE:
<223> OTHER INFORMATION: Modified extracellular domain (ECD) of ActRIIB

<400> SEQUENCE: 4

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
```

```
                    35                  40                  45
Val Lys Lys Gly Cys Trp Asp Asp Asp Phe Asn Cys Tyr Asp Arg Gln
 50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr
            100                 105

<210> SEQ ID NO 5
<211> LENGTH: 24
<212> TYPE: PRT
<213> ORGANISM: Artificial Sequence
<220> FEATURE:
<223> OTHER INFORMATION: Tissue plasminogen activator (TPA) signal
      sequence

<400> SEQUENCE: 5

Met Asp Ala Met Lys Arg Gly Leu Cys Cys Val Leu Leu Leu Cys Gly
  1               5                  10                  15

Ala Val Phe Val Ser Pro Gly Ala
                 20

<210> SEQ ID NO 6
<211> LENGTH: 360
<212> TYPE: PRT
<213> ORGANISM: Artificial Sequence
<220> FEATURE:
<223> OTHER INFORMATION: Encoded sequence from Expression Vector 1

<400> SEQUENCE: 6

Met Asp Ala Met Lys Arg Gly Leu Cys Cys Val Leu Leu Leu Cys Gly
  1               5                  10                  15

Ala Val Phe Val Ser Pro Gly Ala Ala Glu Thr Arg Glu Cys Ile Tyr
                 20                  25                  30

Tyr Asn Ala Asn Trp Glu Leu Glu Arg Thr Asn Gln Ser Gly Leu Glu
             35                  40                  45

Arg Cys Glu Gly Glu Gln Asp Lys Arg Leu His Cys Tyr Ala Ser Trp
 50                  55                  60

Arg Asn Ser Ser Gly Thr Ile Glu Leu Val Lys Lys Gly Cys Trp Asp
 65                  70                  75                  80

Asp Asp Phe Asn Cys Tyr Asp Arg Gln Glu Cys Val Ala Thr Glu Glu
                 85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
            115                 120                 125

Pro Pro Pro Thr Gly Gly Gly Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
            195                 200                 205
```

```
Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
            245                 250                 255

Arg Glu Pro Gln Val Tyr Thr Leu Pro Pro Ser Arg Glu Glu Met Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 7
<211> LENGTH: 1083
<212> TYPE: DNA
<213> ORGANISM: Artificial Sequence
<220> FEATURE:
<223> OTHER INFORMATION: Nucleic acid sequence that encodes Product 1
      from Expression Vector 1

<400> SEQUENCE: 7
atggatgcaa tgaagagagg ctctgctgtt gtgctgctgc tgtgtggagc agtcttcgtt      60
tcgcccggcg ccgccgaaac ccgcgaatgt atttattaca atgctaattg ggaactcgaa     120
cggacgaacc aatccgggct cgaacggtgt gaggggggaac aggataaacg cctccattgc    180
tatgcgtcgt ggaggaactc ctccgggacg attgaactgg tcaagaaagg gtgctgggac    240
gacgatttca attgttatga ccgccaggaa tgtgtcgcga ccgaagagaa tccgcaggtc    300
tatttctgtt gttgcgaggg gaatttctgt aatgaacggt ttacccacct ccccgaagcc   360
ggcgggcccg aggtgaccta tgaacccccg cccaccggtg gtggaactca cacatgccca    420
ccgtgcccag cacctgaact cctgggggga ccgtcagtct tcctcttccc cccaaaaccc    480
aaggacaccc tcatgatctc ccggaccct gaggtcacat gcgtggtggt ggacgtgagc     540
cacgaagacc ctgaggtcaa gttcaactgg tacgtgacgg cgtggaggt gcataatgcc     600 aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag gcagccccg agaaccacag    780 gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga acgtcttctc atgctccgtg   1020
```

```
atgcatgagg ctctgcacaa ccactacacg cagaagagcc tctccctgtc tccgggtaaa    1080
tga                                                                 1083
```